(12) United States Patent
Sun et al.

(10) Patent No.: US 11,858,942 B2
(45) Date of Patent: *Jan. 2, 2024

(54) TRIAZOLOTRIAZINE DERIVATIVES AS A2A RECEPTOR ANTAGONISTS

(71) Applicant: ZHEJIANG VIMGREEN PHARMACEUTICALS, LTD., Zhejiang (CN)

(72) Inventors: Sanxing Sun, Zhejiang (CN); Jinqi Ye, Zhejiang (CN); Long Zhao, Zhejiang (CN); Chongbo Hu, Zhejiang (CN); Zhengshu Chen, Zhejiang (CN)

(73) Assignee: ZHEJIANG VIMGREEN PHARMACEUTICALS, LTD., Zhejiang (CN)

( * ) Notice: Subject to any disclaimer, the term of this patent is extended or adjusted under 35 U.S.C. 154(b) by 197 days.

This patent is subject to a terminal disclaimer.

(21) Appl. No.: 17/255,451

(22) PCT Filed: Jun. 26, 2018

(86) PCT No.: PCT/IB2018/054690
§ 371 (c)(1),
(2) Date: Dec. 23, 2020

(87) PCT Pub. No.: WO2020/002968
PCT Pub. Date: Jan. 2, 2020

(65) Prior Publication Data
US 2021/0292334 A1   Sep. 23, 2021

(51) Int. Cl.
C07D 519/00 (2006.01)
A61P 35/00 (2006.01)
A61K 31/53 (2006.01)
C07D 487/04 (2006.01)

(52) U.S. Cl.
CPC .................. C07D 487/04 (2013.01)

(58) Field of Classification Search
CPC ..... C07D 487/04; C07D 519/00; A61P 35/00; A61K 31/53
See application file for complete search history.

(56) References Cited

U.S. PATENT DOCUMENTS

| | | | |
|---|---|---|---|
| 5,270,311 A * | 12/1993 | Caulkett | A61P 25/04 544/212 |
| 5,356,894 A | 10/1994 | Caulkett et al. | |
| 5,380,714 A | 1/1995 | Jones et al. | |
| 5,789,407 A | 8/1998 | Suzuki et al. | |
| 2007/0173505 A1 | 7/2007 | Peng et al. | |

FOREIGN PATENT DOCUMENTS

| | | | |
|---|---|---|---|
| CN | 1056879 A | | 12/1991 |
| EP | 0667349 A1 | | 8/1995 |
| KR | 20050044600 A | | 5/2005 |
| WO | 2004092173 A2 | | 10/2004 |

OTHER PUBLICATIONS

M. Jörg et al., Bioorg. Med. Chem. Lett. 23 (2013) 3427-3433 (Year: 2013).*
Nicholas A. Meanwell, Top Med Chem (2015) 9: 283-382, "The Influence of Bioisosteres in Drug Design: Tactical Applications to Address Developability Problems", published online on Jan. 28, 2014. (Year: 2015).*
Jörg et al. Bioorganic & Medicinal Chemistry Letters 23 (2013) 3427-3433 (Year: 2013).*
Patani, Chemical Reviews, 1996, 96, 3147-3176, "Bioisosterism: A Rational Approach in Drug Design" (Year: 1996).*
PCT/IB2018/054690 International Search Report dated Mar. 28, 2019.
Dong Guo, et al., Binding Kinetics of ZM241385 Derivatives at the human Adenosine A2A Receptor, CehmMedChem, vol. 9, No. 4, Dec. 31, 2014.
China 2018800482301 Search Report dated Jul. 27, 2022.
EP 18924546.7 Extended European Search Report dated May 11, 2022.
Kohara, Y., et al., Synthesis and Angiotension II Receptor Antagonistc Activites of Benzimidazole Derivatives Bearing Acidic Heterocycles as Novel Tetrazole Bioisosteres, J. Med. Chem, vol. 39, pp. 5228-5235, American Chemical Society, Jul. 26, 1996.
Miura, S-i., et al., Unique binding behavior of the recently approved aniotensin II receptor blocker azilsartan compared with that of candesartan, Hypertens. Res. 36(2); pp. 134-139, The Japanese Society of Hypertension, Feb. 2013.
Noda, K., et al., Tetrazole and Carboxylate Groups of Angiotensin Receptor Antagonists Bind to the Same Subsite by Different Mechanisms, The Journal of Biological Chemistry, Vo. 270, No. 5, pp. 2284-2289, The American society for Biochemistry and Molecular Biology, Inc., Feb. 3, 1995.

* cited by examiner

*Primary Examiner* — Jared Barsky
*Assistant Examiner* — Liyuan Mou
(74) *Attorney, Agent, or Firm* — Honigman LLP; Thomas A. Wootton, Esq.; Jonathan P. O'Brien

(57) ABSTRACT

The present invention provides triazolotriazine derivatives of formula (1) as A2A receptor antagonists. Compounds of formula (1) and pharmaceutical compositions including the compounds can be used for the treatment of disorders related to A2A receptor hyperfunctioning, such as certain types cancers. Compounds of formula (1) and methods of preparing the compounds are disclosed in the invention.

Formula 1

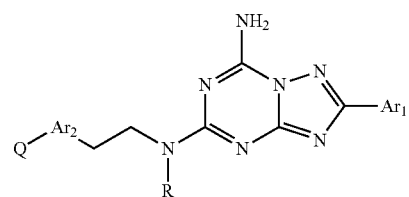

3 Claims, No Drawings

TRIAZOLOTRIAZINE DERIVATIVES AS A2A RECEPTOR ANTAGONISTS

CROSS-REFERENCE TO RELATED APPLICATIONS

This application is a National Stage Application and claims priority under 35 U.S.C. § 371 to Patent Cooperation Treaty application PCT/IB2018/054690, filed Jun. 26, 2018, priority is claimed to this application and the disclosures of this prior application is considered part of the disclosure of this application and to the extent allowed the entire contents of the aforementioned application are incorporated herein.

FIELD OF THE INVENTION

The present invention relates to compounds of triazolotriazine derivatives that can be used as A2A receptor antagonists. The present invention further relates to methods of preparing said compounds and pharmaceutical compositions comprising said compounds. The compounds and compositions thereof can be used for the treatment or prevention of disorders associated with hyperactive A2A receptors, such as A2A receptor-mediated immune tolerance to cancer and related abnormal cell proliferation.

BACKGROUND OF THE INVENTION

Adenosine is a naturally occurring purine nucleoside that modulates various physiological functions. Adenosine binds to purinergic receptors, which are members of the G protein-coupled receptor (GPCR) family that includes adenosine A1, A2A, A2B and A3 receptors (A1R, A2AR, A2BR and A3R). Among them, the Adenosine A2A receptor (A2AR) couples to adenylate cyclase in a stimulatory manner that induces classical second messenger pathways, including the production of cyclic adenosine monophosphate (cAMP) (Current Medicinal Chemistry. 2014, 21, 3918-3935). A2AR mediates multiple physiological effects of adenosine, both in the central nervous system and in peripheral tissues. The functional interactions between A2AR and dopamine D2 in the basal ganglia have triggered decades of investigation of A2AR antagonists as anti-Parkinson drugs. Other therapeutic applications of A2AR antagonism include cognition enhancement, neuroprotection, and painkilling. More recent studies have demonstrated that inhibition of A2AR may provide a powerful new treatment of cancer (Computational and Structural Biotechnology Journal. 2015, 15, 265-272).

Studies have shown that A2AR may protect tumors from the attack of anti-tumor T cells and other immune cells (PNAS. 2006, 103, No. 35, 13132-7). The immune system has evolved an array of regulatory mechanisms to protect against tissue damage from autoimmunity or during active response to pathogen. Both central mechanisms such as negative selection in the thymus and peripheral mechanisms such as deletion, anergy, and the deployment of regulatory T cells (Tregs) contribute to the establishment of self-tolerance. Included in these protective mechanisms are various inhibitory receptors that are upregulated on lymphocytes during an active immune response. These inhibitory receptors and their related signaling networks, known as "immune checkpoint pathways," provide a negative feedback mechanism that is crucial for the protection of tissues from immune attack. Yet, although the negative feedback loops created by the checkpoint pathways are critical in modulating excessive immune response, they are also subject to dysregulation in the presence of cancer and provide tumors with a means of immune evasion. The adenosine signaling is one of the various negative feedback mechanisms that serve to dampen immune response and protect tissues from the associated injury.

It is known that extracellular adenosine can signal through adenosine receptors including A1R, A2AR, A2BR, and A3R (Drug Dev. Res. 1996, 39, 243-52). Due to that A2AR and A2BR are expressed on a variety of immune cells and endothelial cells, adenosine signaling through A2AR (high affinity) and A2BR (low affinity) has an important role in protecting tissues during immune responses (Autoimmunity. 2007, 40, 425-32; Handb. Exp. Pharmacol. 2009, 193, 399-441; Cancer Discov. 2014, 4, 879-88). In particular, because of the higher affinity of adenosine binding on A2AR and the higher expression of A2AR on a much broader array of immune cells, most of this protective effect is carried through the A2A adenosine receptor (Nature. 2001, 414, 916-20).

Under normal physiologic conditions, the extracellular amount of adenosine is balanced by rapid cellular uptake that prevents a significant increase in extracellular levels (Clin. Invest. 2012, 122, 693-710; Gastroenterology. 2009, 136, 607-18). However, in the tumor microenvironment, increased cellular turnover, tissue breakdown and hypoxia trigger the release of a much larger amount of ATP and adenosine into the extracellular environment (Am. J. Physiol. 1993, 265, C577-606; Cancer Res. 1997, 57, 2602-5). Besides, while the build-up of extracellular adenosine is partly a result of direct liberation of intracellular adenosine that is formed from increased ATP metabolism during cellular stress, the adenosine level is also increased by the catabolism of extracellular ATP and ADP by the tandem activity of the ectonucleotidases CD39 and CD73, which are upregulated in a number of cell types within the tumor microenvironment, including endothelial cells, stromal cells, tumor cells, and, importantly, on several subsets of immune cells, including Tregs, CD8+ T cells, B cells, NK cells, dendritic cells (DC), myeloid derived suppressor cells (MDSCs), and tumor-associated macrophages (TAMs) (Cancer Immunol. Res. 2014, 2, 598-605; Cancer Discov. 2014, 4, 879-88; Clin. Cancer Res. 2013, 19, 5626-35; J. Biomed. Biotechnol. 2012, 2012, 485156). As a result, such high levels of extracellular adenosine can't be easily absorbed (Am. J. Physiol. 1993, 265, C577-606; Cancer Res. 1997, 57, 2602-5; Am. J. Physiol. 1987, 252, H886-93). In studies using a microdialysis probe, it is demonstrated that extracellular adenosine levels in solid tumors are 10-20 times higher than in adjacent tissues. Such high levels of adenosine are sufficient to disrupt the function of immune cells (Cancer Res. 1997, 57, 2602-5).

Indeed, the rise in extracellular adenosine level and activation of A2AR has a broad range of immunosuppressive effects (Cancer Res. 2007, 67, 5949-56), including increased production of immunosuppressive cytokines such as TGF-beta and IL-10 (Blood. 2008, 111, 251-9; Eur. J. Immunol. 2010, 40, 682-7), upregulation of alternate immune checkpoint pathway receptors such as PD-1 and LAG-3 (Blood. 2008, 111, 251-9; J. Immunol. 2007, 178, 4240-9), increased FOXP3 expression in CD4 T cells that drives a regulatory T cell phenotype, and induction of effector T cell anergy (Blood. 2008, 111, 251-9). Since Tregs express high levels of CD39 and CD73, as the CD4+ T cells are driven toward Treg phenotype by A2AR-mediated FOXP3 expression, an immunosuppressive amplification circuit that generates increasing amounts of adenosine is created and quickly dampens the immune response (J. Exp. Med. 2007, 204, 1257-65). In the end, the CD8+ effector cells become less cytotoxic and increasingly anergic under the influence of A2AR signaling (Blood 2008, 111, 251-9). What is more, in addition to dampening the effect of cytotoxic T cells, increased extracellular adenosine has been found to downmodulate the activity of a range of immune functions in the tumor microenvironment, including the activity of macrophages, NK cells, neutrophils, and dendritic cells (Blood. 2008, 112, 1822-31; Immunol Res. 2006, 36, 91-9; Blood. 2004, 103, 1391-7; Biochem. Pharmacol. 2000, 60, 993-9; Am. J. Respir. Cell Mol. Biol. 2009 40, 251-9).

Given the importance of adenosine signaling in mediating negative feedback loops of immune responses, pharmacologic blockade of A2A receptors on effector T cells, Tregs, NK cells, dendritic cells (DC), myeloid derived suppressor cells (MDSCs), and tumor-associated macrophages (TAMs) may counteract the immunosuppressive cloud of adenosine in the tumor microenvironment and enhance multiple phases of the immune response, including T cell activation, expansion, and effector function. Indeed, in vivo studies have shown that genetic or pharmacologic blockade of A2AR have profound effects on tissue inflammation, allowing for uncontrolled inflammatory response and tissue injury in mouse models of hepatitis and sepsis. The increased proliferative and destructive capacity of effector T cells against tumor in these studies clearly demonstrate the effectiveness of A2AR antagonism. In fact, even transient pharmacologic A2AR blockade is found to enhance immunologic memory, improving effector function several weeks after initial antigen challenge. Importantly, alternate inflammatory control mechanisms were unable to effectively compensate for the tissue damage resulting from the absence of A2AR signaling, thus establishing that A2AR signaling is a critical, non-redundant negative feedback control mechanism of immune responses (Computational and Structural Biotechnology Journal. 2015, 13, 265-272; Cancer Immunol. Immunother. 2012, 61, 917-26). This makes it conceivable that A2AR antagonists may provide a powerful treatment of cancer and other types of abnormal cell proliferation.

Accordingly, it is an object of the present invention to provide novel A2AR antagonists with desirable pharmaceutical properties. The goal is to achieve high efficacy for the treatment and prevention of cancer and other types of abnormal cell proliferation by restoring or enhancing immune responses.

DESCRIPTION OF THE INVENTION

The present invention relates to triazolotriazine compounds of general formula (1), including hydrates, solvates, pharmaceutically acceptable salts, prodrugs and complexes thereof,

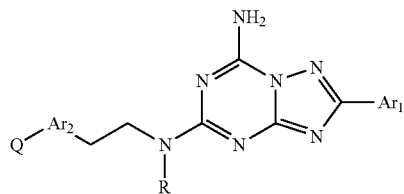

Formula 1 wherein:
R is hydrogen or optionally substituted $C_{1-5}$ alkyl; Any of said optionally substituted alkyls are substituted by halogen, cyano, hydroxyl, nitro, amino, alkylamino, cycloalkylamino, methyl, ethyl, methoxyl, ethoxyl, trifluoromethyl, trifluoroethyl, trifluoromethoxyl, or trifluoroethoxyl;

$Ar_1$ is a 5-6 membered aromatic ring that is optionally substituted with halogen, oxo, cyano, methyl, methoxyl, trifluoromethyl, or trifluoromethoxyl;

$Ar_2$ is a mono- or bicyclic aromatic ring that is optionally substituted with halogen, hydroxyl, cyano, methyl, methoxyl, trifluoromethyl, or trifluoromethoxyl; and Q is a mono- or bicyclic aromatic ring that is optionally substituted with X, an aminocarbonyl group that is optionally substituted with Y and Z on the nitrogen, an aminosulfonyl group that is optionally substituted with Y and Z on the nitrogen, a nitro group, or a cyano group. X is halogen, cyano, hydroxyl, nitro, amino, alkylamino, methoxyl, ethoxyl, trifluoromethoxyl, trifluoroethoxyl, optionally substituted $C_{1-9}$ alkyl, optionally substituted $C_{1-9}$ cycloalkyl, optionally substituted $C_{1-9}$ alkenyl, optionally substituted $C_{1-9}$ cycloalkenyl, optionally substituted aryl, optionally substituted heteroaryl, optionally substituted aralkyl, optionally substituted heteroaralkyl, optionally substituted heterocycloalkyl, or optionally substituted heterocycloalkenyl; Any of said optionally substituted groups are substituted by halogen, cyano, hydroxyl, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, heterocycloalkyl, aryl, heteroaryl, polyoxyethylene, polyoxypropylene, $C_{1-3}$ alkyl polyoxyethylene, or $C_{1-3}$ alkyl polyoxypropylene. Y and Z are each independently hydrogen, optionally substituted $C_{1-9}$ alkyl, optionally substituted mono- or bicyclic $C_{1-9}$ cycloalkyl, optionally substituted $C_{1-9}$ alkenyl, optionally substituted mono- or bicyclic $C_{1-9}$ cycloalkenyl, optionally substituted aryl, optionally substituted heteroaryl, optionally substituted aralkyl, optionally substituted heteroaralkyl, optionally substituted heterocycloalkyl, or optionally substituted heterocycloalkenyl; Any of said optionally substituted groups are substituted by halogen, cyano, hydroxyl, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, polyoxyethylene, polyoxypropylene, $C_{1-3}$ alkyl polyoxyethylene, or $C_{1-3}$ alkyl polyoxypropylene; Or Y and Z are joined to form an optionally substituted ring having from 3 to 10 ring atoms; Any of said optionally substituted ring is substituted by halogen, cyano, hydroxyl, oxo, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, polyoxyethylene, polyoxypropylene, $C_{1-3}$ alkyl polyoxyethylene, or $C_{1-3}$ alkyl polyoxypropylene.

An embodiment of the present invention includes compounds wherein R in formula (1) is hydrogen, methyl, or trifluoromethyl.

A preferred embodiment of the present invention includes compounds wherein R in formula (1) is hydrogen or methyl.

A most preferred embodiment of the present invention includes compounds wherein R in formula (1) is hydrogen.

Another embodiment of the present invention includes compounds wherein $Ar_1$ in formula (1) is optionally substituted imidazolyl, triazolyl, tetrazolyl, furanyl, thiophenyl, oxazolyl, isoxazolyl, thiazolyl, isothiazolyl, oxadiazolyl, thiadiazolyl, phenyl, pyridyl, pyridazinyl, pyrimidyl, pyrazinyl, or triazinyl; Any of said optionally substituted aromatic rings are substituted by halogen, oxo, cyano, methyl, methoxyl, trifluoromethyl, or trifluoromethoxyl.

A preferred embodiment of the present invention includes compounds wherein $Ar_1$ in formula (1) is selected from the aromatic groups shown in Table (1).

A most preferred embodiment of the present invention includes compounds wherein $Ar_1$ in formula (1) is 2-furanyl.

TABLE 1

Preferred structures of $Ar_1$ in formula (1)

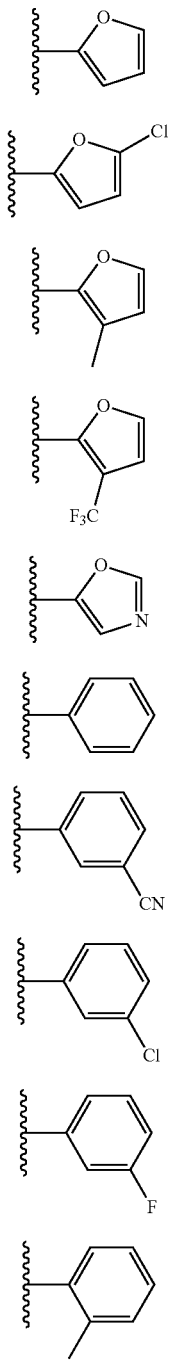

TABLE 1-continued

Preferred structures of $Ar_1$ in formula (1)

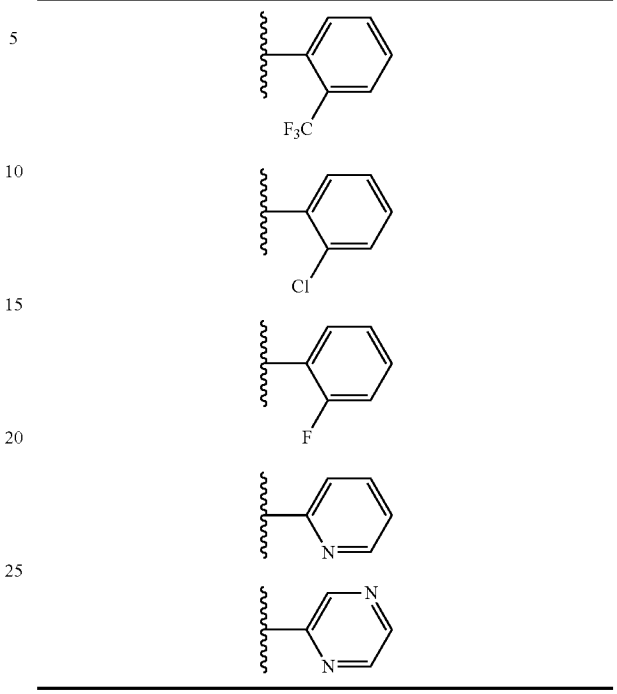

Another embodiment of the present invention includes compounds wherein $Ar_2$ in formula (1) is optionally substituted imidazolyl, triazolyl, tetrazolyl, furanyl, thiophenyl, oxazolyl, isoxazolyl, thiazolyl, isothiazolyl, oxadiazolyl, thiadiazolyl, phenyl, pyridyl, pyridazinyl, pyrimidyl, pyrazinyl, triazinyl, indolyl, isoindolyl, indazolyl, benzimidazolyl, azaindolyl, azaindazolyl, purinyl, benzofuranyl, isobenzofuranyl, benzothiophenyl, benzisoxazolyl, benzoisothiazolyl, benzoxazolyl, benzothiadiazolyl, quinolyl, isoquinolyl, quinoxalinyl, phthalazinyl, quinazolinyl, cinnolinyl, naphthyridinyl, pyridopyrimidinyl, pyridopyrazinyl, or pteridinyl; Any of said optionally substituted aromatic rings are substituted by halogen, hydroxyl, cyano, nitro, methyl, methoxyl, trifluoromethyl, or trifluoromethoxyl.

A preferred embodiment of the present invention includes compounds wherein $Ar_2$ in formula (1) is optionally substituted phenyl, pyridyl, pyridazinyl, or pyrimidyl; Any of said optionally substituted aromatic rings are substituted by halogen, hydroxyl, cyano, methyl, methoxyl, trifluoromethyl, or trifluoromethoxyl.

A most preferred embodiment of the present invention includes compounds wherein $Ar_2$ in formula (1) is phenyl or pyridyl that is optionally substituted with halogen or hydroxyl.

Another embodiment of the present invention includes compounds wherein Q in formula (1) is a mono- or bicyclic aromatic ring that is optionally substituted with X. X is halogen, cyano, hydroxyl, nitro, amino, alkylamino, methoxyl, ethoxyl, trifluoromethoxyl, trifluoroethoxyl, optionally substituted $C_{1-9}$ alkyl, optionally substituted $C_{1-9}$ cycloalkyl, optionally substituted $C_{1-9}$ alkenyl, optionally substituted $C_{1-9}$ cycloalkenyl, optionally substituted aryl, optionally substituted heteroaryl, optionally substituted aralkyl, optionally substituted heteroaralkyl, optionally substituted heterocycloalkyl, or optionally substituted heterocycloalkenyl; Any of said optionally substituted groups are substituted by halogen, cyano, hydroxyl, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, heterocycloalkyl, aryl, heteroaryl, polyoxyethylene, polyoxypropylene, $C_{1-3}$ alkyl polyoxyethylene, or $C_{1-3}$ alkyl polyoxypropylene.

A preferred embodiment of the present invention includes compounds wherein Q in formula (1) is a 5-6 membered aromatic ring that is optionally substituted with X. X is halogen, cyano, hydroxyl, nitro, amino, alkylamino, methoxyl, ethoxyl, trifluoromethoxyl, trifluoroethoxyl, optionally substituted Cis alkyl, optionally substituted $C_{1-5}$ cycloalkyl, optionally substituted $C_{1-5}$ alkenyl, optionally substituted $C_{1-5}$ cycloalkenyl, optionally substituted aryl, optionally substituted heteroaryl, optionally substituted aralkyl, optionally substituted heteroaralkyl, optionally substituted heterocycloalkyl, or optionally substituted heterocycloalkenyl; Any of said optionally substituted groups are substituted by halogen, cyano, hydroxyl, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, heterocycloalkyl, aryl, heteroaryl, polyoxyethylene, polyoxypropylene, $C_{1-3}$ alkyl polyoxyethylene, or $C_{1-3}$ alkyl polyoxypropylene.

A most preferred embodiment of the present invention includes compounds wherein Q in formula (1) is a tetrazole ring that is optionally substituted with X. X is optionally substituted $C_{1-3}$ alkyl or optionally substituted heterocycloalkyl; Any of said optionally substituted groups are substituted by halogen, cyano, hydroxyl, methyl, ethyl, methoxyl, ethoxyl, trifluoromethyl, trifluoroethyl, trifluoromethoxyl, trifluoroethoxyl, heterocycloalkyl, aryl, or heteroaryl.

The term "alkyl" includes both straight- and branched-chain saturated aliphatic hydrocarbon groups having a certain number of carbon atoms. For example, $C_4$ alkyl includes n-butyl, isobutyl, sec-butyl and t-butyl. The term "cycloalkyl" includes both mono- and bicyclic saturated aliphatic hydrocarbon groups having a certain number of carbon atoms.

The term "alkenyl" includes both straight- and branched-chain aliphatic hydrocarbon groups containing at least one carbon-to-carbon double bond. Preferably, one carbon-to-carbon double bond is present.

The term "aryl" includes both monocyclic and bicyclic aromatic rings comprising 5 to 14 ring atoms, preferably 6 to 10 ring atoms, unless it is specified otherwise. The aryl group can be optionally substituted with one or more substituents. The term "aryl" also includes both monocyclic and bicyclic heteroaryl rings comprising 5 to 14 ring atoms, preferably 6 to 10 ring atoms, unless it is specified otherwise.

The term "heterocycloalkyl," also known as "heterocyclyl," includes saturated monocyclic and bicyclic ring systems comprising 3 to 14 ring atoms, preferably 4 to 10 ring atoms, in which one or more of the atoms is an element other than carbon, for example nitrogen, oxygen or sulfur, alone or in combination. Examples of heterocycloalkyl groups include, for example, azetidinyl, hexahydroazepinyl, piperazinyl, piperidinyl, pyrrolidinyl, morpholinyl, tetrahydrofuranyl, thiomorpholinyl, and tetrahydrothienyl, and N-oxides thereof.

The term "halogen" includes fluoro, chloro, bromo and iodo. The term "trifluoromethyl" refers to the group (—$CF_3$). The term "hydroxyl" or "hydroxy" means an "—OH" group.

The compounds of formula (1) of the present invention may exist in one or more geometrical, enantiomeric, diastereoisomeric or tautomeric forms. The compounds of formula (1) of the present invention include all such isomeric forms, including racemic and other mixtures thereof.

In another aspect, the compounds of formula (1) of the present invention may exist in either solvated or unsolvated form. The term "solvated" is used herein to describe a compound complex that comprises a compound of the present invention and a number of pharmaceutically acceptable solvent molecules, such as water and ethanol molecules. The compounds of formula (1) of the present invention include all solvated or unsolvated forms thereof.

In another aspect, the compounds of formula (1) of the present invention may exist in a form of pharmaceutically acceptable salts. The term "pharmaceutically acceptable salt" refers to a physiologically or toxicologically tolerable salt, and when appropriate, including pharmaceutically acceptable base addition salts and acid addition salts thereof. The compounds of formula (1) of the present invention include all pharmaceutically acceptable salts thereof.

In another aspect, the compounds of formula (1) of the present invention may exist in a form of pharmaceutically acceptable nanoparticles. Nanoparticles containing a compound of formula (1) of the present invention can be designed to improve the pharmacokinetics and biodistribution of the drug. For example, a compound of formula (1) may be encased in liposomes, which may extend the life of the drug that is being distributed. Nanoparticles of suitable size may also have a better safety profile because the nanoparticles will preferentially leak out of the porous blood vessels around the tumor cells. This may further provide the benefit of lower doses of the drug.

In another aspect, the compounds of formula (1) of the present invention may exist in the form of prodrugs. The term "prodrug" refers to a compound that is converted to a compound of the present invention by a metabolic process in vivo (for example, by hydrolysis, reduction or oxidation). The compounds of formula (1) of the present invention include all such prodrugs thereof.

In another aspect, the compounds of formula (1) of the present invention also include pharmaceutically acceptable isotopic variations in which one or more atoms is replaced by atoms having the same atomic number but different atomic mass. The atoms suitable for such isotope replacement include hydrogen, carbon, nitrogen, oxygen, phosphorus, sulfur, fluorine, iodine, and chlorine. Certain isotopic variations of the compounds of formula (1), such as deuterium replaced compounds, may afford certain therapeutic advantages resulting from greater metabolic stability, and hence may be preferred in some circumstances. The isotopic variations of the compounds of formula (1) can be prepared by conventional techniques known to those skilled in the art.

The Preparation of the Triazolotriazine Derivatives

Another aspect of the present invention is the preparation of the triazolotriazine compounds as A2A receptor antagonists. The triazolotriazine compounds of the invention can be prepared by various synthetic methods. As an illustrative example, two general synthetic routes to the target Scheme 1

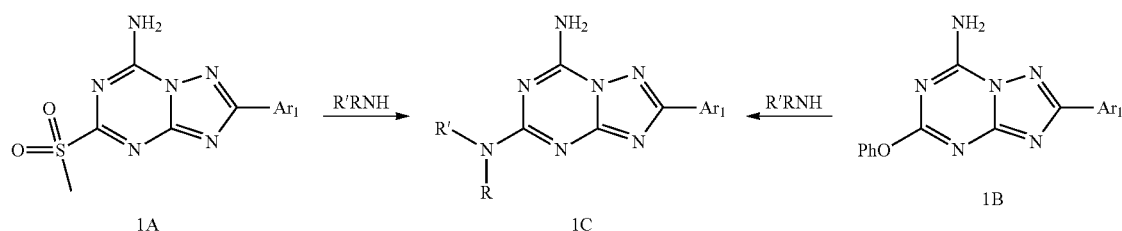

compound are shown in Scheme (1). In the first approach, after the intermediate (1A) is prepared in a suitable manner, the methylsulfonyl group of intermediate (1A) is replaced by an alkyl amino group to give the triazolotriazine compound (1C). In the second approach, after the intermediate (1B) is prepared in a suitable manner, the phenoxy group of intermediate (1B) is replaced by an alkyl amino group to give the triazolotriazine compound (1C).

The needed intermediates (1A) and (1B) in Scheme (1) can also be prepared by various synthetic methods. As an illustrative example, a general synthetic route to compound (1A) is shown in Scheme (2). In the first step, a suitable aryl hydrazide (2A) reacts with S-methylisothiourea (2B) in aqueous sodium hydroxide to give intermediate (2C). Vigorous heating of (2C) in aqueous medium in the following step provides intermediate (2D), which reacts with N-cyanodithioimino-carbonate (2E) to afford the sulfide intermediate (2F). Subsequent oxidation of intermediate (2F) with m-chloroperoxybenzoic acid provides the needed sulfone (1A). As is shown in Scheme (1), nucleophilic displacement of the methylsulfonyl group with a suitable alkyl amine gives the target compound (1C) (J. Chem. Soc., Perkin Trans. 1 1995, 801-808; Structural Chemistry. 2013, 24, 1241-1251).

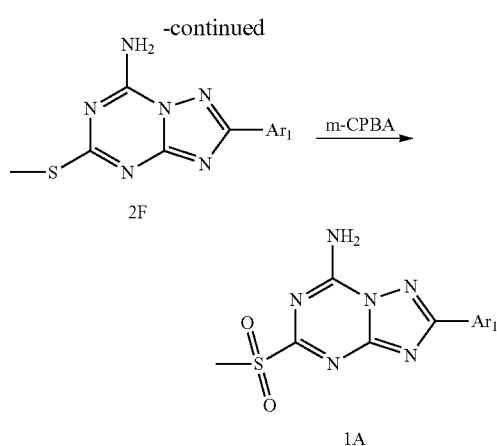

The intermediate (2D) in Scheme (2) can also be prepared by various synthetic methods. As illustrative examples, three alternative synthetic routes to intermediate (2D) are shown in Scheme (3). It is worth emphasizing that among the three approaches, the one starting from a methyl ester or ethyl ester (3F) usually improves efficiency and gives higher yield.

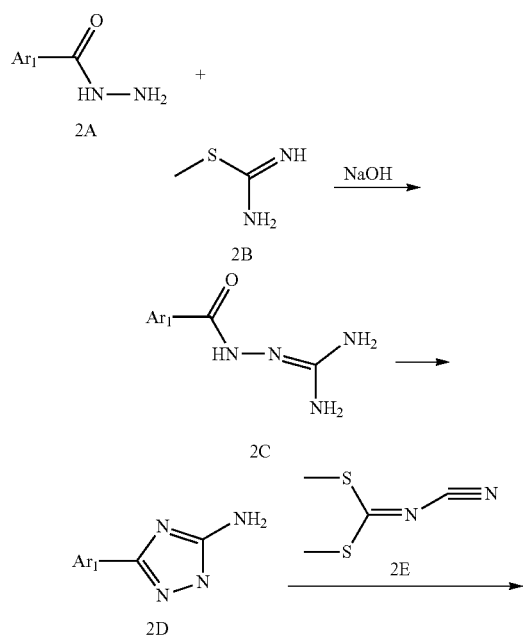

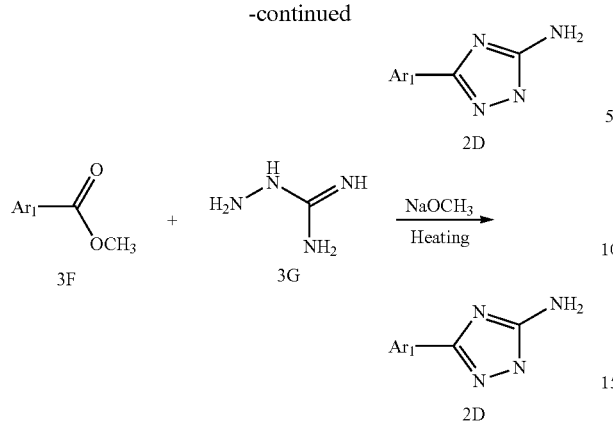

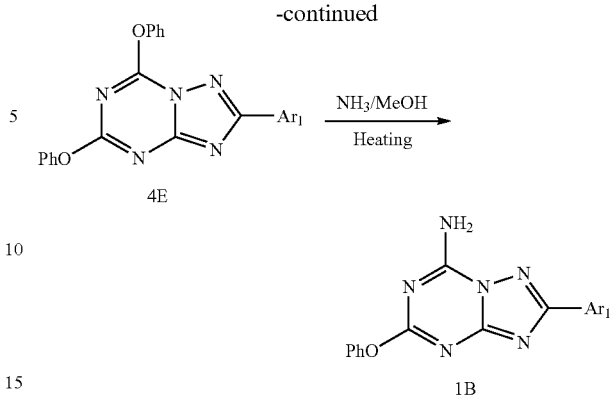

The intermediate (1B) in Scheme (1) can be prepared as shown in Scheme (4). Starting from cyanuric chloride (4A), reflux in phenol provides 2,4,6-triphenoxy-1,3,5-triazine (4B). The following reaction with hydrazine hydrate gives 2-hydrazino-4,6-diphenoxy-1,3,5-triazine (4C), which upon reacting with suitable acid chloride gives the acyl hydrazides (4D). Cyclization of the hydrazide (4D) under dehydrative conditions provides the 2-substituted 5,7-diphenoxytriazolotriazine (4E), which can be converted into the key intermediate (1B) in refluxing methanolic ammonia (J. Chem. Soc., Perkin Trans. 1 1995, 801-808). The target compound (1C) is obtained by reacting compound (1B) with a suitable alkyl amine, as shown in Scheme (1).

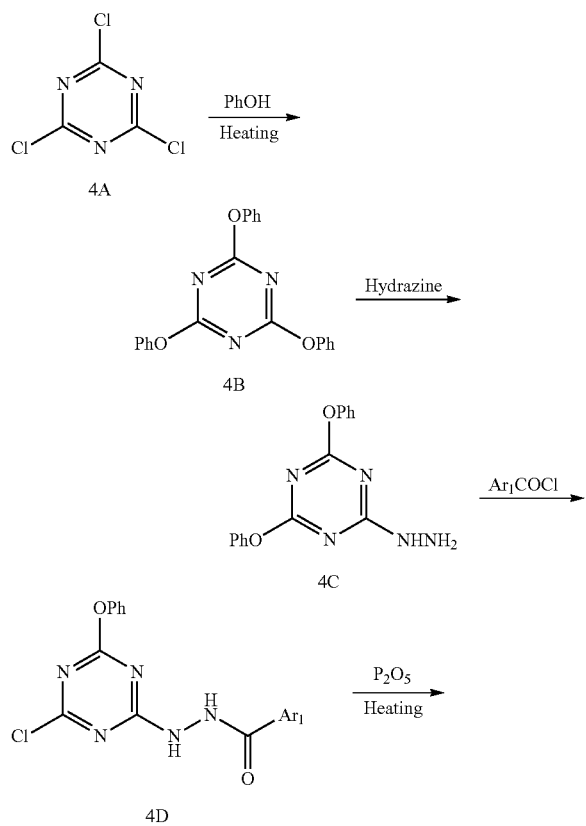

Cancer Treatment

The triazolotriazine derivatives of the present invention are adenosine A2AR antagonists and can be used for the treatment or prevention of disorders related to hyperactive adenosine A2A receptors. For example, Parkinson's disease, cognitive or memory impairment disorder, and Alzheimer's disease are some of the disorders that can be treated with the triazolotriazine derivatives of the present invention.

In particular, the A2AR antagonists of the present invention can be used for the treatment or prevention of cancer and related abnormal cell proliferations in a host, which is any multi-cellular vertebrate organism including both human and non-human mammals. The host is in particular human.

The importance of lymphoid cells in tumor immunity is well appreciated in recent years. The immune response to tumors includes immunologic surveillance, by which cellular mechanisms associated with cell-mediated immunity destroy newly transformed tumor cells after recognizing tumor-associated antigens. The cytotoxic immune cells, which are mainly T-cells, have been found within neuroblastoma, malignant melanomas, sarcomas, and carcinomas of the colon, breast, cervix, endometrium, ovary, testis, nasopharynx, and kidney. Antibody-mediated protection against tumor growth is also known, although it generally plays a less significant role than cell-mediated immunity against cancer.

The A2AR antagonists of the present invention can be used to increase the anti-tumor activity of immune cells in a host. The A2AR antagonists can reduce T cell anergy or the tolerance of T cells to cancer, can increase susceptibility of cancer cells to immune rejection, can inhibit the expansion of regulatory T cells, and can enhance the generation of memory T cells. The A2AR antagonists can improve both the natural immune response and various adaptive immunotherapy in a host.

In a typical embodiment of the present invention, a method of treating or preventing abnormal cell proliferation comprises administering to a patient an effective dose of an A2AR antagonist of formula (1), or a pharmaceutically acceptable salt or solvate thereof.

To be more effective, a synergistic effect may be achieved by combining the A2AR antagonists of the present invention with other modalities of cancer therapy, such as chemotherapy, tumor vaccines, and various immune checkpoint inhibitors. The term "combination therapy" refers to both concurrent and sequential administration of the active agents.

As an example of the combination therapy, a method of treating or preventing abnormal cell proliferation in a host comprises administering to a patient an A2AR antagonist of formula (1) in combination or alternation with an immune checkpoint inhibitor. The immune checkpoint inhibitor can be a PD-1 inhibitor, a PD-L1 inhibitor, a PD-L2 inhibitor, a CTLA-4 inhibitor, a BTLA inhibitor, a LAG3 inhibitor, a TIM-3 inhibitor, a B7-H3 inhibitor, a B7-H4 inhibitor, a KIR inhibitor, a TIGIT inhibitor, or a VISTA inhibitor.

In another example, a method of treating or preventing abnormal cell proliferation in a host comprises administering to a patient an A2AR antagonist of formula (1) in combination or alternation with a cell-based vaccine. The cell-based vaccine is based on cells that match the tumor to be prevented. For example, if a host is suffering from, or at risk of suffering from, a prostate cancer, the cell-based vaccine will be based on a prostate cancer tumor cell. In these instances, the cell is typically irradiated or otherwise prevented from replicating. Or, the cell is genetically modified to secrete a colony stimulating factor.

In another example, a method of treating or preventing abnormal cell proliferation in a host comprises administering to a patient an A2AR antagonist of formula (1) in combination or alternation with Chimeric Antigen Receptor (CAR) T-Cell Therapy.

In another example, a method of treating or preventing abnormal cell proliferation in a host comprises administering to a patient an A2AR antagonist of formula (1) in combination or alternation with an anti-cancer agent to treat abnormal cell proliferation. The anti-cancer agent can be an alkylating agent, an antimetabolite, an anthracycline derivative, a plant alkaloid, a topoisomerase inhibitor, an antitumor antibiotic, a kinase inhibitor, or a monoclonal antibody against tumor antigens.

In other examples, a synergistic effect may be achieved by combining the A2AR antagonists of the present invention with two or more other modalities of cancer therapy, such as chemotherapy, tumor vaccines, and immune checkpoint inhibitors. The term "combination therapy" refers to both concurrent and sequential administration of the active agents.

Pharmaceutical Compositions

The triazolotriazine derivatives of the present invention can be formulated as pharmaceutical compositions when administered to a host. The pharmaceutical compositions are determined by the chosen route of administration, such as orally, parenterally, intravenously, intramuscularly, nasally, buccally, topically, transdermally or subcutaneously. The triazolotriazine derivatives included in the pharmaceutical compositions should be sufficient to deliver a therapeutically effective amount to treat cancer or other disorders characterized by abnormal cell proliferation without causing serious toxic effects to the host. The treatment can involve daily or multi-daily administration of the triazolotriazine derivatives over a period of a few days to weeks, months, or even years.

A convenient mode of administration of the triazolotriazine derivatives of the present invention is oral. Oral compositions generally include an inert diluent or an edible carrier. The compositions may be enclosed in gelatin capsules or compressed into tablets. The tablets, pills, capsules, troches and the like can contain any of the following ingredients: a binder such as microcrystalline cellulose, gum tragacanth or gelatin; an excipient such as starch or lactose; a disintegrating agent such as alginic acid or corn starch; a lubricant such as magnesium stearate; a glidant such as colloidal silicon dioxide; a sweetening agent such as sucrose or saccharin; a flavoring agent such as peppermint, methyl salicylate, or orange flavoring; a wetting or emulsifying agent; preservatives; and pH buffering agents and the like, for example sodium acetate or sorbitan monolaurate. When the pharmaceutical compositions are in a capsule, a liquid carrier such as fatty oil may also be included. In addition, the pharmaceutical compositions can contain various other materials, such as coatings of sugar, shellac, or other enteric agents.

The triazolotriazine derivatives of the present invention can also be administered as a component of an elixir, suspension, syrup, wafer, chewing gum or the like. A syrup may contain, in addition to the triazolotriazine derivatives, sucrose as a sweetening agent, preservatives, coloring agents and flavoring agents. Solutions or suspensions used for parenteral, intradermal, subcutaneous, or topical application can include a sterile diluent such as water, saline solution, Ringer's solution, fixed oils, polyethylene glycols, glycerin, propylene glycol, fatty acids such as oleic acid and its glyceride derivatives, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The triazolotriazine derivatives of the present invention can also be placed in carriers that protect the derivatives against rapid elimination from the body. Various means to achieve controlled release, including implants and microencapsulated delivery systems, can also be used.

The triazolotriazine derivatives of the present invention can also be administered through the use of nebulizer, a dry powder inhaler or a metered dose inhaler inhaled through the nasal aerosols.

The compositions may be prepared as solutions in saline, employing benzyl alcohol or other suitable preservatives, absorption promoters, fluorocarbons, and other conventional solubilizing or dispersing agents.

It is understandable that for any particular patient the specific dose and treatment regimen will depend upon a variety of factors including the activity of the specific compound employed, the age, body weight, general health, and sex of the patient, diet, time of administration, rate of excretion, the pathological condition to be treated, the goal of treatment, as well as the judgment of the physician. The amount of active ingredient may also depend on what is the co-administered therapeutic agent if it is a combination therapy.

EXAMPLES

The following examples, which are for detailed illustration only, are not intended to limit the scope of the present invention.

Example 1

2-(Furan-2-carboxamido) guanidine

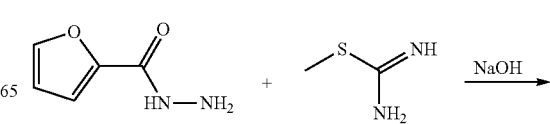

-continued

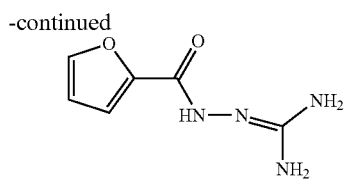

A mixture of furan-2-carbohydrazide (37.80 g, 300 mmol), S-methylisothiourea sulfate (41.70 g, 150 mmol) and an aqueous sodium hydroxide solution (2%, 1.2 L) was stirred at room temperature for 72 h. The precipitate was filtered, washed with ice-cold water, and used in the next step without further purification (25.25 g, 51.00% yield). $^1$H NMR (500 MHz, DMSO-d6) δ: 10.95 (s, 1H), 7.56 (s, 1H), 6.91 (d, J=91.9 Hz, 4H), 6.64 (s, 1H), 6.45 (s, 1H).

Example 2

3-(Furan-2-yl)-1H-1,2,4-triazol-5-amine

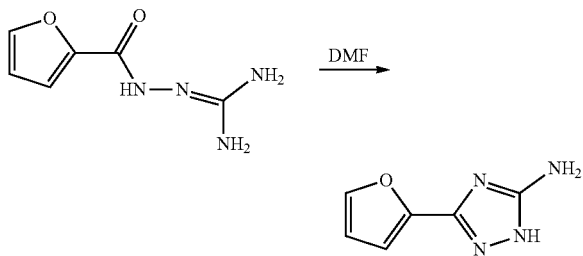

A stirred solution of 2-(furan-2-carboxamido) guanidine (23.20 g, 138 mmol) in DMF (464 mL) was heated at 125° C. overnight. After it was cooled to room temperature, the solvent was removed under reduced pressure. To the residue was added DCM (200 ml) and it was stirred for 30 min. The precipitate was filtered and washed with DCM (20 mL×2) to afford the title compound as yellow solid (17.37 g, 84.00% yield). $^1$H NMR (500 MHz, DMSO-d6) δ: 12.13 (s, 1H), 7.69 (s, 1H), 6.69 (d, J=1.8 Hz, 1H), 6.54 (dd, J=3.0, 1.7 Hz, 1H), 6.03 (s, 2H).

Example 2A 3-(Furan-2-yl)-1H-1,2,4-triazol-5-amine

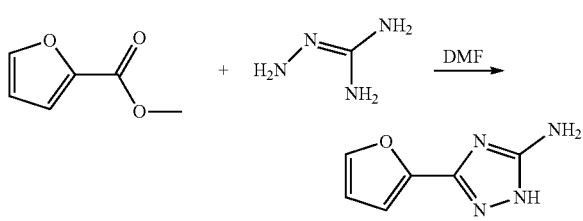

To a stirred solution of CH$_3$ONa (171.4 g, 3172 mol) and aminoguanidine hydrochloride (175.3 g, 1586 mmol) in methanol (1200 mL) at 0° C. was added slowly the solution of methyl furan-2-carboxylate (100 g, 793 mmol) in methanol (300 mL). The reaction mixture was then stirred at 75° C. overnight. The resulting mixture was filtered. The filtrate was concentrated in vacuo and the residue was dissolved in water (50 mL). 3N HCl was added to adjust pH to 4. The precipitated solid was collected by filtration and drying to afford the title compound as yellow solid (69.2 g, 58.1% yield). $^1$H NMR (500 MHz, DMSO-d6) δ: 12.44 (s, 1H), 7.69 (d, 1H), 6.70 (d, 1H), 6.54 (dd, 1H), 6.03 (s, 2H).

Example 3

2-(Furan-2-yl)-5-(methylthio)-[1,2,4]triazolo[1,5-a][1,3,5]triazin-7-amine

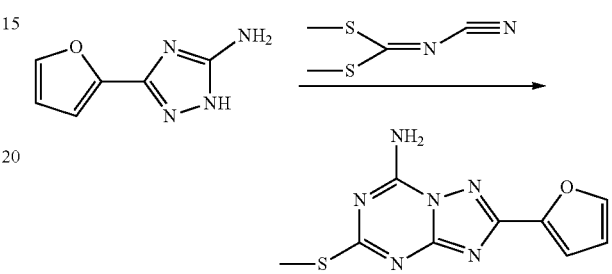

A mixture of 3-(furan-2-yl)-1H-1,2,4-triazol-5-amine (13.58 g, 90.46 mmol) and dimethyl cyanocarbonimidodithioate (13.23 g, 90.46 mmol) was stirred at 180° C. for 1.5 h. It was next cooled to room temperature. The residue was purified by column chromatography (PE:EA=1:1) afforded the title compound as white solid (7.00 g, 31.20% yield). $^1$H NMR (500 MHz, DMSO-d6) δ: 8.96 (s, 1H), 8.76 (s, 1H), 7.93 (d, J=0.9 Hz, 1H), 7.16 (d, J=3.3 Hz, 1H), 6.72 (dd, J=3.4, 1.7 Hz, 1H), 2.51 (s, 3H).

Example 4

2-(Furan-2-yl)-5-(methylsulfonyl)-[1,2,4]triazolo[1,5-a][1,3,5]triazin-7-amine

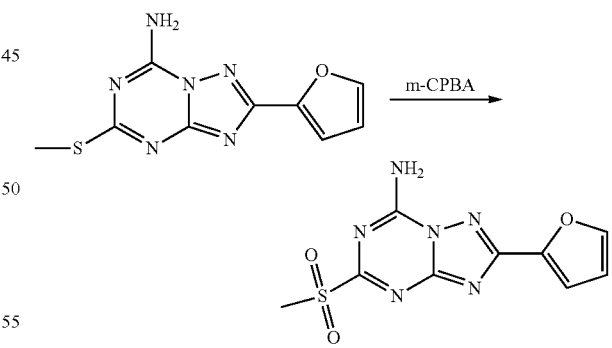

A solution of m-CPBA (85% strength, 26.20 g, 128.90 mmol) in DCM (240 mL) was added dropwise to a stirred, ice-cold suspension of 2-(furan-2-yl)-5-(methylthio)-[1,2,4]triazolo[1,5-a][1,3,5]triazin-7-amine (8.0 g, 32.2 mmol) in DCM (480 mL). The reaction was stirred at room temperature for 22 h before the solvent was removed under vacuum. The crude material was suspended in ethanol (120 mL) and stirred at room temperature for 30 min. The solid was filtered, washed with ethanol and dried to give the title compound as brown solid (7.82 g, 86.90% yield). $^1$H NMR (500 MHz, DMSO-d6) δ: 9.81 (s, 1H), 9.48 (s, 1H), 7.99 (d, J=1.0 Hz, 1H), 7.27 (d, J=3.4 Hz, 1H), 6.76 (dd, J=3.4, 1.8 Hz, 1H), 3.36 (s, 3H).

Example 5

2-(Furan-2-yl)-N5-(2-(pyridin-4-yl)ethyl)-[1,2,4]triazolo[1,5-a][1,3,5]triazine-5,7-diamine

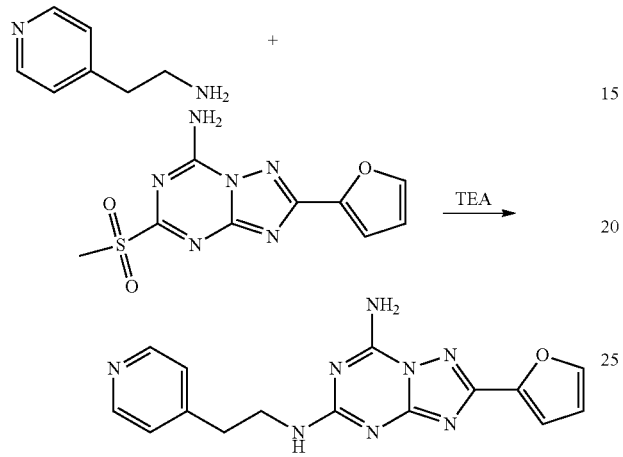

A solution of 2-(pyridin-4-yl)ethanamine (100 mg, 0.86 mmol), 2-(furan-2-yl)-5-(methylsulfonyl)-[1,2,4]triazolo[1,5-α][1,3,5]triazin-7-amine (230 mg, 0.82 mmol) and TEA (250 mg, 2.46 mmol) in MeCN (5 mL) was stirred overnight. The reaction mixture was quenched with water (30 mL) and extracted with DCM (15 mL×3). The organic layer was washed with water and brine, dried over sodium sulfate and concentrated in vacuo. The crude product was purified by column chromatography to afford the title compound as white solid (41.50 mg, 15.72% yield). $^1$H NMR (500 MHz, DMSO-d6) δ: 8.47 (d, J=4.5 Hz, 2H), 8.22 (s, 2H), 7.89 (d, J=14.3 Hz, 1H), 7.57 (d, J=46.0 Hz, 1H), 7.28 (s, 2H), 7.06 (s, 1H), 6.68 (s, 1H), 3.54 (d, J=5.6 Hz, 2H), 2.90 (s, 2H).

Example 6

Methyl 4-(2-aminoethyl)benzoate

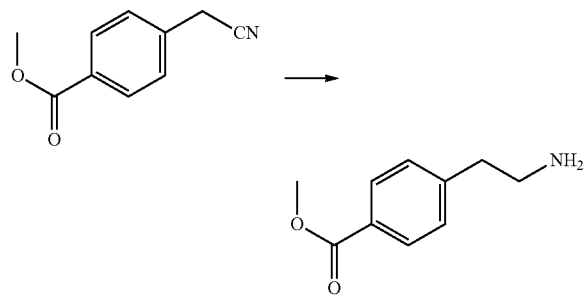

A stirred mixture of methyl 4-(cyanomethyl)benzoate (2 g, 11.42 mmol), NH$_3$/MeOH (7N, 4 mL) and Raney-Nickel (0.1 g) in MeOH (20 mL) was heated under H$_2$ at 55° C. overnight. The reaction mixture was filtered through Celite, the filtrate was concentrated, and purification by column chromatography (EtOAc/MeOH) afforded the title compound as brown oil (1.35 g, 66.0% yield). $^1$H NMR (500 MHz, DMSO-d6) δ: 7.97-7.76 (m, 2H), 7.35 (d, J=8.2 Hz, 2H), 3.84 (s, 3H), 2.84-2.74 (m, 2H), 2.71 (t, J=6.9 Hz, 2H).

Example 7

Methyl 4-(2-(tert-butoxycarbonyl)aminoethyl)benzoate

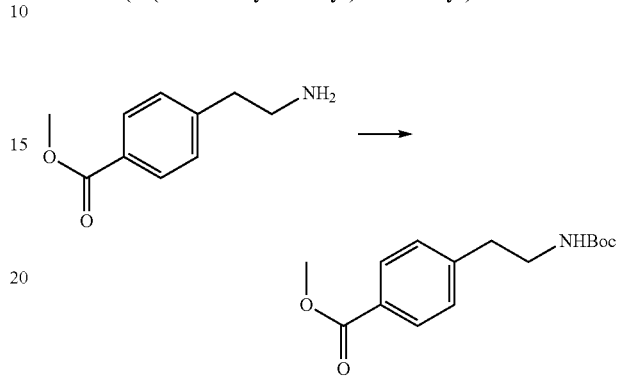

To a stirred solution of methyl 4-(2-aminoethyl)benzoate (4.5 g, 25 mmol) in THF (15 mL) was added TEA (7.6 g, 75 mmol) and Boc$_2$O (6.0 g, 27 mmol). The reaction mixture was stirred at room temperature overnight. TLC showed the reaction completed. The reaction mixture was concentrated in vacuo. The crude product was purified by column chromatography to afford the title compound as yellow solid (5.6 g, 80% yield). $^1$H NMR (500 MHz, CDCl$_3$) δ: 7.97 (d, 2H), 7.26 (d, 2H), 4.54 (dr, 1H), 3.90 (s, 3H), 3.38-3.40 (m, 2H), 2.86 (t, 2H), 1.43 (s, 9H).

Example 8

4-(2-((tert-Butoxycarbonyl)amino)ethyl)benzoic acid

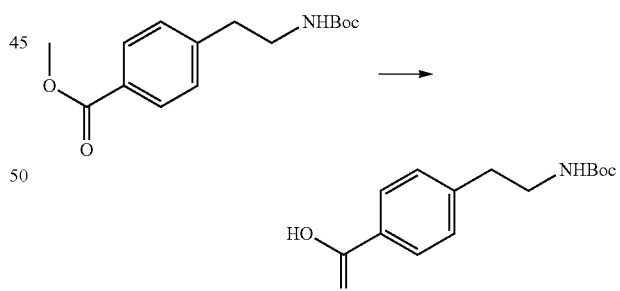

To a stirred solution of methyl 4-(2-(tert-butoxycarbonyl)aminoethyl)benzoate (5.6 g, 0.20 mmol) in THF (50 mL) and H$_2$O (50 mL) was added sodium hydroxide (8.0 g, 2.0 mmol). The reaction mixture was stirred at 50° C. overnight. TLC showed the reaction completed. The reaction mixture was neutralized with 2N HCl and extracted with EtOAc. The organic layer was washed with water and brine, dried over sodium sulfate and concentrated in vacuo to afford the title compound as white solid (5.1 g, 96% yield). $^1$H NMR (500 MHz, DMSO-d6) δ: 7.84 (d, 2H), 7.26 (d, 2H), 6.88 (t, 1H), 3.14-3.17 (m, 2H), 2.74 (t, 2H), 1.36 (s, 9H).

Example 9 tert-Butyl 4-((2-(pyrrolidin-1-yl)ethyl)carbamoyl)phenethylcarbamate

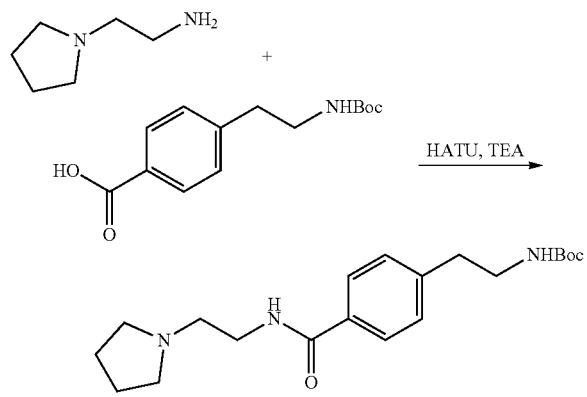

A mixture of 4-(2-((tert-Butoxycarbonyl)amino)ethyl) benzoic acid (0.265 g, 1 mmol), HATU (0.494 g, 1.3 mmol) and TEA (0.202 g, 2 mmol) in dichloromethane (20 mL) was stirred at room temperature for 30 min. Then 2-(pyrrolidin-1-yl)ethanamine (0.126 g, 1.1 mmol) was added and the reaction was stirred at room temperature for 2 h. After more dichloromethane (80 mL) was added, the reaction mixture washed with water (2×20 mL). After drying with $Na_2SO_4$, removal of the solvent provided the crude product. Purification by column chromatography afforded the title compound as white solid (0.337 g, 93.2% yield). $^1$H NMR (500 MHz, DMSO-d6) δ: 8.47 (s, 1H), 7.78 (d, J=8.2 Hz, 2H), 7.29 (d, J=8.1 Hz, 2H), 6.88 (t, J=5.3 Hz, 1H), 3.51-3.42 (m, 2H), 3.18-3.13 (m, 2H), 2.94 (br, 5H), 2.74 (t, J=7.4 Hz, 2H), 2.69 (s, 1H), 1.81 (s, 4H), 1.36 (s, 9H).

Example 10

4-(2-Aminoethyl)-N-(2-(pyrrolidin-1-yl)ethyl)benzamide

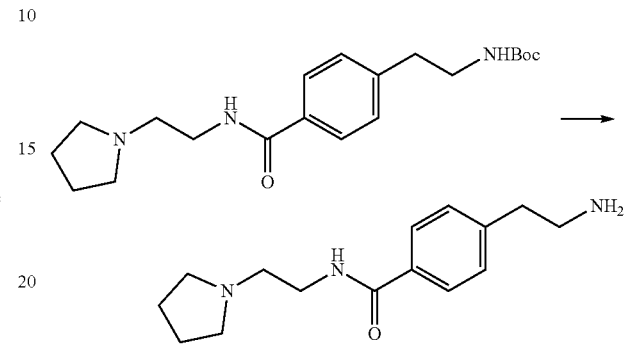

Hydrochloric acid (20%, 2 mL) was added to a stirred solution of tert-butyl 4-((2-(pyrrolidin-1-yl)ethyl)carbamoyl)phenethylcarbamate (0.3 g, 0.83 mmol) in methanol (5 mL). After it was stirred at 30° C. for 17 h, the excess solvent was removed under reduced pressure to afford the product, which was used for the next step directly.

Example 11

4-(2-((7-Amino-2-(furan-2-yl)-[1,2,4]triazolo[1,5-a][1,3,5]triazin-5-yl)amino)ethyl)-N-(2-(pyrrolidin-1-yl)ethyl)benzamide

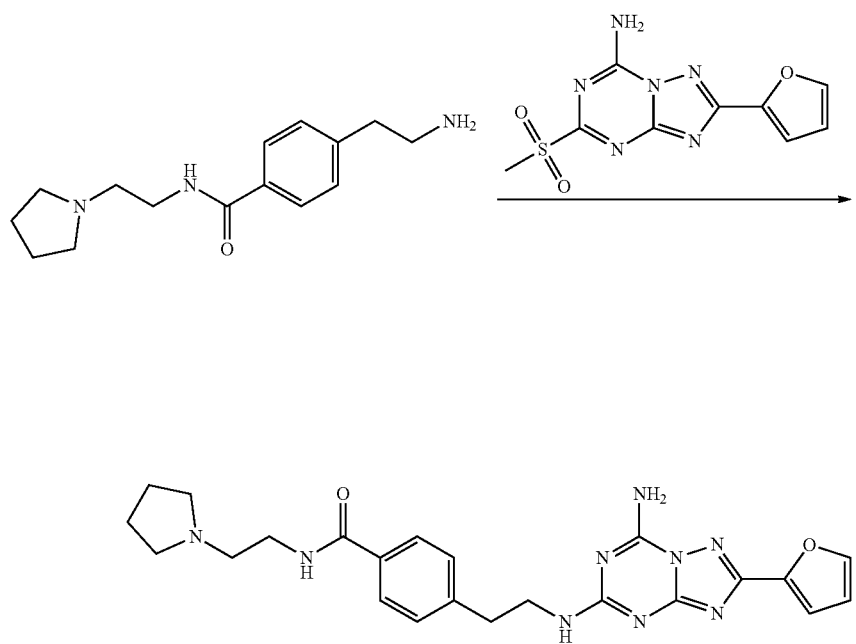

The reaction was carried out as in Example 5 to afford the title compound as light-yellow solid (13.1% yield). LC-MS m/z [M+H]+: 462; 1H NMR (500 MHz, DMSO-d6) δ: 8.37 (s, 1H), 8.15 (s, 2H), 7.87 (s, 1H), 7.78 (d, J=7.7 Hz, 2H), 7.53 (d, J=40.6 Hz, 1H), 7.33 (d, J=7.4 Hz, 2H), 7.06 (d, J=2.9 Hz, 1H), 6.67 (s, 1H), 3.51 (d, J=5.1 Hz, 2H), 3.38 (d, J=6.0 Hz, 2H), 2.91 (d, J=6.7 Hz, 2H), 2.61 (s, 2H), 2.54 (s, 4H), 1.69 (s, 4H).

Example 12

4-(2-((7-Amino-2-(furan-2-yl)-[1,2,4]triazolo[1,5-a][1,3,5]triazin-5-yl)amino)ethyl)-N-(2-morpholino-ethyl)benzamide

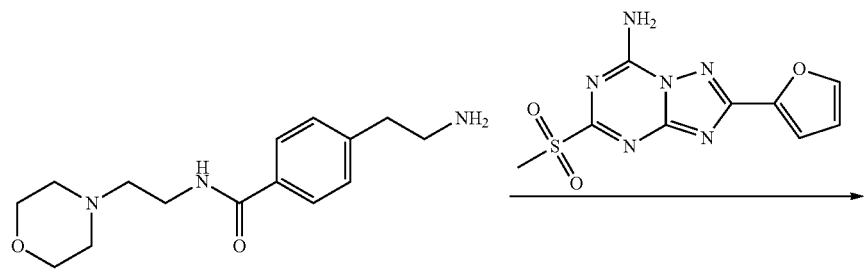

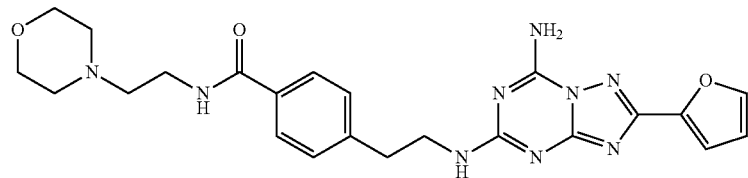

The title compound was synthesized in a similar way as the title compound in Example 11. LC-MS m/z [M+H]+: 478; 1H NMR (500 MHz, DMSO-d6) δ: 8.33 (t, J=5.5 Hz, 1H), 8.18 (s, 2H), 7.87 (s, 1H), 7.77 (d, J=7.9 Hz, 2H), 7.54 (d, J=42.0 Hz, 1H), 7.34 (d, J=7.8 Hz, 2H), 7.06 (d, J=3.2 Hz, 1H), 6.67 (s, 1H), 3.59-3.48 (m, 6H), 3.37 (dd, J=13.0, 6.5 Hz, 2H), 2.91 (t, J=7.1 Hz, 2H), 2.44 (dd, J=18.0, 11.1 Hz, 6H).

Example 13

4-(2-((7-Amino-2-(furan-2-yl)-[1,2,4]triazolo[1,5-a][1,3,5]triazin-5-yl)amino)ethyl)-N-(2-(4-methylpiperazin-1-yl)ethyl)benzamide

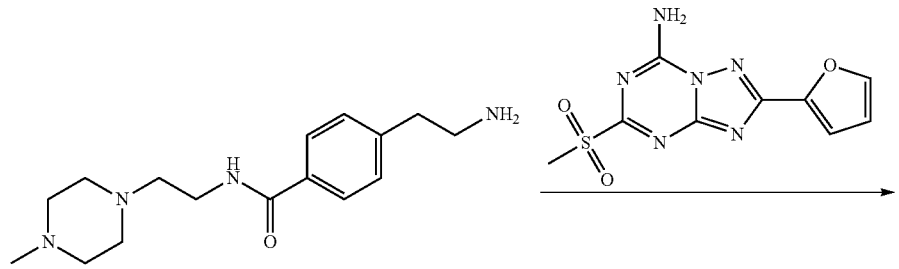

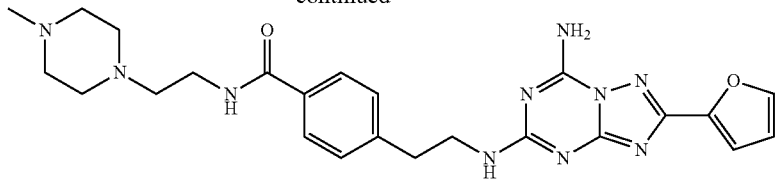

The title compound was synthesized in a similar way as the title compound in Example 11. LC-MS m/z [M+H]+: 491; ¹H NMR (500 MHz, DMSO-d6) δ: 8.42 (s, 1H), 8.18 (s, 2H), 7.87 (s, 1H), 7.79 (d, J=8.1 Hz, 2H), 7.60-7.47 (m, 1H), 7.34 (d, J=7.9 Hz, 2H), 7.06 (d, J=3.3 Hz, 1H), 6.68 (d, J=1.6 Hz, 1H), 4.11 (s, 1H), 3.52 (d, J=5.6 Hz, 2H), 3.39 (s, 2H), 3.17 (s, 3H), 2.92 (dd, J=8.3, 6.3 Hz, 5H), 2.57 (s, 4H).

Example 14

(4-(2-((7-Amino-2-(furan-2-yl)-[1,2,4]triazolo[1,5-a][1,3,5]triazin-5-yl)amino)ethyl)phenyl)-(4-(2,2,2-trifluoroethyl)piperazin-1-yl)methanone

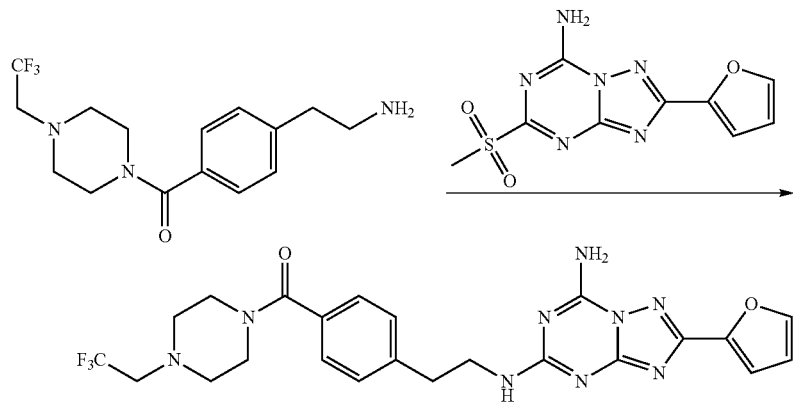

The title compound was synthesized in a similar way as the title compound in Example 11. LC-MS m/z [M+H]+: 516; ¹H NMR (500 MHz, DMSO-d6) δ: 8.15 (br, 2H), 7.96-7.85 (m, 1H), 7.64-7.47 (m, 1H), 7.30 (d, J=8.9 Hz, 4H), 7.06 (d, J=3.1 Hz, 1H), 6.67 (s, 1H), 3.52 (d, J=6.1 Hz, 4H), 3.44-3.31 (m, 2H), 3.20 (q, J=10.1 Hz, 2H), 2.90 (t, J=7.0 Hz, 2H), 2.61 (br, 4H).

Example 15

4-(2-((7-Amino-2-(furan-2-yl)-[1,2,4]triazolo[1,5-a][1,3,5]triazin-5-yl)amino)ethyl)-N-(3-(dimethylamino)propyl)benzamide

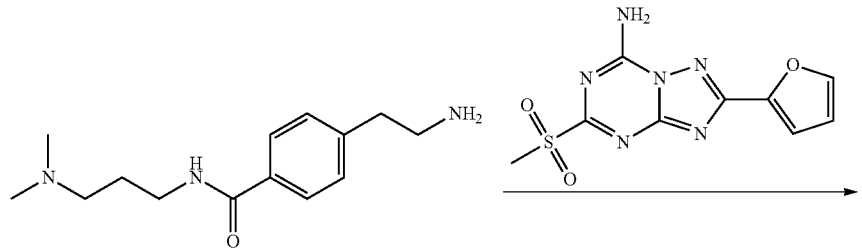

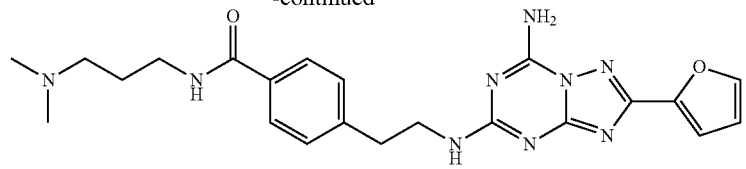

The title compound was synthesized in a similar way as the title compound in Example 11. ¹H NMR (500 MHz, DMSO-d6) δ: 8.44 (t, J=5.3 Hz, 1H), 8.15 (br, 2H), 7.87 (s, 1H), 7.77 (d, J=8.0 Hz, 2H), 7.51 (dd, J=25.9, 20.8 Hz, 1H), 7.34 (d, J=7.7 Hz, 2H), 7.06 (d, J=3.2 Hz, 1H), 6.67 (s, 1H), 3.52 (d, J=6.0 Hz, 2H), 3.27 (dd, J=12.8, 6.7 Hz, 2H), 2.92 (t, J=7.1 Hz, 2H), 2.29 (t, J=7.0 Hz, 2H), 2.16 (s, 6H), 1.74-1.59 (m, 2H).

Example 16

(4-(2-((7-Amino-2-(furan-2-yl)-[1,2,4]triazolo[1,5-a][1,3,5]triazin-5-yl)amino)ethyl)phenyl)-(4,4-difluoropiperidin-1-yl)methanone

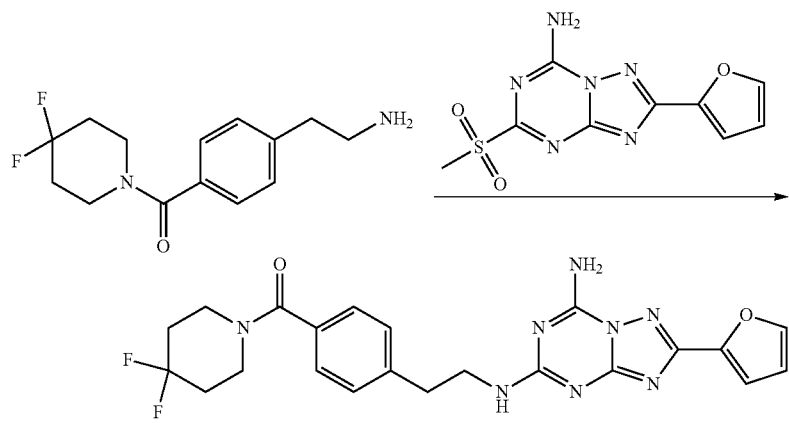

The title compound was synthesized in a similar way as the title compound in Example 11. ¹H NMR (500 MHz, DMSO-d6) δ: 8.31 (br, 2H), 7.87 (s, 1H), 7.56 (dt, J=41.0, 5.5 Hz, 1H), 7.40-7.29 (m, 4H), 7.05 (d, J=3.3 Hz, 1H), 6.68 (dd, J=3.1, 1.6 Hz, 1H), 3.82-3.38 (m, 6H), 2.90 (t, J=7.3 Hz, 2H), 2.03 (m, 4H).

Example 17

(4-(2-((7-Amino-2-(furan-2-yl)-[1,2,4]triazolo[1,5-a][1,3,5]triazin-5-yl)amino)ethyl)phenyl)-(4-fluoropiperidin-1-yl)methanone

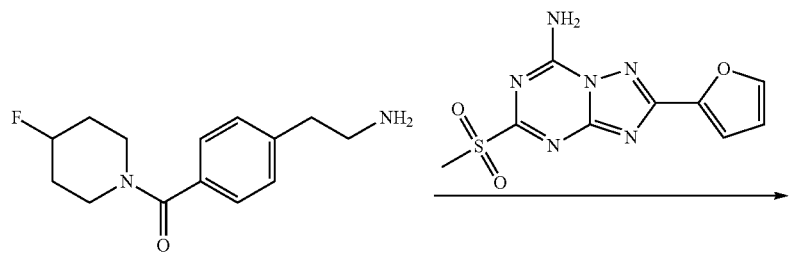

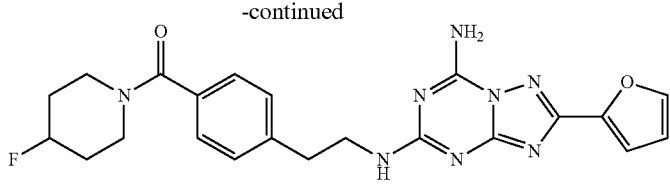

The title compound was synthesized in a similar way as the title compound in Example 11. LC-MS m/z [M+H]⁺: 451; ¹H NMR (500 MHz, DMSO-d6) δ: 8.32 (br, J=115.2 Hz, 2H), 7.87 (s, 1H), 7.66-7.47 (m, 1H), 7.40-7.26 (m, 4H), 7.06 (d, J=3.3 Hz, 1H), 6.77-6.59 (m, 1H), 4.89 (dd, J=48.3, 3.0 Hz, 1H), 3.79-3.34 (m, 6H), 2.89 (dd, J=15.3, 8.0 Hz, 2H), 1.95-1.58 (m, 4H).

Example 18

(4-(2-((7-Amino-2-(furan-2-yl)-[1,2,4]triazolo[1,5-a][1,3,5]triazin-5-yl)amino)ethyl)phenyl)-(morpholino)methanone

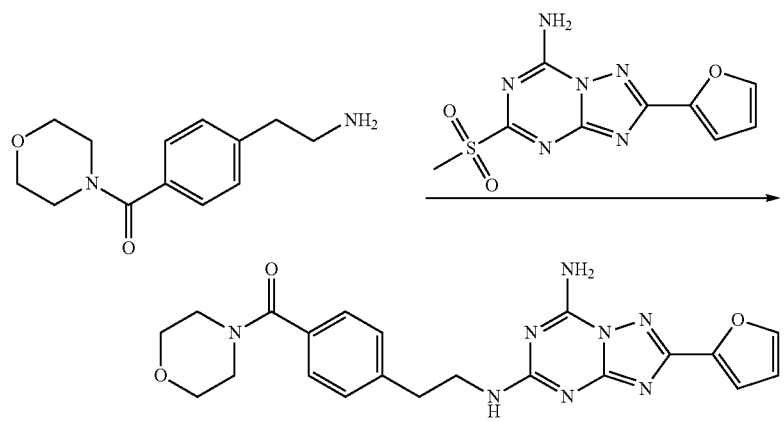

The title compound was synthesized in a similar way as the title compound in Example 11. ¹H NMR (500 MHz, DMSO-d6) δ: 8.32 (br, 2H), 7.92-7.85 (m, 1H), 7.54 (dd, J=26.6, 20.9 Hz, 1H), 7.33 (s, 4H), 7.06 (d, J=3.1 Hz, 1H), 6.68 (s, 1H), 3.74-3.38 (m, 10H), 2.90 (t, J=7.2 Hz, 2H).

Example 19

(4-(2-((7-Amino-2-(furan-2-yl)-[1,2,4]triazolo[1,5-a][1,3,5]triazin-5-yl)amino)ethyl)phenyl)-(pyrrolidin-1-yl)methanone

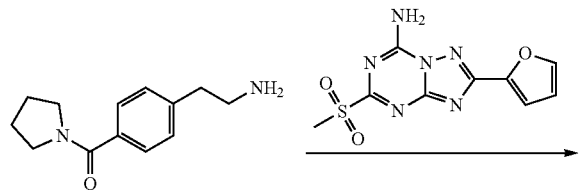

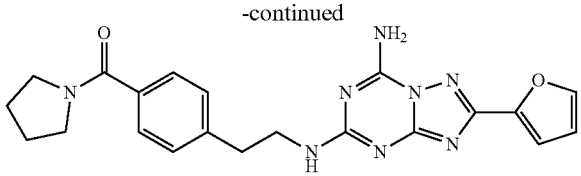

The title compound was synthesized in a similar way as the title compound in Example 11. ¹H NMR (500 MHz, DMSO-d6) δ: 8.31 (br, 2H), 7.87 (s, 1H), 7.52 (dd, J=26.3, 20.9 Hz, 1H), 7.44 (d, J=7.9 Hz, 2H), 7.30 (d, J=7.7 Hz, 2H), 7.06 (d, J=3.2 Hz, 1H), 6.68 (s, 1H), 3.52 (d, J=6.3 Hz, 2H), 3.44 (t, J=6.7 Hz, 2H), 3.35 (d, J=6.6 Hz, 2H), 2.90 (t, J=7.0 Hz, 2H), 1.89-1.72 (m, 4H).

Example 20

(4-(2-((7-Amino-2-(furan-2-yl)-[1,2,4]triazolo[1,5-a][1,3,5]triazin-5-yl)amino)ethyl)phenyl)-(4-methylpiperazin-1-yl)methanone

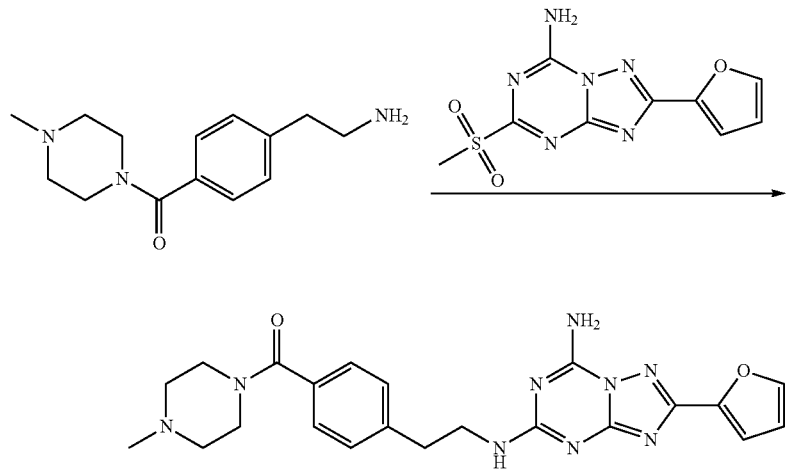

The title compound was synthesized in a similar way as the title compound in Example 11. $^1$H NMR (500 MHz, DMSO-d6) δ: 8.26 (d, J=125.8 Hz, 2H), 7.86 (s, 1H), 7.52 (s, 1H), 7.30 (br, 4H), 7.05 (s, 1H), 6.67 (s, 1H), 3.53 (br, 4H), 3.31 (br, 2H), 2.89 (br, 2H), 2.27 (br, 4H), 2.16 (s, 3H).

Example 21

(S)-(4-(2-((7-Amino-2-(furan-2-yl)-[1,2,4]triazolo[1,5-a][1,3,5]triazin-5-yl)amino)ethyl)-phenyl)(3-fluoropyrrolidin-1-yl)methanone

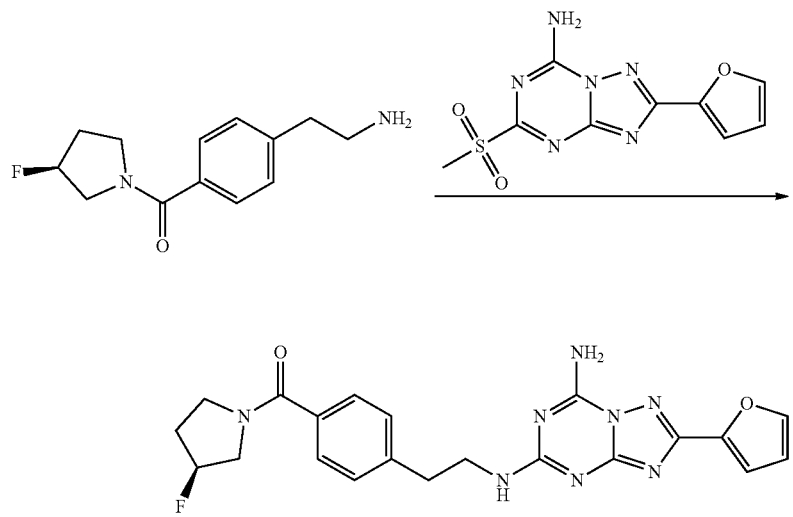

The title compound was synthesized in a similar way as the title compound in Example 11. $^1$H NMR (500 MHz, DMSO-d6) δ: 8.28 (br, 2H), 7.86 (s, 1H), 7.63-7.43 (m, 3H), 7.32 (d, J=7.7 Hz, 2H), 7.06 (d, J=3.3 Hz, 1H), 6.67 (s, 1H), 5.31 (t, J=52.7 Hz, 1H), 3.82-3.63 (m, 2H), 3.58-3.41 (m, 4H), 2.91 (t, J=7.0 Hz, 2H), 2.19-1.99 (m, 2H).

Example 22

4-(2-((7-Amino-2-(furan-2-yl)-[1,2,4]triazolo[1,5-a][1,3,5]triazin-5-yl)amino)ethyl)-N-(2-(azetidin-1-yl)ethyl)benzamide

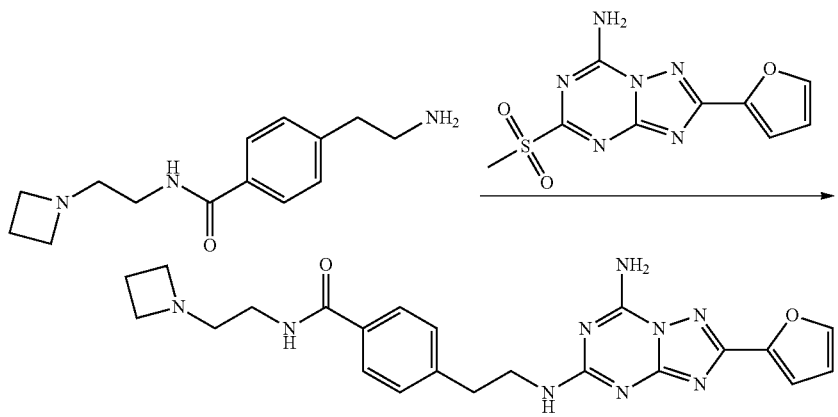

The title compound was synthesized in a similar way as the title compound in Example 11. ¹H NMR (500 MHz, DMSO-d6) δ: 8.30-8.13 (m, 3H), 7.87 (s, 1H), 7.77 (d, J=8.0 Hz, 2H), 7.50 (dd, J=26.4, 21.0 Hz, 1H), 7.33 (d, J=7.7 Hz, 2H), 7.06 (d, J=3.3 Hz, 1H), 6.67 (s, 1H), 3.52 (d, J=6.1 Hz, 2H), 3.19 (dd, J=12.5, 6.4 Hz, 2H), 3.13 (t, J=6.9 Hz, 4H), 2.92 (t, J=7.2 Hz, 2H), 2.48 (d, J=6.7 Hz, 2H), 1.95 (p, J=6.9 Hz, 2H).

Example 23

4-(2-((7-Amino-2-(furan-2-yl)-[1,2,4]triazolo[1,5-a][1,3,5]triazin-5-yl)amino)ethyl)-N-(tert-butyl)benzamide

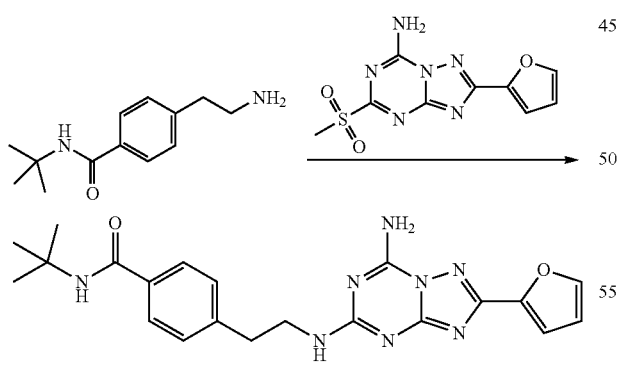

The title compound was synthesized in a similar way as the title compound in Example 11. ¹H NMR (500 MHz, DMSO-d6) δ: 8.34 (br, 2H), 7.87 (s, 1H), 7.73 (d, J=8.1 Hz, 2H), 7.67 (s, 1H), 7.54 (dt, J=40.3, 5.6 Hz, 1H), 7.31 (t, J=7.8 Hz, 2H), 7.06 (d, J=3.3 Hz, 1H), 6.68 (dd, J=3.3, 1.7 Hz, 1H), 3.50 (dd, J=13.5, 6.5 Hz, 2H), 2.90 (t, J=7.3 Hz, 2H), 1.37 (s, 9H).

Example 24

N5-(2-(1H-Benzo[d]imidazol-5-yl)ethyl)-2-(furan-2-yl)-[1,2,4]triazolo[1,5-a][1,3,5]triazine-5,7-diamine

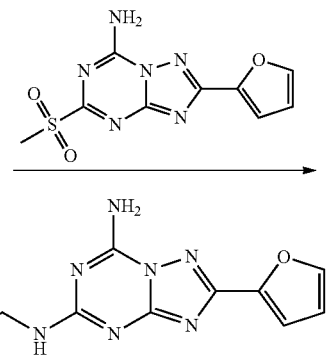

The reaction was carried out as in Example 5 to afford the title compound (0.0231 g, 12.8% yield) as white solid. LC-MS m/z [M+H]⁺: 362; ¹H NMR (500 MHz, DMSO-d6) δ: 8.86 (d, J=15.7 Hz, 1H), 8.32 (br, 2H), 7.87 (s, 1H), 7.65 (t, J=7.6 Hz, 1H), 7.58 (s, 1H), 7.51 (t, J=5.4 Hz, 1H), 7.31 (d, J=8.2 Hz, 1H), 7.06 (d, J=3.2 Hz, 1H), 6.68 (s, 1H), 3.59-3.50 (m, 2H), 3.01 (t, J=7.1 Hz, 2H).

Example 25 tert-Butyl (2-(isoquinolin-6-yl)ethyl)carbamate

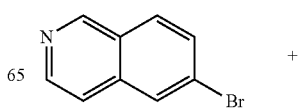

-continued

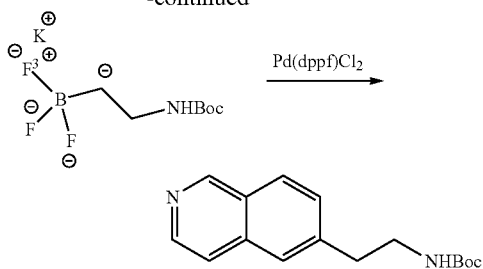

A mixture of 6-bromoisoquinoline (0.5 g, 2.4 mmol), potassium tert-butyl N-[2-(trifluoroboranuidyl)ethyl]carbamate (0.723 g, 2.88 mmol), cesium carbonate (2.346 g, 7.2 mmol) and Pd(dppf)Cl$_2$ (0.088 g, 0.12 mmol) in toluene (12 mL) and water (4 mL) was stirred under N$_2$ at 80° C. overnight. The reaction mixture was filtered through Celite and water (30 mL) was added to the filtrate. The filtrate was extracted with ethyl acetate (30 mL×2). The organic layer was washed with water (20 mL) and brine (20 mL). After drying with Na$_2$SO$_4$ and removal of solvent, the residue purified by column chromatography to afford the title compound as light-yellow solid (0.43 g, 65.8% yield). $^1$H NMR (500 MHz, DMSO-d6) δ: 9.24 (s, 1H), 8.45 (d, J=5.7 Hz, 1H), 7.90 (d, J=8.1 Hz, 2H), 7.78 (d, J=5.7 Hz, 1H), 7.65 (dd, J=8.5, 1.4 Hz, 1H), 6.95 (t, J=5.4 Hz, 1H), 3.27 (dd, J=13.5, 6.6 Hz, 2H), 2.91 (t, J=7.2 Hz, 2H), 1.34 (s, 9H).

Example 26

2-(Isoquinolin-6-yl)ethanamine

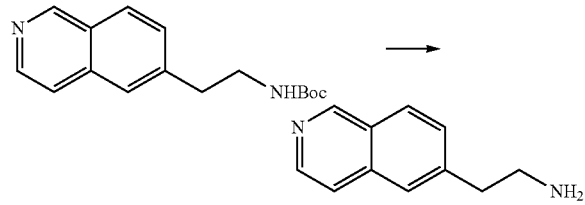

HCl (4 mL, 4N solution in 1,4-dioxane) was added to a stirred solution of tert-butyl (2-(isoquinolin-6-yl)ethyl)carbamate (0.25 g, 0.918 mmol) in MeOH (2 mL) at room temperature. After stirring for 1.5 h, the excess solvent was removed under reduced pressure to afford the crude product, which was used for the next step directly.

Example 27

2-(Furan-2-yl)-N5-(2-(isoquinolin-6-yl)ethyl)-[1,2,4]triazolo[1,5-a][1,3,5]triazine-5,7-diaminee

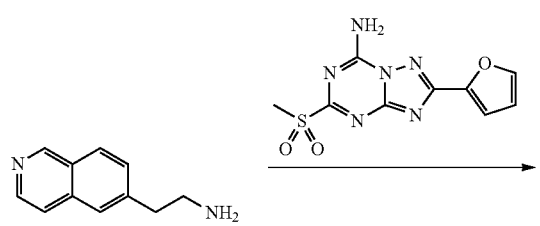

-continued

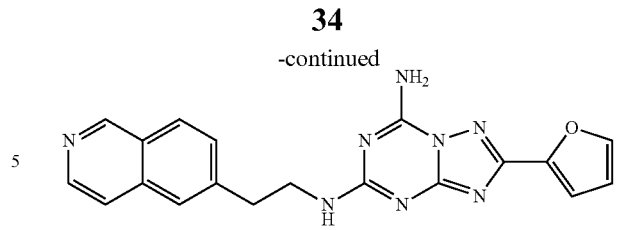

The reaction was carried out as in Example 5 to afford the title compound as white solid (0.0212 g, 8.8% yield). $^1$H NMR (500 MHz, DMSO-d6) δ: 9.27 (s, 1H), 8.37 (br, 3H), 7.92 (dd, J=27.4, 19.5 Hz, 3H), 7.76 (dd, J=35.7, 6.4 Hz, 2H), 7.61 (d, J=44.7 Hz, 1H), 7.06 (s, 1H), 6.68 (s, 1H), 3.63 (s, 2H), 3.10 (s, 2H).

Example 28

2-(Furan-2-yl)-N5-(2-(quinolin-6-yl)ethyl)-[1,2,4]triazolo[1,5-a][1,3,5]triazine-5,7-diamine

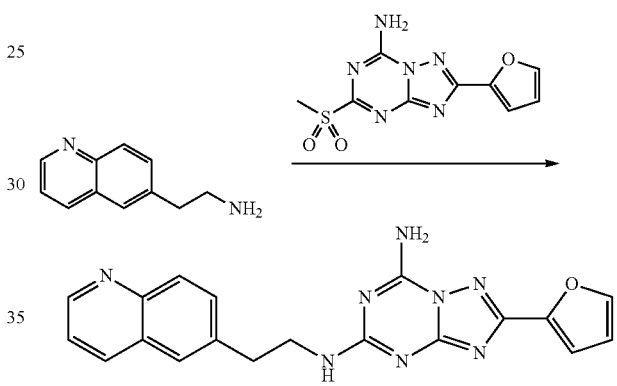

The title compound was synthesized in a similar way as the title compound in Example 27. $^1$H NMR (500 MHz, DMSO-d6) δ: 8.85 (dd, J=4.1, 1.6 Hz, 1H), 8.51-8.06 (m, 3H), 7.97 (d, J=8.6 Hz, 1H), 7.85 (d, J=26.5 Hz, 2H), 7.70 (t, J=9.8 Hz, 1H), 7.67-7.54 (m, 1H), 7.50 (dd, J=8.3, 4.2 Hz, 1H), 7.07 (d, J=3.3 Hz, 1H), 6.68 (d, J=1.6 Hz, 1H), 3.62 (dd, J=13.2, 6.6 Hz, 2H), 3.08 (t, J=7.3 Hz, 2H).

Example 29 tert-Butyl 4-(1-methyl-1H-1,2,4-triazol-3-yl)phenethylcarbamate

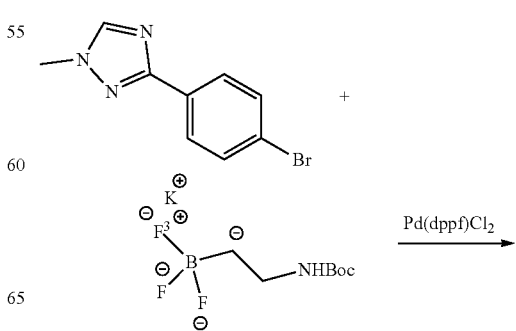

-continued

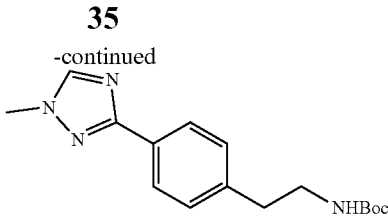

A solution of 3-(4-bromophenyl)-1-methyl-1H-1,2,4-triazole (0.5 g, 2.1 mmol), potassium tert-butyl N-[2-(trifluoroboranuidyl)ethyl]carbamate (0.58 g, 2.3 mmol), cesium carbonate (2.05 g, 6.3 mmol) and Pd(dppf)Cl$_2$ (0.077 g, 0.105 mmol) in toluene (12 mL) and water (4 mL) was stirred under N$_2$ at 80° C. overnight. The reaction mixture was filtered through Celite. The filtrate was extracted with ethyl acetate (30 mL×2). The organic layer was washed with water (20 mL) and brine (20 mL). After drying with Na$_2$SO$_4$ and removal of solvent, the residue purified by column chromatography to afford the title compound as light-yellow solid (0.416 g, 65.5% yield). $^1$H NMR (500 MHz, DMSO-d6) δ: 8.49 (s, 1H), 7.90 (d, J=8.1 Hz, 2H), 7.27 (d, J=8.2 Hz, 2H), 6.90 (t, J=5.4 Hz, 1H), 3.91 (s, 3H), 3.17 (dt, J=10.4, 5.5 Hz, 2H), 2.73 (t, J=7.4 Hz, 2H), 1.37 (s, 9H).

Example 30

2-(4-(1-Methyl-1H-1,2,4-triazol-3-yl)phenyl) ethanamine

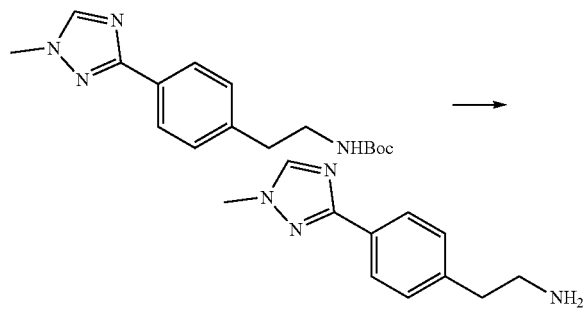

HCl (4 mL, 4N solution in 1,4-dioxane) was added to a stirred solution of tert-butyl 4-(1-methyl-JH-1,2,4-triazol-3-yl)phenethylcarbamate (0.31 g, 1.02 mmol) in MeOH (2 mL) at room temperature. After stirring for 1 h, the excess solvent was removed under reduced pressure to afford the crude product, which was used for the next step directly.

Example 31

2-(Furan-2-yl)-N5-(4-(1-methyl-1H-1,2,4-triazol-3-yl)phenethyl)-[1,2,4]triazolo[1,5-a][1,3,5]triazine-5,7-diamine

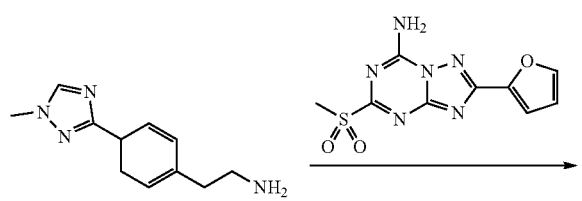

-continued

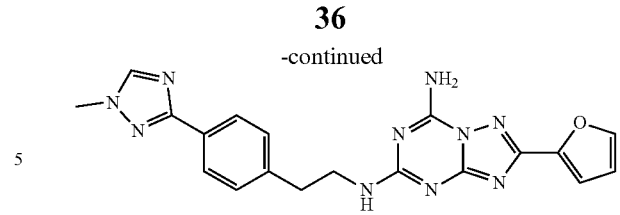

The reaction was carried out as in Example 5 to afford the title compound as white solid (0.1076 g, 37.4% yield). $^1$H NMR (500 MHz, DMSO-d6) δ: 8.49 (s, 1H), 8.19 (s, 2H), 7.98-7.84 (m, 3H), 7.54 (dd, J=25.9, 20.4 Hz, 1H), 7.35 (t, J=7.4 Hz, 2H), 7.13-7.01 (m, 1H), 6.68 (d, J=1.6 Hz, 1H), 3.91 (s, 3H), 3.53 (dd, J=13.4, 6.7 Hz, 2H), 2.91 (t, J=7.3 Hz, 2H).

Example 32

Methyl 4-(2-(7-amino-2-(furan-2-yl)-[1,2,4]triazolo [1,5-a][1,3,5]triazin-5-ylamino)ethyl)-benzoate

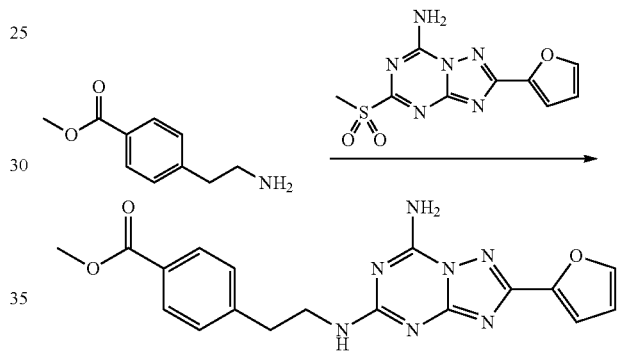

The reaction was carried out as in Example 5 to afford the title compound as yellow solid (41.1 mg, 10% yield). $^1$H NMR (500 MHz, DMSO-d6): 8.09-8.21 (m, 2H), 7.89 (d, 2H), 7.86 (s, 1H), 7.49-7.59 (m, 1H), 7.40-7.43 (m, 2H), 7.05 (d, 1H), 6.67 (dr, 1H), 3.83 (s, 3H), 3.50-3.54 (m, 2H), 2.93-2.96 (m, 2H).

Example 33

4-(2-(7-Amino-2-(furan-2-yl)-[1,2,4]triazolo[1,5-a] [1,3,5]triazin-5-ylamino)ethyl)benzoic acid

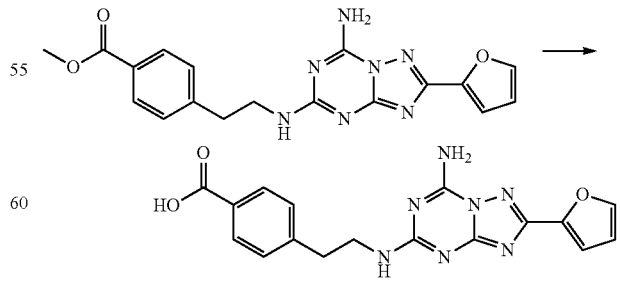

A mixture of methyl 4-(2-(7-amino-2-(furan-2-yl)-[1,2,4] triazolo[1,5-a][1,3,5]triazin-5-ylamino)ethyl)benzoate (200 mg, 0.52 mmol) and NaOH (210 mg, 5.2 mmol) in THF (10 mL) and H₂O (2 mL) was stirred at 40° C. overnight. TLC showed the reaction completed. The reaction mixture was neutralized by adding 10% HCl. It was next extracted with EtOAc. The organic layer was washed with water and brine, dried over sodium sulfate and concentrated in vacuo. The crude product was purified by column chromatography (EtOAc:Methanol=50:1) to afford the title compound as white solid (32 mg, 16.7% yield). ¹H NMR (500 MHz, DMSO-d6): 12.75 (dr, 1H), 8.09-8.21 (m, 2H), 7.89 (dr, 3H), 7.86 (s, 1H), 7.49-7.59 (m, 1H), 7.38 (dr, 2H), 7.05 (d, 1H), 6.67 (s, 1H), 3.52 (dr, 2H), 2.93 (dr, 2H).

Example 34

4-(2-(7-Amino-2-(furan-2-yl)-[1,2,4]triazolo[1,5-a][1,3,5]triazin-5-ylamino)ethyl)-N,N-dimethylbenzamide

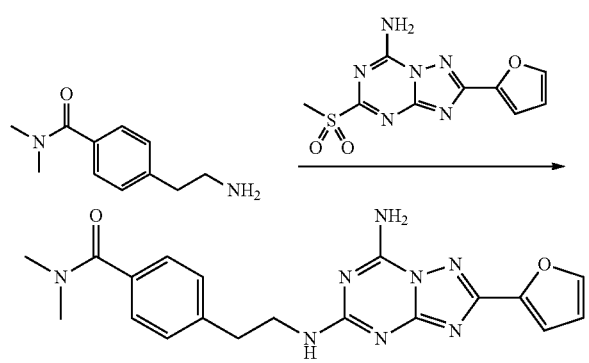

The title compound was synthesized in a similar way as the title compound in Example 11. ¹H LCMS [M+1]⁺: 393.23; ¹H NMR (500 MHz, DMSO-d6) δ: 8.03-8.24 (m, 2H), 7.86 (s, 1H), 7.49-7.58 (m, 1H), 7.32 (s, 4H), 7.05 (s, 1H), 6.67 (dr, 1H), 3.52 (dr, 2H), 2.89-2.95 (m, 8H).

Example 35

4-(2-(7-Amino-2-(furan-2-yl)-[1,2,4]triazolo[1,5-a][1,3,5]triazin-5-ylamino)ethyl)-N-methylbenzamide

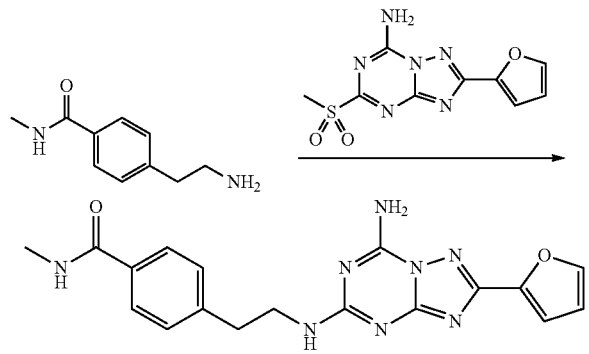

The title compound was synthesized in a similar way as the title compound in Example 11. ¹H NMR (500 MHz, DMSO-d6) δ: 8.35 (d, 1H), 8.03-8.24 (m, 2H), 7.86 (s, 1H), 7.76 (d, 2H), 7.49-7.58 (m, 1H), 7.32-7.33 (m, 2H), 7.05 (d, 1H), 6.67 (dr, 1H), 3.51 (d, 2H), 2.89-2.91 (m, 2H), 2.77 (d, 3H).

Example 36

4-(2-(7-Amino-2-(furan-2-yl)-[1,2,4]triazolo[1,5-a][1,3,5]triazin-5-ylamino)ethyl)benzamide

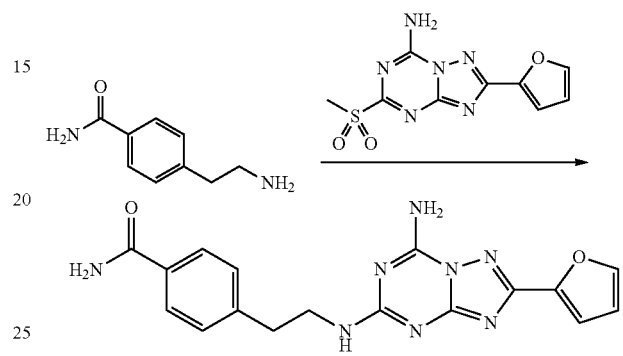

The title compound was synthesized in a similar way as the title compound in Example 11. ¹H NMR (500 MHz, DMSO-d6): 8.03-8.14 (m, 2H), 7.83 (d, 4H), 7.45-7.55 (m, 1H), 7.33 (dr, 1H), 7.23 (dr, 1H), 7.05 (dr, 1H), 6.67 (dr, 1H), 3.52 (dr, 2H), 2.91 (dr, 2H).

Example 37

(4-(2-(7-Amino-2-(furan-2-yl)-[1,2,4]triazolo[1,5-a][1,3,5]triazin-5-ylamino)ethyl)-phenyl)(piperidin-1-yl)methanone

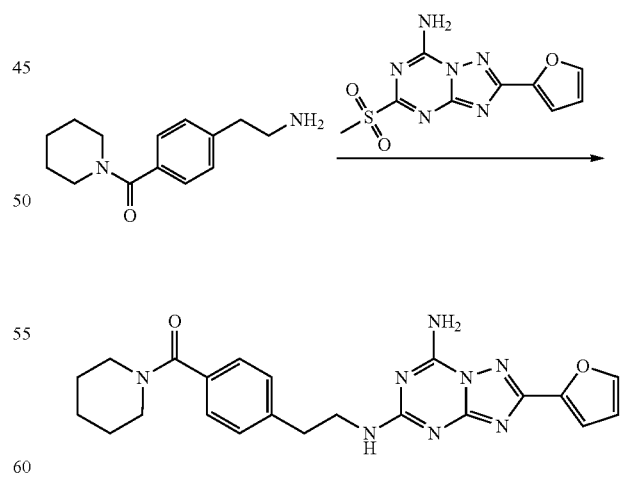

The title compound was synthesized in a similar way as the title compound in Example 11. ¹H NMR (500 MHz, DMSO-d6): 8.09-8.21 (m, 2H), 7.87 (s, 1H), 7.51-7.61 (m, 1H), 7.27-7.31 (m, 4H), 7.06 (d, 1H), 6.67-6.68 (m, 1H), 3.49-3.53 (m, 4H), 3.24 (dr, 2H), 2.86-2.90 (m, 2H), 1.40-1.59 (m, 6H).

Example 38

(4-(2-(7-Amino-2-(furan-2-yl)-[1,2,4]triazolo[1,5-a]
[1,3,5]triazin-5-ylamino)ethyl)-phenyl)(3,3-difluoro-
pyrrolidin-1-yl)methanone

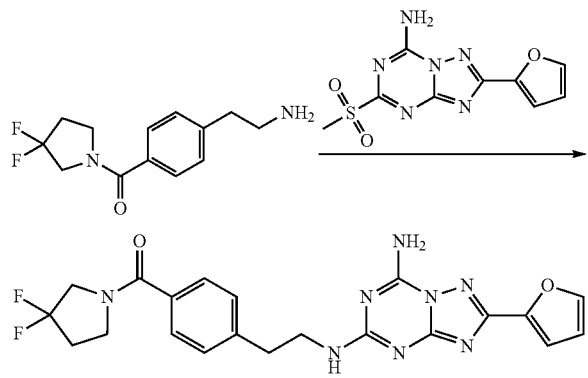

The title compound was synthesized in a similar way as the title compound in Example 11. $^1$H NMR (500 MHz, DMSO-d6): 8.09-8.41 (m, 2H), 7.87 (s, 1H), 7.51-7.61 (m, 1H), 7.48 (d, 2H), 7.34 (t, 1H), 7.05 (d, 1H), 6.67-6.68 (m, 1H), 3.88 (m, 2H), 3.63-3.70 (m, 2H), 3.49-3.53 (m, 2H), 2.88-2.92 (m, 2H), 2.39-2.43 (m, 2H).

Example 39

(4-(2-(7-Amino-2-(furan-2-yl)-[1,2,4]triazolo[1,5-a]
[1,3,5]triazin-5-ylamino)ethyl)-phenyl)(3-fluoropip-
eridin-1-yl)methanone

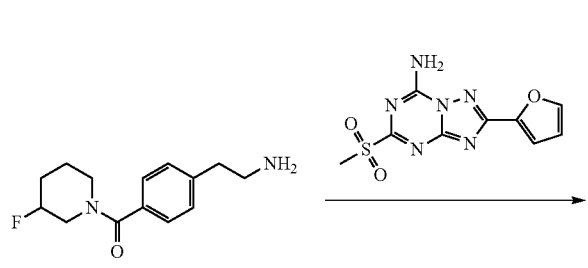

The title compound was synthesized in a similar way as the title compound in Example 11. $^1$H NMR (500 MHz, DMSO-d6): 8.09-8.21 (m, 2H), 7.87 (s, 1H), 7.50-7.61 (m, 1H), 7.28-7.34 (m, 4H), 7.05 (d, 1H), 6.67-6.68 (m, 1H), 4.74 (t, 1H), 4.02-4.15 (m, 1H), 3.38-3.65 (m, 4H), 2.86-3.07 (m, 3H), 1.45-1.87 (m, 4H).

Example 40

(4-(2-(7-Amino-2-(furan-2-yl)-[1,2,4]triazolo[1,5-a]
[1,3,5]triazin-5-ylamino)ethyl)-phenyl)((R)-3-fluoro-
pyrrolidin-1-yl)methanone

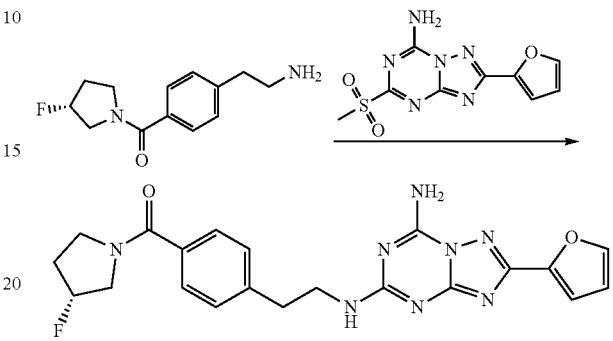

The title compound was synthesized in a similar way as the title compound in Example 11. $^1$H NMR (500 MHz, DMSO-d6): 8.09-8.21 (m, 2H), 7.87 (s, 1H), 7.45-7.58 (m, 3H), 7.32 (d, 2H), 7.05 (d, 1H), 6.67 (d, 1H), 5.31 (t, 1H), 3.64-3.79 (m, 2H), 3.38-3.65 (m, 4H), 3.46-3.60 (m, 4H), 2.89-2.92 (m, 2H), 1.99-2.16 (m, 2H).

Example 41

(4-(2-(7-Amino-2-(furan-2-yl)-[1,2,4]triazolo[1,5-a]
[1,3,5]triazin-5-ylamino)ethyl)-phenyl)(3,3-difluo-
ropiperidin-1-yl)methanone

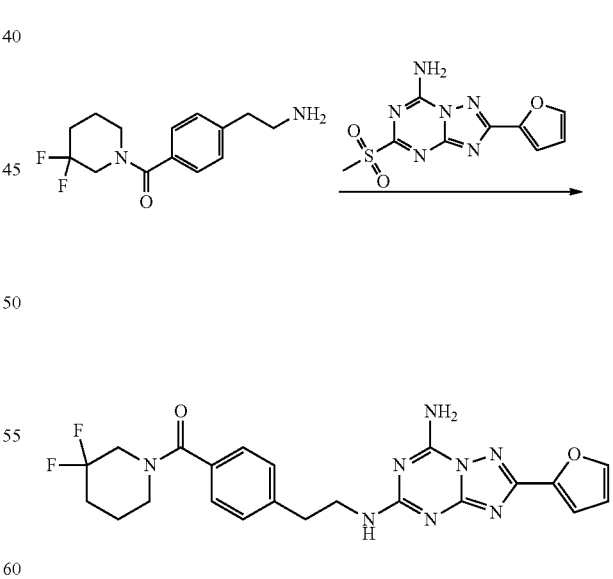

The title compound was synthesized in a similar way as the title compound in Example 11. $^1$H NMR (500 MHz, DMSO-d6): 8.09-8.21 (m, 2H), 7.87 (s, 1H), 7.50-7.59 (m, 1H), 7.30-7.35 (m, 4H), 7.05 (d, 1H), 6.67 (dr, 1H), 3.37-3.90 (m, 6H), 2.89-2.92 (m, 2H), 2.04-2.11 (m, 2H), 1.67 (dr, 2H).

Example 42

4-(2-(7-Amino-2-(furan-2-yl)-[1,2,4]triazolo[1,5-a][1,3,5]triazin-5-ylamino)ethyl)-N-isopropyl-N-methylbenzamide

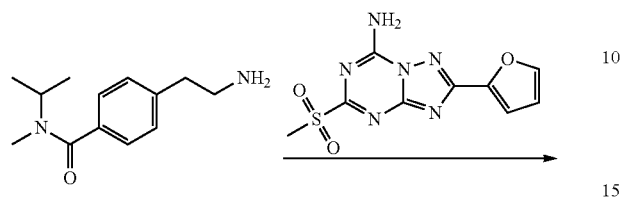

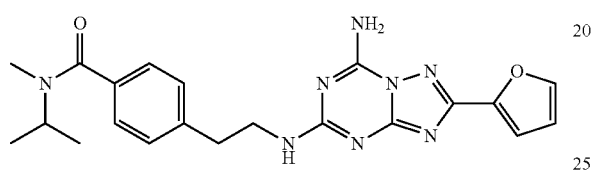

The title compound was synthesized in a similar way as the title compound in Example 11. $^1$H NMR (500 MHz, DMSO-d6): 8.09-8.21 (m, 2H), 7.86 (s, 1H), 7.48-7.56 (m, 1H), 7.27-7.31 (m, 4H), 7.05 (d, 1H), 6.67 (d, 1H), 4.68 (dr, 0.4H), 3.79 (dr, 0.6H), 3.51-3.52 (m, 2H), 2.87-2.90 (m, 2H), 2.77 dr, 3H), 1.07 (m, 6H).

Example 43

4-(2-(7-Amino-2-(furan-2-yl)-[1,2,4]triazolo[1,5-a][1,3,5]triazin-5-ylamino)ethyl)-N-(1-hydroxy-2-methylpropan-2-yl)benzamide

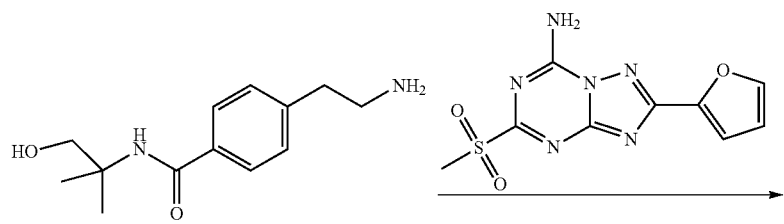

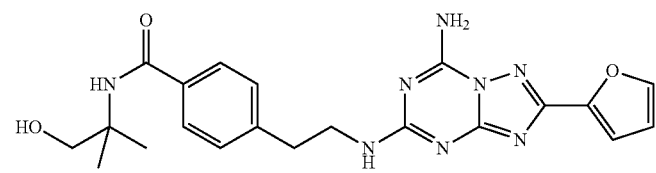

The title compound was synthesized in a similar way as the title compound in Example 11. $^1$H LCMS [M+1]$^+$: 437.2; $^1$H NMR (500 MHz, DMSO-d6): 8.09-8.21 (m, 2H), 7.87 (s, 1H), 7.73 (d, 2H), 7.49-7.53 (m, 1H), 7.47 (s, 1H), 7.32 (t, 1H), 7.05 (d, 2H), 6.67 (d, 1H), 4.91 (t, 1H), 3.48-3.52 (m, 4H), 2.89-2.92 (m, 2H), 1.30 (s, 6H).

Example 44

4-(2-(7-Amino-2-(furan-2-yl)-[1,2,4]triazolo[1,5-a][1,3,5]triazin-5-ylamino)ethyl)-N-(1-hydroxy-2-methylpropan-2-yl)benzamide

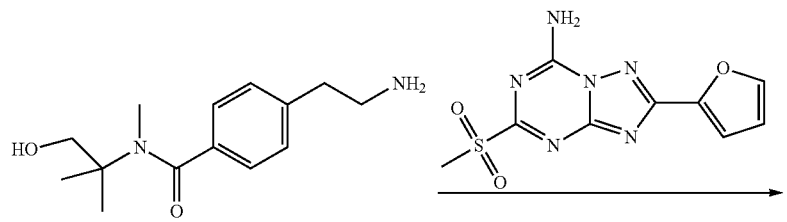

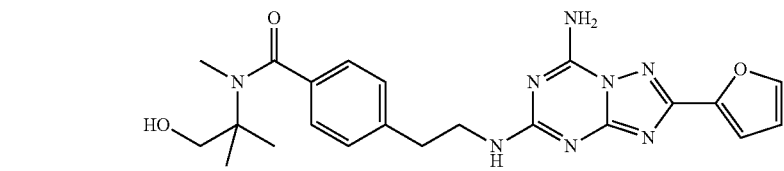

The title compound was synthesized in a similar way as the title compound in Example 11. ¹H NMR (500 MHz, DMSO-d6): 8.09-8.21 (m, 2H), 7.96 (d, 2H), 7.87 (s, 1H), 7.52-7.61 (m, 1H), 742 (d, 2H), 7.06 (s, 1H), 6.68 (s, 1H), 4.09 (t, 2H), 3.48-3.52 (m, 2H), 2.89-2.94 (m, 2H), 1.10 (s, 6H).

Example 45

(4-(2-(7-Amino-2-(furan-2-yl)-[1,2,4]triazolo[1,5-a][1,3,5]triazin-5-ylamino)ethyl)phenyl)-(7,8-dihydro-1,6-naphthyridin-6(5H)-yl)methanone

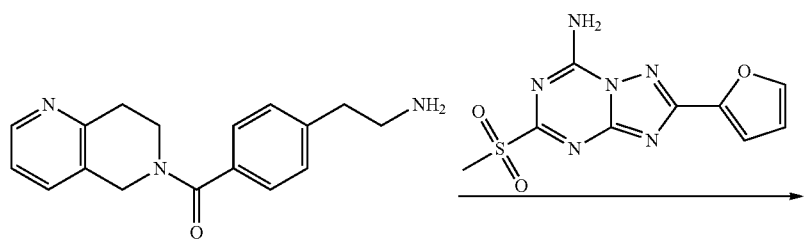

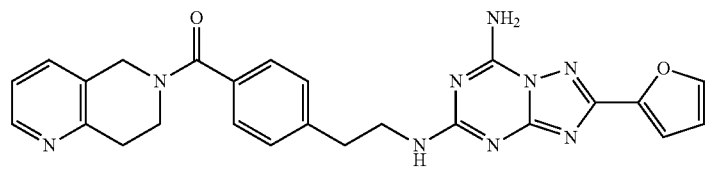

The title compound was synthesized in a similar way as the title compound in Example 11. ¹H LCMS [M+1]⁺: 482.2; ¹H NMR (500 MHz, DMSO-d6): 8.38 (s, 1H), 8.09-8.21 (m, 2H), 7.86 (s, 1H), 7.51-7.69 (m, 3H), 7.34-7.40 (m, 4H), 7.23 (dr, 1H), 7.05 (d, 1H), 6.67 (s, 1H), 4.61-4.77 (m, 2H), 3.64-3.92 (m, 2H), 3.53-3.54 (m, 2H), 2.90-2.94 (m, 4H).

Example 46

Benzyl 4-bromophenethylcarbamate

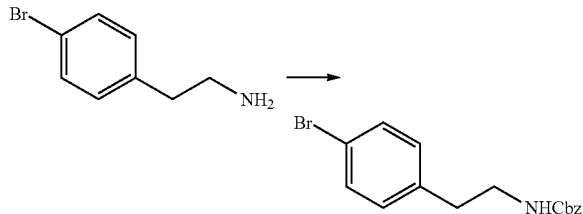

To a solution of 2-(4-bromophenyl)ethanamine hydrochloride (10.0 g, 49.9 mmol) in THF (40 mL) and water (15 mL) was added Na$_2$CO$_3$ (15.9 g, 150 mmol) and CbzCl (10.2 g, 59.9 mmol) at 0° C. The reaction mixture was stirred at room temperature for 2 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:2) to afford the title compound as white solid (16.7 g, 100%). $^1$H NMR (500 MHz, DMSO-d6): 7.45 (d, 2H), 7.29-7.36 (m, 6H), 7.15 (d, 2H), 4.99 (s, 2H), 3.20-3.24 (m, 2H), 2.69 (t, 2H).

Example 47

Benzyl 4-cyanophenethylcarbamate

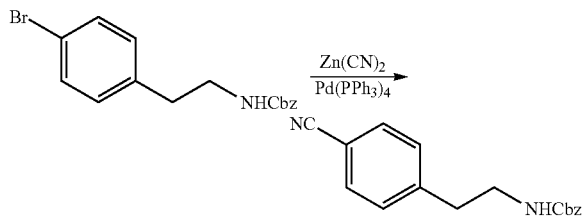

To a solution of benzyl 4-bromophenethylcarbamate (13.7 g, 41.1 mmol) in DMF (40 mL) was added Zn(CN)$_2$ (4.93 g, 41.2 mmol) and Pd(PPh$_3$)$_4$ (4.75 g, 4.11 mmol). The reaction mixture was stirred at 100° C. under N$_2$ overnight. TLC showed the reaction completed. The reaction mixture was quenched with water and filtered. The residue was stirred in a mixed solvent of ethyl acetate and hexane (100 mL, EtOAc:Hexane=1:6) for 30 min. It was next filtered and dried to afford the title compound as white solid (8.9 g, 77.6%). $^1$H NMR (500 MHz, DMSO-d$_6$): 7.74 (d, 2H), 7.28-7.41 (m, 8H), 4.99 (s, 2H), 3.25-3.29 (m, 2H), 2.81 (t, 2H).

Example 48

Benzyl 4-(2H-tetrazol-5-yl)phenethylcarbamate

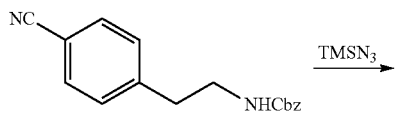

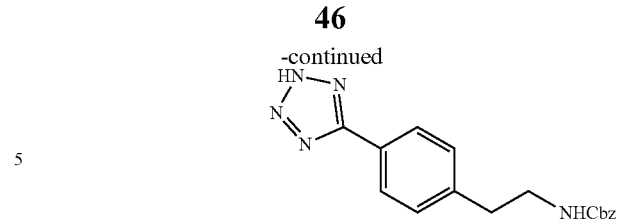

To a solution of benzyl 4-cyanophenethylcarbamate (5.0 g, 20.3 mmol) was added TMSN$_3$ (9.35 g, 81.2 mmol) and TBAF (monohydrate form, 2.65 g, 10.1 mmol). The reaction mixture was stirred at 90° C. under N$_2$ overnight. TLC showed the reaction completed. The reaction mixture was concentrated in vacuo. The crude product was purified by column chromatography to afford the title compound as white solid (5.0 g, 76% yield). $^1$H NMR (500 MHz, DMSO-d6): 7.95 (d, 2H), 7.29-7.44 (m, 8H), 5.00 (s, 2H), 3.27-3.29 (m, 2H), 2.81 (t, 2H).

Example 49

Benzyl 4-(2-methyl-2H-tetrazol-5-yl)phenethylcarbamate A4) and Benzyl 4-(1-methyl-1H-tetrazol-5-yl)phenethylcarbamate

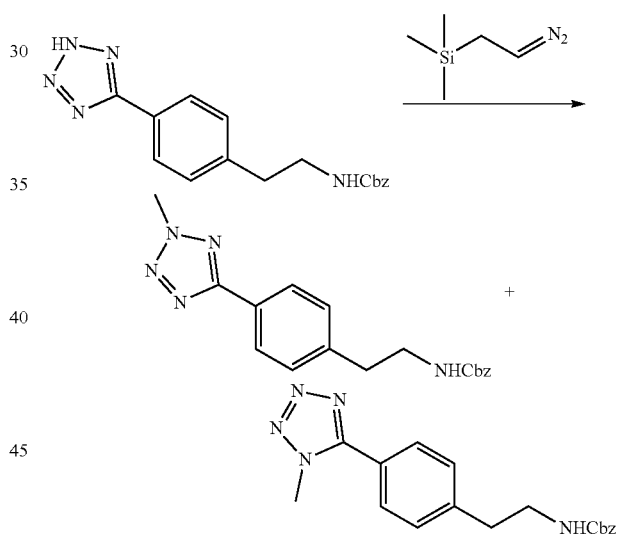

To a solution of benzyl 4-(2H-tetrazol-5-yl)phenethylcarbamate (1.97 g, 6.09 mmol) in THF (40 mL) was added 2.5 N (trimethylsilyl)diazomethane solution in hexane (10 mL) slowly at 0° C. The reaction mixture was stirred at 0° C. for 1 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:2) to afford benzyl 4-(2-methyl-2H-tetrazol-5-yl)phenethylcarbamate (1.37 g, 67%) and benzyl 4-(1-methyl-1H-tetrazol-5-yl)phenethylcarbamate (400 mg, 19%).

Benzyl 4-(2-methyl-2H-tetrazol-5-yl)phenethylcarbamate. $^1$H NMR (500 MHz, DMSO-d6): 7.96 (d, 2H), 7.30-7.39 (m, 8H), 5.00 (s, 2H), 4.42 (s, 3H), 3.27-3.29 (m, 2H), 2.80 (t, 2H).

Benzyl 4-(1-methyl-1H-tetrazol-5-yl)phenethylcarbamate. $^1$H NMR (500 MHz, DMSO-d6): 7.70 (d, 2H), 7.45 (d, 2H), 7.29-7.39 (m, 6H), 5.00 (s, 2H), 4.15 (s, 3H), 3.27-3.29 (m, 2H), 2.84 (t, 2H).

Example 50

2-(4-(2-Methyl-2H-tetrazol-5-yl)phenyl)ethanamine

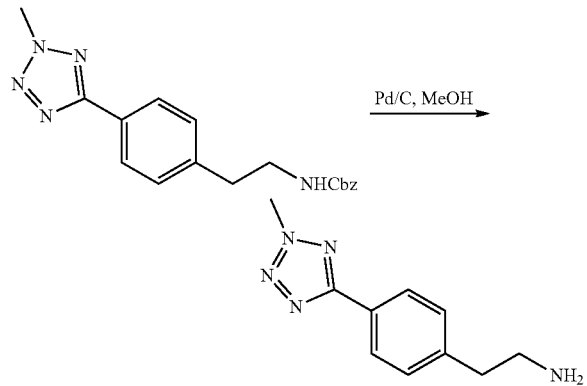

To a solution of benzyl 4-(2-methyl-2H-tetrazol-5-yl)phenethylcarbamate (1.37 g, 0.27 mmol) in MeOH (20 mL) was added Pd/C (10%). The reaction mixture was stirred at 40° C. under H$_2$. for 2 h. TLC showed the reaction completed. The reaction mixture was filtered through diatomite. The filtrate was concentrated in vacuo to afford the title compound as white solid, which was used for the next step directly.

Example 51

N5-(4-(2-Methyl-2H-tetrazol-5-yl)phenethyl)-2-(furan-2-yl)-[1,2,4]triazolo[1,5-a][1,3,5]triazine-5,7-diamine

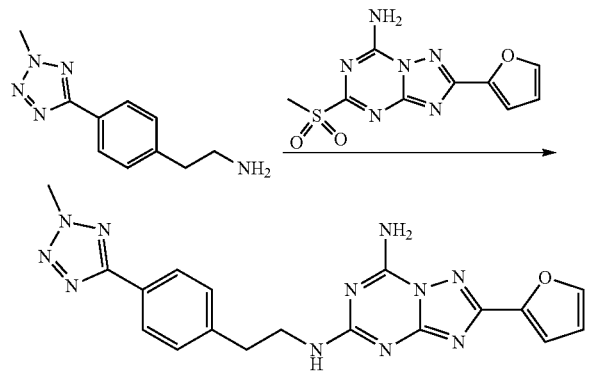

The reaction was carried out as in Example 5 to afford the title compound as white solid (109.4 mg, 38% yield). $^1$H NMR (500 MHz, DMSO-d6): 8.18-8.47 (m, 2H), 7.98 (d, 2H), 7.87 (s, 1H), 7.53-7.61 (m, 1H), 7.45 (t, 2H), 7.05 (d, 1H), 6.67 (dr, 1H), 4.41 (s, 3H), 3.52-3.56 (m, 2H), 2.89-2.96 (m, 2H).

Example 52

2-(4-(1-Methyl-1H-tetrazol-5-yl)phenyl)ethanamine

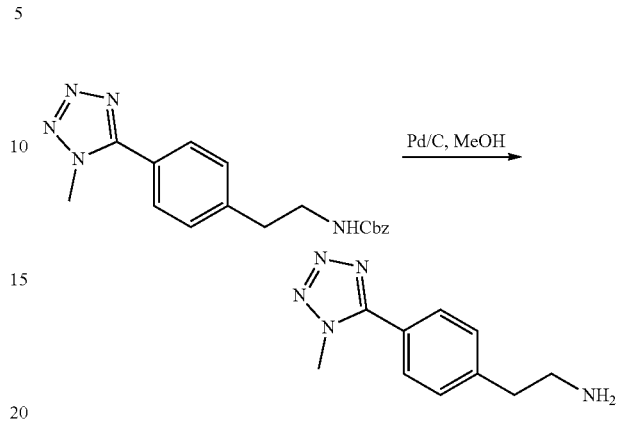

To a solution of benzyl 4-(1-methyl-1H-tetrazol-5-yl)phenethylcarbamate (400 mg, 1.18 mmol) in MeOH (10 mL) was added Pd/C (10%). The reaction mixture was stirred at 40° C. under H$_2$ for 2 h. TLC showed the reaction completed. The reaction mixture was filtered through diatomite. The filtrate was concentrated in vacuo to afford the title compound as white solid, which was used for the next step directly.

Example 53

N5-(4-(1-Methyl-1H-tetrazol-5-yl)phenethyl)-2-(furan-2-yl)-[1,2,4]triazolo[1,5-a][1,3,5]triazine-5,7-diamine

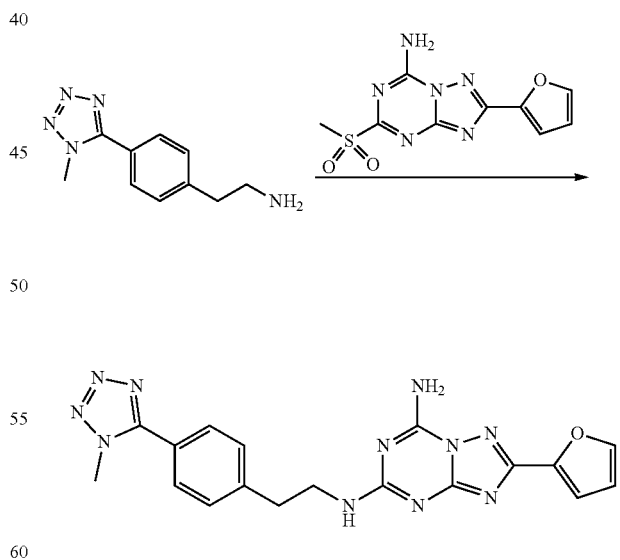

The reaction was carried out as in Example 5 to afford the title compound as white solid (82.7 mg, 24% yield). $^1$H NMR (500 MHz, DMSO-d6): 8.12-8.21 (m, 2H), 7.86 (s, 1H), 7.79 (d, 2H), 7.50-7.62 (m, 3H), 7.05 (d, 1H), 6.67 (dr, 1H), 4.15 (s, 3H), 3.55-3.56 (m, 2H), 2.96-2.99 (m, 2H).

Example 54

5-(4-Bromophenyl)-2-methyl-2H-tetrazole

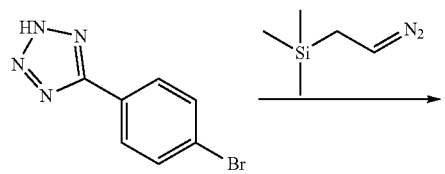

To a solution of 5-(4-bromophenyl)-2H-tetrazole (10 g, 44.43 mmol) in THF (150 mL) was added 2.5 N (trimethylsilyl)diazomethane solution in hexane (50 mL) slowly at 0° C. The reaction mixture was stirred at 0° C. for 1 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:5) to afford the title compound as white solid (6.24 g, 59%). $^1$H NMR (500 MHz, DMSO-d6): 7.84 (d, 2H), 7.62 (d, 2H), 4.28 (s, 3H).

Example 55 tert-Butyl 4-(2-methyl-2H-tetrazol-5-yl)phenethylcarbamate

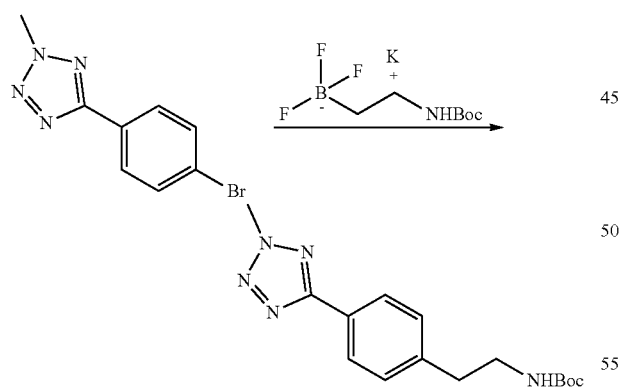

To a solution of 5-(4-bromophenyl)-2-methyl-2H-tetrazole (6.24 g, 26.1 mmol) in toluene (40 mL) and water (10 mL) was added cesium carbonate (17 g, 52.2 mmol), Pd(dppf)Cl$_2$ (1.9 g, 2.61 mmol) and potassium tert-butyl N-[2-(trifluoroboranuidyl)ethyl]carbamate (7.21 g, 28.7 mmol). The reaction mixture was stirred at 80° C. under N$_2$ overnight. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=2:5) to afford the title compound as white solid (6.3 g, 79.7%). $^1$H NMR (500 MHz, DMSO-d6): 7.96 (d, 2H), 7.38 (d, 2H), 6.92 (t, 1H), 4.42 (s, 3H), 3.17-3.21 (m, 2H), 2.77 (t, 2H), 1.36 (s, 9H).

Example 56

2-(4-(2-Methyl-2H-tetrazol-5-yl)phenyl)ethanamine

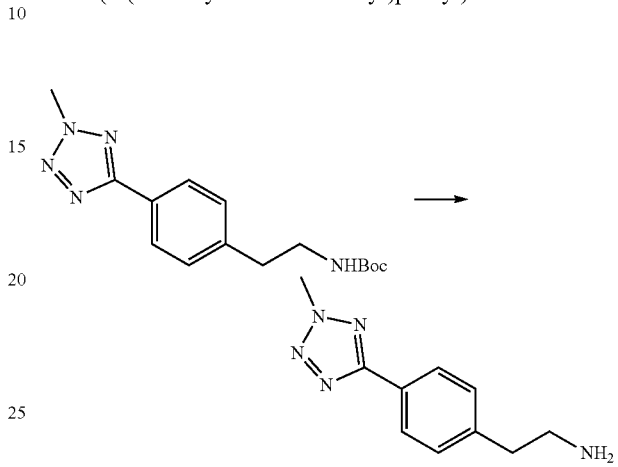

To a solution of tert-butyl 4-(2-methyl-2H-tetrazol-5-yl)phenethylcarbamate (6.22 g, 20.5 mmol) in 1,4-dioxane (4 mL) was added 4N HCL/dioxane (4 mL). The reaction mixture was stirred at room temperature overnight. TLC showed the reaction completed. The excess HCl and 1,4-dioxane were removed to give the crude product (5.1 g, 90%), which was used for the next step directly (See Example 51).

Example 57

Benzyl 4-(2-ethyl-2H-tetrazol-5-yl)phenethylcarbamate

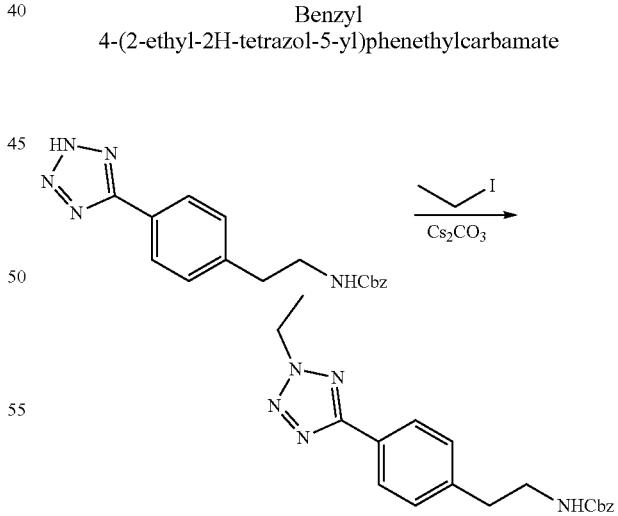

To a solution of benzyl 4-(2h-tetrazol-5-yl)phenethylcarbamate (300 mg, 0.93 mmol) in MeCN (15 mL) was added cesium carbonate (630 mg, 1.93 mmol) and iodoethane (800 mg, 5.12 mmol). The reaction mixture was stirred at 70° C. for 2 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:3) to afford the title compound as white solid (230 mg, 70.5%). ¹H NMR (500 MHz, DMSO-d6): 7.97 (d, 2H), 7.29-7.39 (m, 8H), 5.00 (s, 2H), 4.73-4.77 (m, 2H), 3.26-3.33 (m, 2H), 2.80 (t, 2H), 1.57 (t, 3H).

Example 58

2-(4-(2-Ethyl-2H-tetrazol-5-yl)phenyl)ethanamine

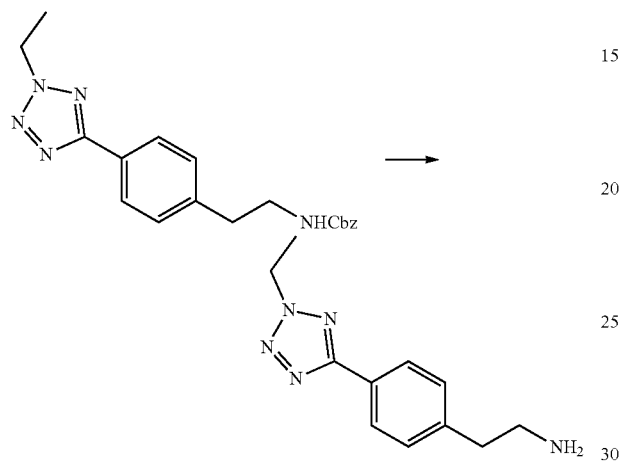

To a solution of benzyl 4-(2-ethyl-2H-tetrazol-5-yl)phenethylcarbamate (230 mg, 0.65 mmol) in MeOH (20 mL) was added Pd/C (10%). The reaction mixture was stirred under H₂ at 40° C. for 2 h. TLC showed the reaction completed. The reaction mixture was filtered through diatomite. The filtrate was concentrated in vacuo to afford the title compound as white solid (120 mg, 86%), which was used for the next step directly.

Example 59

N5-(4-(2-Ethyl-2H-tetrazol-5-yl)phenethyl)-2-(furan-2-yl)-[1,2,4]triazolo[1,5-a][1,3,5]triazine-5,7-diamine

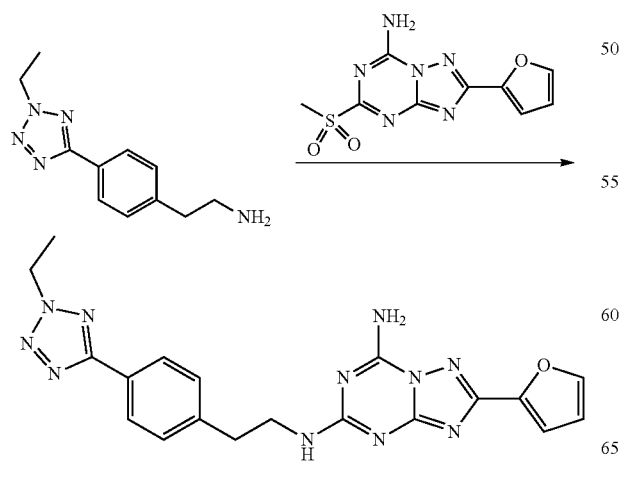

The reaction was carried out as in Example 5 to afford the title compound as white solid (104 mg, 50% yield). ¹H NMR (500 MHz, DMSO-d6): 8.18-8.47 (m, 2H), 7.98 (d, 2H), 7.87 (s, 1H), 7.53-7.62 (m, 1H), 7.45 (t, 2H), 7.05 (d, 1H), 6.67 (dr, 1H), 4.42-4.47 (m, 2H), 3.52-3.56 (m, 2H), 2.93-2.96 (m, 2H), 1.57 (t, 3H).

Example 60

Benzyl 4-(2-isopropyl-2H-tetrazol-5-yl)phenethylcarbamate

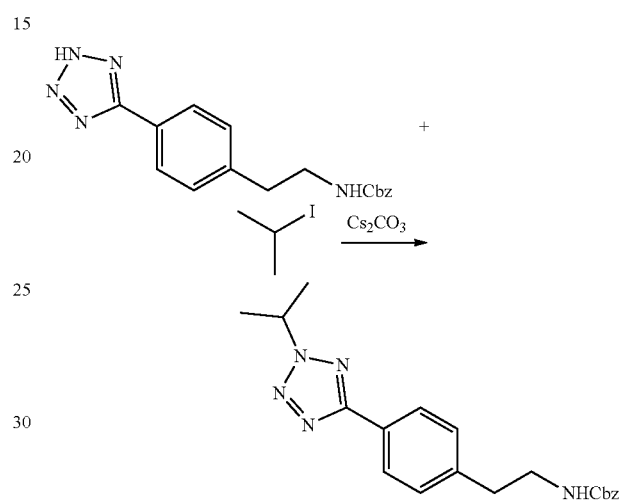

To a solution of benzyl 4-(2h-tetrazol-5-yl)phenethylcarbamate (300 mg, 0.93 mmol) in MeCN (15 mL) was added cesium carbonate (630 mg, 1.93 mmol) and 2-iodopropane (473 mg, 2.98 mmol). The reaction mixture was stirred at 70° C. for 2 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:3) to afford the title compound as white solid (253 mg, 74.6%). ¹H NMR (500 MHz, DMSO-d6): 7.97 (d, 2H), 7.30-7.39 (m, 8H), 5.16-5.19 (m, 1H), 5.00 (s, 2H), 3.27-3.33 (m, 2H), 2.80 (t, 2H), 1.63 (dd, 6H).

Example 61

2-(4-(2-Isopropyl-2H-tetrazol-5-yl)phenyl)ethanamine

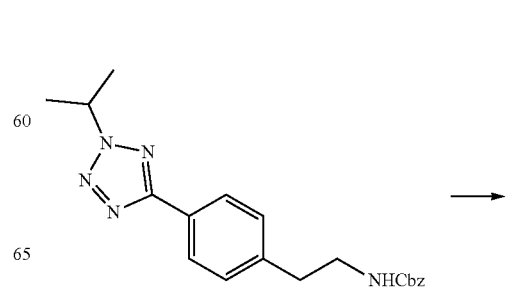

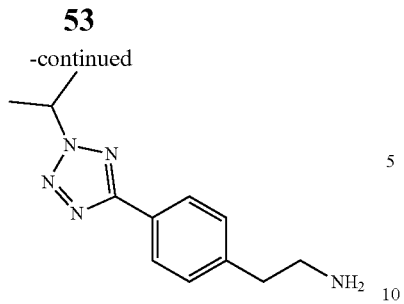

To a solution of benzyl 4-(2-isopropyl-2H-tetrazol-5-yl)phenethylcarbamate (253 mg, 0.69 mmol) in MeOH (20 mL) was added Pd/C (10%). The reaction mixture was stirred under H₂ at 40° C. for 2 h. TLC showed the reaction completed. The reaction mixture was filtered through diatomite. The filtrate was concentrated in vacuo to afford the title compound as white solid (143 mg, 90%), which was used for the next step directly.

Example 62

N5-(4-(2-Isopropyl-2H-tetrazol-5-yl)phenethyl)-2-(furan-2-yl)-[1,2,4]triazolo[1,5-a][1,3,5]triazine-5,7-diamine

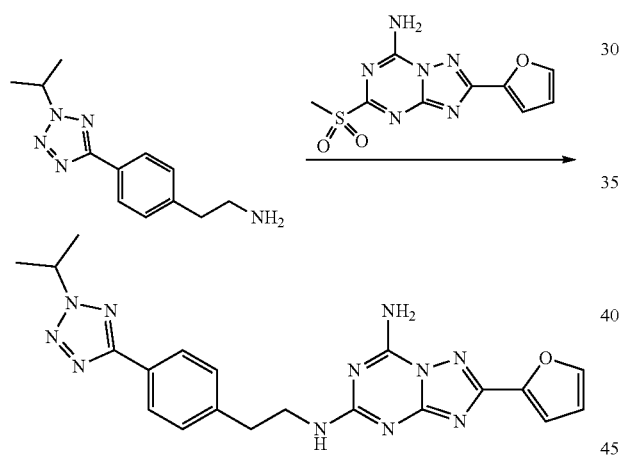

The reaction was carried out as in Example 5 to afford the title compound as white solid (132.7 mg, 56% yield). ¹H NMR (500 MHz, DMSO-d6): 8.18-8.47 (m, 2H), 7.98 (d, 2H), 7.87 (s, 1H), 7.53-7.61 (m, 1H), 7.45 (t, 2H), 7.05 (d, 1H), 6.67 (dr, 1H), 5.15-5.18 (m, 1H), 3.53-3.56 (m, 2H), 2.89-2.96 (m, 2H), 1.61 (d, 6H).

Example 63

Benzyl 4-(2-(2-methoxyethyl)-2H-tetrazol-5-yl)phenethylcarbamate

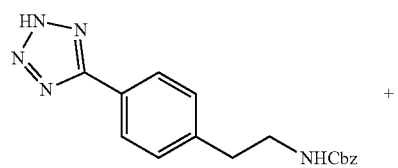

+

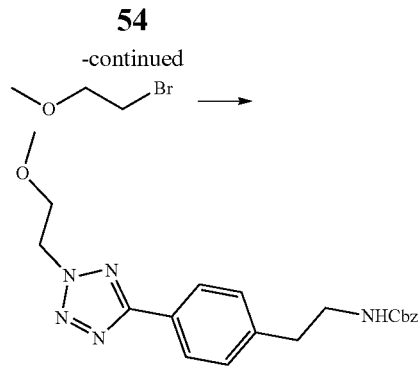

To a solution of benzyl 4-(2h-tetrazol-5-yl)phenethylcarbamate (300 mg, 1.03 mmol) in MeCN (15 mL) was added cesium carbonate (674 mg, 2.07 mmol) and 1-bromo-2-methoxyethane (288 mg, 2.07 mmol). The reaction mixture was stirred at 70° C. for 2 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:2) to afford the title compound as yellow oil (248 mg, 63%).

Example 64

2-(4-(2-(2-Methoxyethyl)-2H-tetrazol-5-yl)phenyl)ethanamine

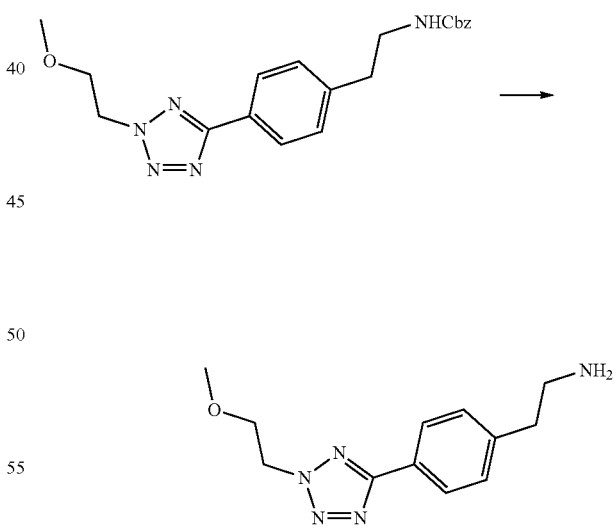

To a solution of benzyl 4-(2-(2-methoxyethyl)-2H-tetrazol-5-yl)phenethylcarbamate (248 mg, 0.65 mmol) in MeOH (10 mL) was added Pd/C (10%). The reaction mixture was stirred under H₂ at 50° C. for 2 h. TLC showed the reaction completed. The reaction mixture was filtered through diatomite. The filtrate was concentrated in vacuo to afford the title compound as yellow oil (150 mg, 94%), which was used for the next reaction directly.

Example 65

N5-(4-(2-(2-Methoxyethyl)-2H-tetrazol-5-yl)phenethyl)-2-(furan-2-yl)-[1,2,4]triazolo[1,5-a][1,3,5]triazine-5,7-diamine

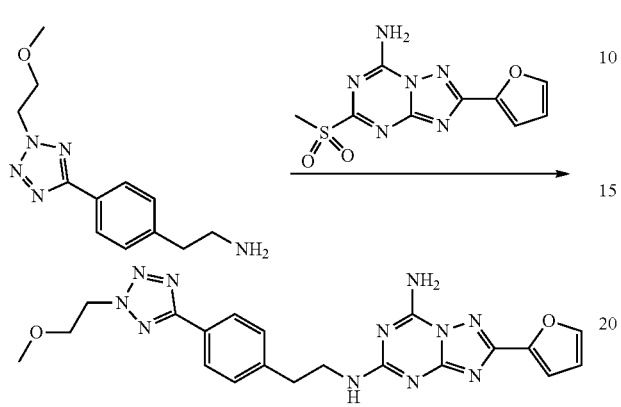

The reaction was carried out as in Example 5 to afford the title compound as white solid (91.7 mg, 36% yield). $^1$H NMR (500 MHz, DMSO-d6): 8.18-8.47 (m, 2H), 8.05 (d, 2H), 7.92 (s, 1H), 7.57-7.66 (m, 1H), 7.45 (t, 2H), 7.11 (d, 1H), 6.73 (dr, 1H), 4.95 (t, 2H), 3.96 (t, 2H), 3.59-3.61 (m, 2H), 3.29 (s, 3H), 2.99-3.02 (m, 2H).

Example 66

Benzyl 4-(2-propyl-2H-tetrazol-5-yl)phenethylcarbamate

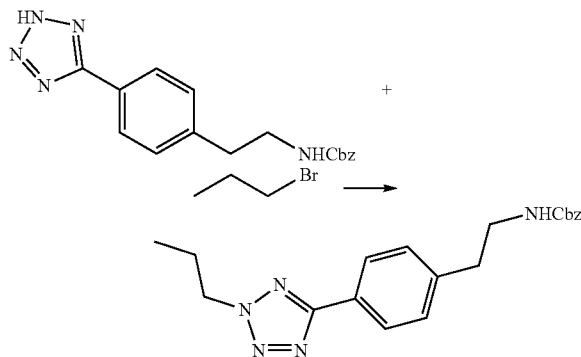

To a solution of benzyl 4-(2h-tetrazol-5-yl)phenethylcarbamate (232 mg, 0.72 mmol) in MeCN (15 mL) was added cesium carbonate (700 mg, 3.58 mmol) and 1-bromopropane (441 mg, 3.58 mmol). The reaction mixture was stirred at 70° C. for 2 h. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:4) to afford the title compound as white solid (200 mg, 76.6%). $^1$H NMR (500 MHz, DMSO-d6): 7.97 (d, 2H), 7.29-7.39 (m, 8H), 5.00 (s, 2H), 4.69 (t, 2H), 3.27-3.33 (m, 2H), 2.80 (t, 2H), 1.96-2.00 (m, 2H), 0.89 (t, 3H).

Example 67

2-(4-(2-Propyl-2H-tetrazol-5-yl)phenyl)ethanamine

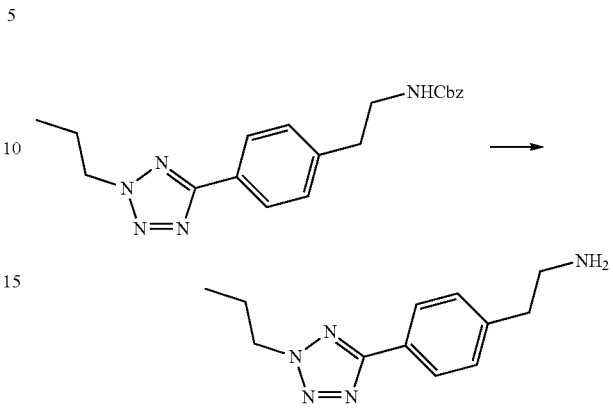

To a solution of benzyl 4-(2-propyl-2H-tetrazol-5-yl)phenethylcarbamate (200 mg, 0.54 mmol) in MeOH (20 mL) was added Pd/C (10%). The reaction mixture was stirred under H$_2$ at 40° C. for 2 h. TLC showed the reaction completed. The reaction mixture was filtered through diatomite. The filtrate was concentrated in vacuo to afford the title compound as white solid (100 mg, 80%), which was used for the next reaction directly.

Example 68

N5-(4-(2-Propyl-2H-tetrazol-5-yl)phenethyl)-2-(furan-2-yl)-[1,2,4]triazolo[1,5-a][1,3,5]triazine-5,7-diamine

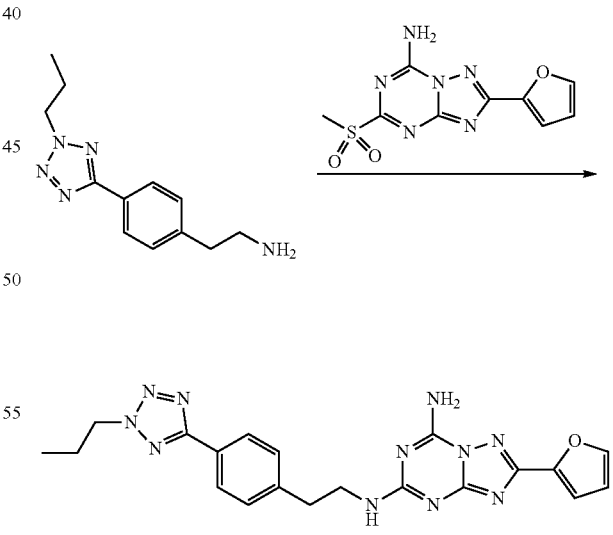

The reaction was carried out as in Example 5 to afford the title compound as white solid (95.4 mg, 66.7% yield). $^1$H NMR (500 MHz, DMSO-d6): 8.18-8.47 (m, 2H), 7.98 (d, 2H), 7.87 (s, 1H), 7.53-7.61 (m, 1H), 7.45 (t, 2H), 7.05 (d, 1H), 6.67 (dr, 1H), 4.69 (t, 2H), 3.53-3.56 (m, 2H), 2.93-2.96 (m, 2H), 1.96-2.00 (m, 2H), 0.899 (t, 3H).

Example 69

Benzyl 4-(2-(2,2,2-trifluoroethyl)-2H-tetrazol-5-yl)phenethylcarbamate

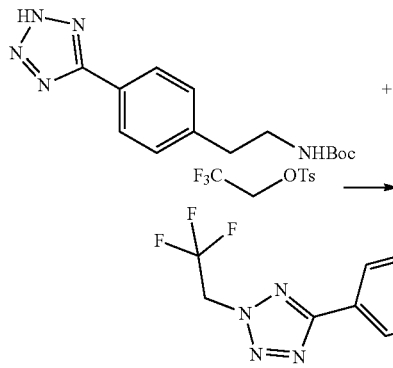

To a solution of tert-butyl 4-(2H-tetrazol-5-yl)phenethylcarbamate (285 mg, 0.98 mmol) in DMF (15 mL) was added cesium carbonate (645 mg, 1.98 mmol) and 2,2,2-trifluoroethyl 4-methylbenzenesulfonate (321 mg, 1.97 mmol). The reaction mixture was stirred at 100° C. overnight. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:4) to afford the title compound as yellow oil (81 mg, 22.3%). $^1$H NMR (500 MHz, DMSO-d6): 7.99 (d, 2H), 7.41 (d, 2H), 6.91 (t, 1H), 6.01-6.06 (m, 2H), 3.17-3.20 (m, 2H), 2.78 (t, 2H), 1.35 (s, 9H).

Example 70

2-(4-(2-(2,2,2-Trifluoroethyl)-2H-tetrazol-5-yl)phenyl)ethanamine

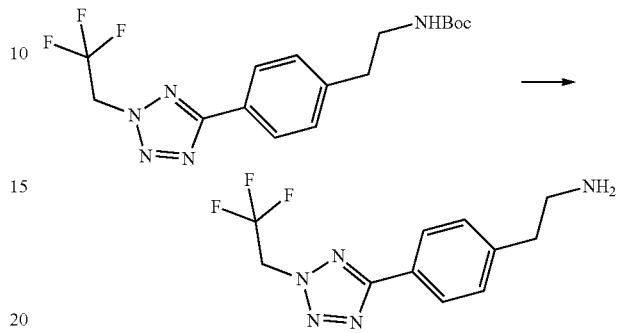

To a solution of benzyl 4-(2-(2,2,2-trifluoroethyl)-2H-tetrazol-5-yl)phenethylcarbamate (81 mg, 0.22 mmol) in dioxane (4 mL) was added 4N HCl/dioxane (4 mL). The reaction mixture was stirred at room temperature overnight. TLC showed the reaction completed. The excess HCl and dioxane were removed to afford the crude product, which was used for the next step directly.

Example 71

N5-(4-(2-(2,2,2-Trifluoroethyl)-2H-tetrazol-5-yl)phenethyl)-2-(furan-2-yl)-[1,2,4]triazolo[1,5-a][1,3,5]triazine-5,7-diamine

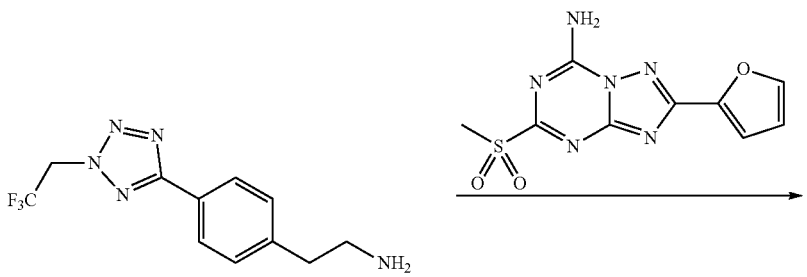

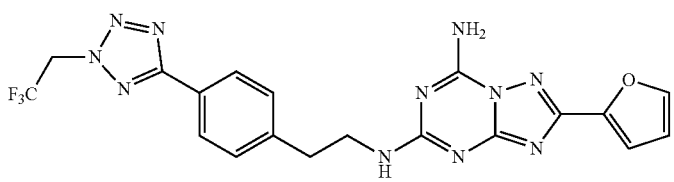

The reaction was carried out as in Example 5 to afford the title compound as white solid (24.9 mg, 25% yield). ¹H NMR (500 MHz, DMSO-d6): 8.18-8.47 (m, 2H), 8.03 (dr, 2H), 7.87 (s, 1H), 7.49-7.63 (m, 3H), 7.06 (s, 1H), 6.68 (s, 1H), 6.04 (dr, 2H), 3.55-3.56 (m, 2H), 2.95-2.96 (m, 2H).

Example 72 tert-Butyl 4-(6,7-dihydro-5H-pyrrolo[3,4-b]pyridine-6-carbonyl)phenethylcarbamate

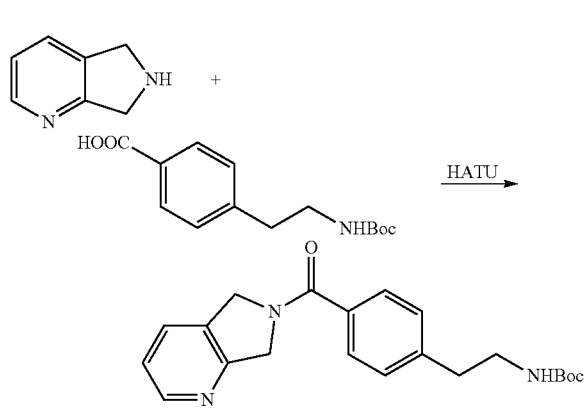

A mixture of 4-(2-((tert-butoxycarbonyl)amino)ethyl) benzoic acid (265 mg, 1 mmol), HATU (418 mg, 1.1 mmol) and DIPEA (387 mg, 3 mmol) in DCM (10 mL) was stirred at room temperature for 0.5 h. Then 6,7-dihydro-5H-pyrrolo [3,4-b]pyridine (193 mg, 1 mmol) was added and the reaction was stirred at room temperature overnight. TLC showed the reaction completed. The reaction mixture was concentrated and purified by column chromatography to afford the title compound as yellow solid (250 mg, 68.1% yield). ¹H NMR (500 MHz, DMSO-d6) δ 8.47 (dd, J=14.7, 4.5 Hz, 1H), 7.78 (dd, J=69.0, 7.6 Hz, 1H), 7.56 (dd, J=11.7, 8.0 Hz, 2H), 7.36-7.28 (m, 3H), 6.94 (d, J=5.6 Hz, 1H), 4.83 (t, J=29.2 Hz, 4H), 3.68-3.57 (m, 1H), 3.24-3.08 (m, 3H), 1.37 (s, 9H).

Example 73

(4-(2-Aminoethyl)phenyl)(5H-pyrrolo[3,4-b]pyridin-6(7H)-yl)methanone

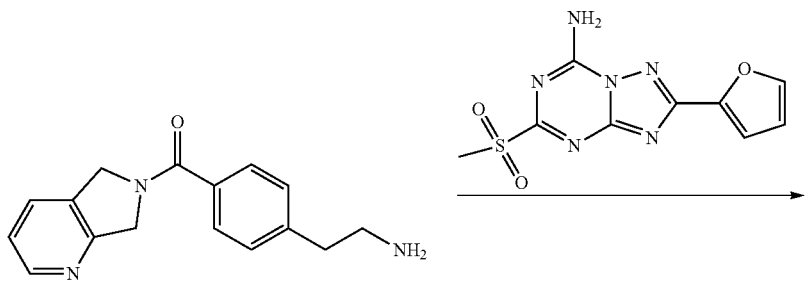

To a stirred mixture of tert-butyl 4-(6,7-dihydro-5H-pyrrolo[3,4-b]pyridine-6-carbonyl)phenethylcarbamate (250 mg, 0.68 mmol) in dioxane (8 mL) was added 4N HCl in dioxane (3 mL) at room temperature. The reaction mixture was stirred at room temperature for 2 h. TLC showed the reaction completed. The reaction mixture was concentrated in vacuo to afford the crude product, which was used for the next step directly.

Example 74

(4-(2-(7-Amino-2-(furan-2-yl)-[1,2,4]triazolo[1,5-a] [1,3,5]triazin-5-ylamino)ethyl)-phenyl)(5H-pyrrolo [3,4-b]pyridin-6(7H)-yl)methanone

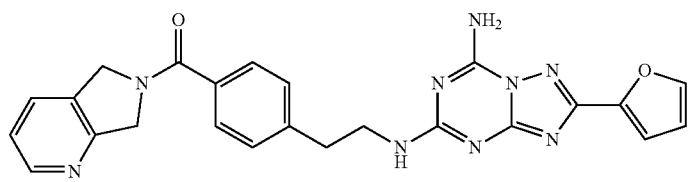

The reaction was carried out as in Example 5 to afford the title compound as white solid (88.7 mg, 28.0% yield). ¹H NMR (500 MHz, DMSO-d6) δ: 8.53-8.01 (m, 3H), 7.90-7.49 (m, 5H), 7.41-7.26 (m, 3H), 7.06 (d, J=3.0 Hz, 1H), 6.68 (s, 1H), 4.93-4.73 (m, 4H), 3.54 (dd, J=13.1, 6.6 Hz, 2H), 2.93 (d, J=5.6 Hz, 2H); LC-MS (m/z): 468.2[M+H]⁺

Example 75

2-(Furan-2-yl)-N-(4-(methylsulfonyl)phenethyl)-[1,2,4]triazolo[1,5-a][1,3,5]triazin-5-amine

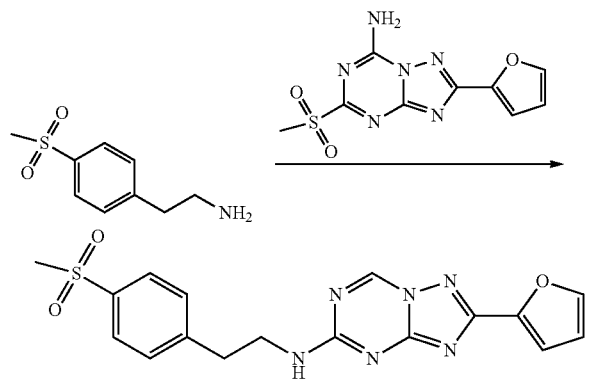

The reaction was carried out as in Example 5 to afford the title compound as white solid (150 mg, 39.1% yield). ¹H NMR (500 MHz, DMSO-d6) δ: 8.22 (s, 2H), 7.91-7.80 (m, 3H), 7.56 (dd, J=27.8, 18.4 Hz, 3H), 7.06 (d, J=3.3 Hz, 1H), 6.68 (d, J=1.6 Hz, 1H), 3.54 (dd, J=12.8, 6.5 Hz, 2H), 3.19 (s, 3H), 2.99 (t, J=7.1 Hz, 2H).

Example 76

4-(2-((2-(Furan-2-yl)-[1,2,4]triazolo[1,5-a][1,3,5]triazin-5-yl)amino)ethyl)benzene-sulfonamide

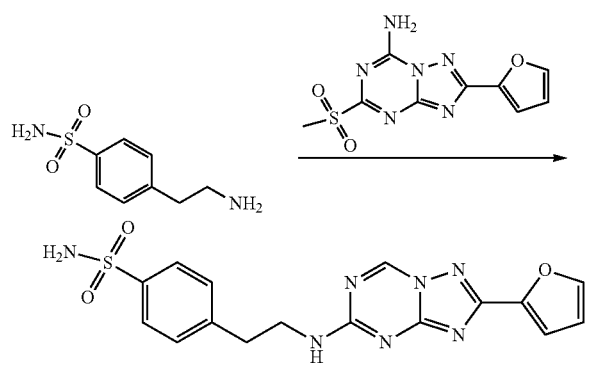

The reaction was carried out as in Example 5 to afford the title compound as white solid (27.3 mg, 7.1% yield). ¹H NMR (500 MHz, DMSO-d6) δ: 8.34 (d, J=120.0 Hz, 2H), 7.88 (s, 1H), 7.76 (d, J=8.0 Hz, 2H), 7.62-7.42 (m, 3H), 7.29 (s, 2H), 7.06 (d, J=3.2 Hz, 1H), 6.68 (d, J=1.5 Hz, 1H), 3.56-3.46 (m, 2H), 2.95 (t, J=7.2 Hz, 2H).

Example 77

5-Bromo-2-(2-methyl-2H-tetrazol-5-yl)pyridine

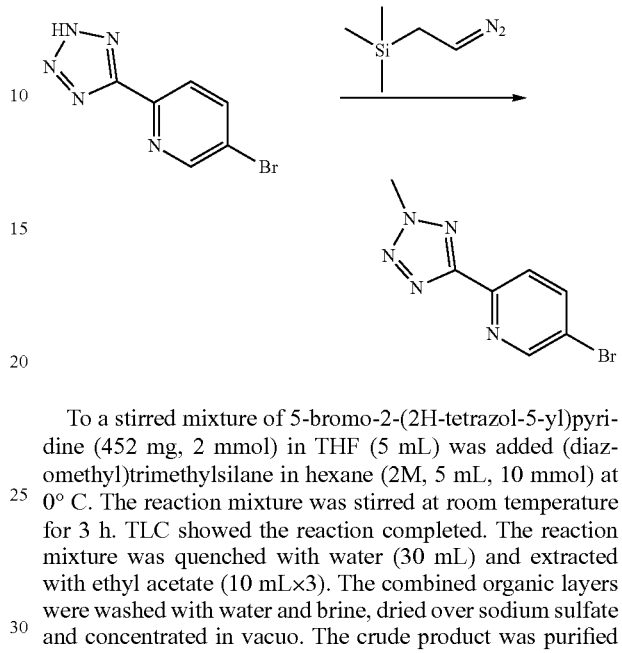

To a stirred mixture of 5-bromo-2-(2H-tetrazol-5-yl)pyridine (452 mg, 2 mmol) in THF (5 mL) was added (diazomethyl)trimethylsilane in hexane (2M, 5 mL, 10 mmol) at 0° C. The reaction mixture was stirred at room temperature for 3 h. TLC showed the reaction completed. The reaction mixture was quenched with water (30 mL) and extracted with ethyl acetate (10 mL×3). The combined organic layers were washed with water and brine, dried over sodium sulfate and concentrated in vacuo. The crude product was purified by column chromatography to afford the title compound as white solid (180 mg, 28.5% yield). ¹H NMR (500 MHz, DMSO-d6) δ: 9.00-8.89 (m, 1H), 8.32 (dd, J=8.5, 2.4 Hz, 1H), 8.14 (d, J=8.4 Hz, 1H), 4.34 (s, 3H).

Example 78 tert-Butyl 2-(6-(2-methyl-2H-tetrazol-5-yl)pyridin-3-yl)ethylcarbamate

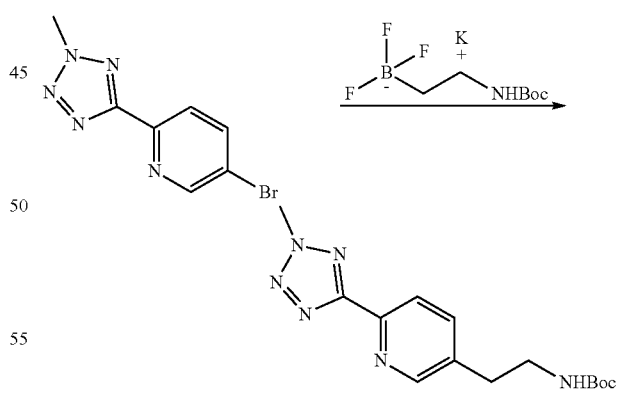

A mixture of 5-bromo-2-(2-methyl-2H-tetrazol-5-yl)pyridine (180 mg, 0.75 mmol), potassium tert-butyl N-[2-(trifluoroboranuidyl)ethyl]carbamate (207 mg, 0.83 mmol), cesium carbonate (733 mg, 2.25 mmol) and Pd(dppf)Cl₂ (15 mg) in toluene (6 mL) and water (2 mL) was stirred at 80° C. overnight. TLC showed the reaction completed. The reaction mixture was filtered. The filtrate was concentrated and purified by column chromatography to afford the title compound as white solid (150 mg, 65.8% yield). ¹H NMR (500 MHz, DMSO-d6) δ: 8.65 (d, J=1.8 Hz, 1H), 8.17 (d, J=8.0 Hz, 1H), 7.92 (dd, J=8.1, 2.1 Hz, 1H), 6.97 (t, J=5.4 Hz, 1H), 4.41 (s, 3H), 3.25 (dd, J=12.8, 6.7 Hz, 2H), 2.84 (t, J=6.9 Hz, 2H), 1.34 (s, 9H).

Example 79

2-(6-(2-Methyl-2H-tetrazol-5-yl)pyridin-3-yl)ethanamine

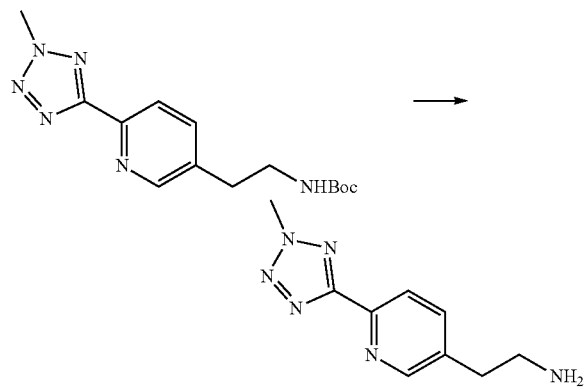

To a stirred mixture of tert-butyl 4-(2-methyl-2H-tetrazol-5-yl)phenethylcarbamate (150 mg, 0.49 mmol) in dioxane (5 mL) was added 4N HCl in dioxane (3 mL) at room temperature. The reaction mixture was stirred at room temperature overnight. TLC showed the reaction completed. The reaction mixture was concentrated in vacuo to afford the crude product, which was used for the next step directly.

Example 80

2-(Furan-2-yl)-N5-(2-(6-(2-methyl-2H-tetrazol-5-yl)pyridin-3-yl)ethyl)-[1,2,4]triazolo[1,5-a][1,3,5]triazine-5,7-diamine

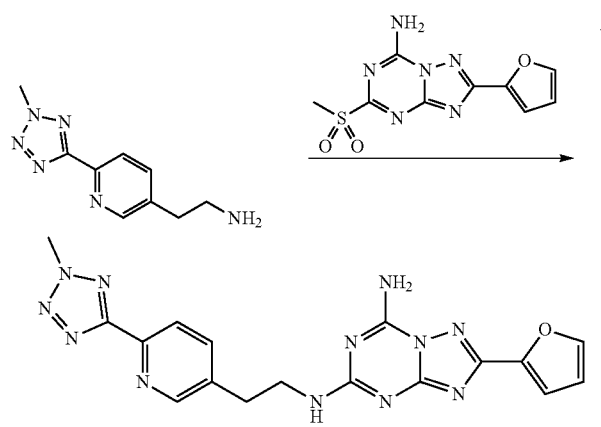

The reaction was carried out as in Example 5 to afford the title compound as white solid (39.0 mg, 19.7% yield). $^1$H NMR (500 MHz, DMSO-d6) δ: 8.72 (d, J=6.9 Hz, 1H), 8.27 (t, J=77.9 Hz, 3H), 7.99 (t, J=11.4 Hz, 1H), 7.87 (s, 1H), 7.60 (t, J=23.5 Hz, 1H), 7.05 (d, J=2.9 Hz, 1H), 6.68 (s, 1H), 4.40 (s, 3H), 3.59 (dd, J=12.5, 6.3 Hz, 2H), 3.02 (t, J=6.6 Hz, 2H).

Example 81

3-(4-Bromophenyl)-4-methyl-4H-1,2,4-triazole

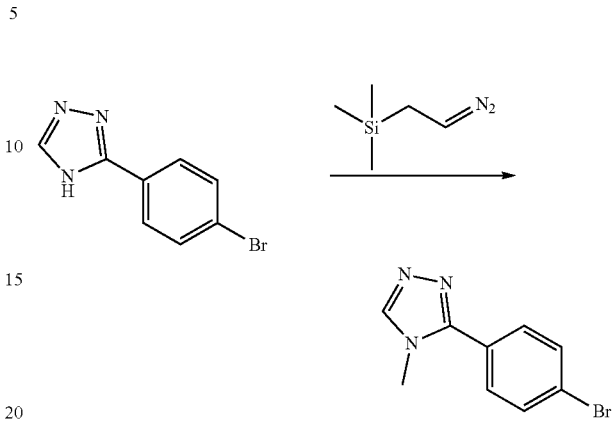

To a stirred mixture of 3-(4-bromophenyl)-4H-1,2,4-triazole (448 mg, 2 mmol) in THF (5 mL) was added (diazomethyl)trimethylsilane (5 mL, 10 mmol) at 0° C. The reaction mixture was stirred at room temperature overnight. TLC showed the reaction completed. The reaction mixture was concentrated in vacuo. The crude product was purified by column chromatography to afford the title compound as yellow oil (100 mg, 21.2% yield).

Example 82 tert-Butyl 4-(4-methyl-4H-1,2,4-triazol-3-yl)phenethylcarbamate

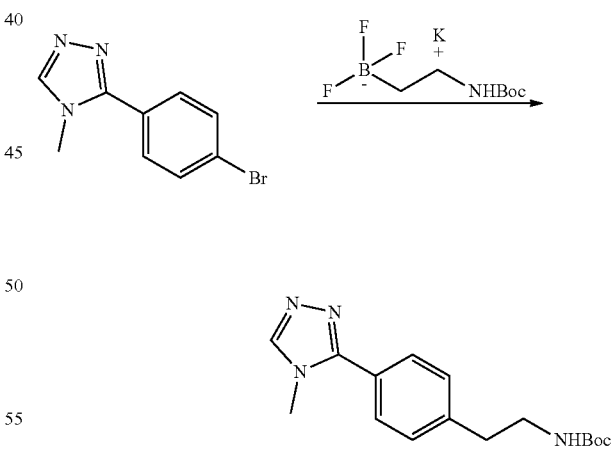

A mixture of 3-(4-bromophenyl)-4-methyl-4H-1,2,4-triazole (100 mg, 0.42 mmol), potassium tert-butyl N-[2-(trifluoroboranuidyl)ethyl]carbamate (116 mg, 0.46 mmol), cesium carbonate (410 mg, 1.26 mmol) and Pd(dppf)Cl$_2$ (15 mg) in toluene (3 mL) and water (1 mL) was stirred at 80° C. overnight. TLC showed the reaction completed. The reaction mixture was filtered. The filtrate was concentrated and purified by column chromatography to afford the title compound as white solid (61 mg, 47.3% yield).

Example 83

2-(4-(4-Methyl-4H-1,2,4-triazol-3-yl)phenyl)ethanamine

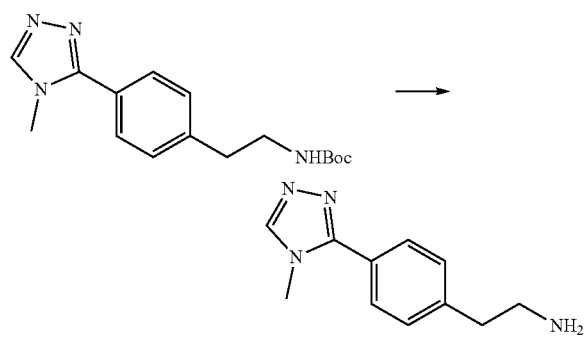

To a stirred mixture of tert-butyl 4-(4-methyl-4H-1,2,4-triazol-3-yl)phenethylcarbamate (61 mg, 0.2 mmol) in dioxane (4 mL) was added 4N HCl in dioxane (2 mL) at room temperature. The reaction mixture was stirred at room temperature overnight. TLC showed the reaction completed. The reaction mixture was concentrated in vacuo to afford the crude product, which was used for the next step directly.

Example 84

2-(Furan-2-yl)-N5-(4-(4-methyl-4H-1,2,4-triazol-3-yl)phenethyl)-[1,2,4]triazolo[1,5-a][1,3,5]triazine-5,7-diamine

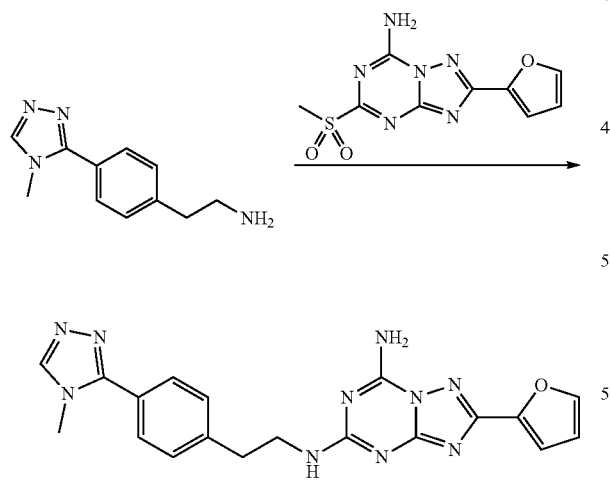

The reaction was carried out as in Example 5 to afford the title compound as white solid (23.3 mg, 29.0% yield). $^1$H NMR (500 MHz, DMSO-d6) δ: 8.31 (d, J=135.6 Hz, 2H), 7.98 (s, 1H), 7.87 (s, 1H), 7.72 (d, J=7.9 Hz, 2H), 7.55 (dd, J=26.5, 21.1 Hz, 1H), 7.45 (d, J=7.8 Hz, 2H), 7.06 (d, J=3.3 Hz, 1H), 6.68 (s, 1H), 3.96 (s, 3H), 3.56 (d, J=6.0 Hz, 2H), 2.96 (t, J=7.2 Hz, 2H).

Example 85

5-(Pyridin-2-yl)-1H-1,2,4-triazol-3-amine

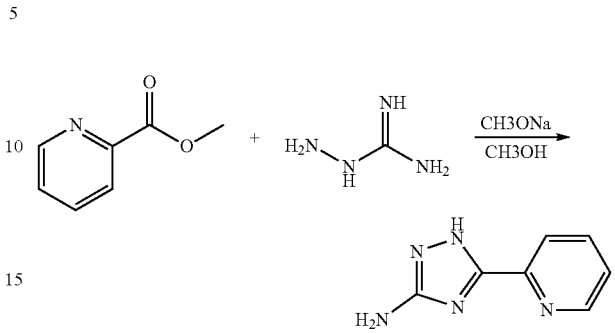

To a stirred mixture of CH$_3$ONa (31.49 g, 583 mmol) and hydrazinecarboximidamide (64.5 g, 583 mmol) in MeOH (450 mL) was added methyl picolinate (40 g, 292 mmol) in MeOH (120 mL) at 0° C. slowly. The reaction mixture was stirred at 75° C. overnight. TLC showed the reaction completed. The reaction mixture was filtered. The filtrate was concentrated afford the crude product. Then 150 mL of H$_2$O was added and the pH was adjusted to pH 5 with 36% hydrochloric acid. The precipitate formed was filtered to afford the title compound as white solid (21 g, 55.3% yield). $^1$H NMR (500 MHz, DMSO-d6) δ: 8.70-8.48 (m, 1H), 8.06-7.82 (m, 2H), 7.41 (ddd, J=7.2, 4.8, 1.4 Hz, 1H).

Example 86

5-(Methylthio)-2-(pyridin-2-yl)-[1,2,4]triazolo[1,5-a][1,3,5]triazin-7-amine

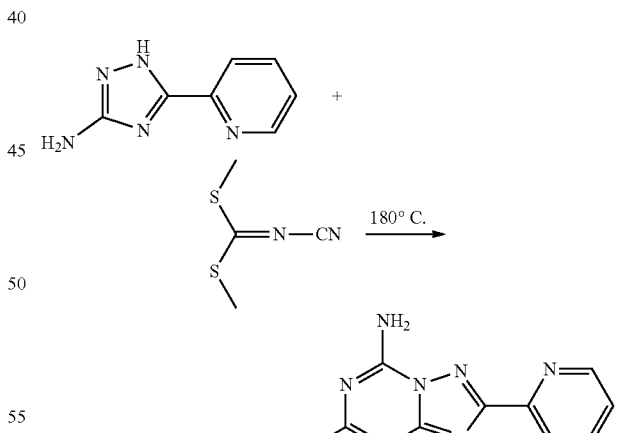

A mixture of 5-(pyridin-2-yl)-1H-1,2,4-triazol-3-amine (5.0 g, 31 mmol) and dimethyl cyanocarbonimidodithioate (4.5 g, 31 mmol) was stirred at 180° C. for 1 h. TLC showed the reaction completed. The residue was purified by column chromatography to afford the title compound as white solid (4.0 g, 50.0% yield). $^1$H NMR (500 MHz, DMSO-d6) δ: 8.95 (d, J=57.3 Hz, 2H), 8.74 (d, J=4.3 Hz, 1H), 8.22 (d, J=7.8 Hz, 1H), 8.01 (td, J=7.7, 1.7 Hz, 1H), 7.55 (dd, J=6.6, 4.8 Hz, 1H), 2.54 (s, 3H).

Example 87

5-Methylsulfonyl-2-(1-oxidopyridin-1-ium-2-yl)-[1,2,4]triazolo[1,5-a][1,3,5]triazin-7-amine

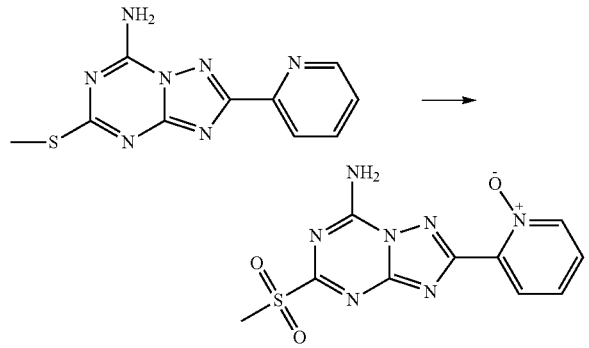

To a stirred mixture of 5-(methylthio)-2-(pyridin-2-yl)-[1,2,4]triazolo[1,5-a][1,3,5]triazin-7-amine (4.0 g, 15.4 mmol) in DCM (240 mL) was added m-CPBA (12.5 g, 61.6 mmol) in DCM (120 mL) at 0° C. The reaction mixture was stirred at room temperature overnight. TLC showed the reaction completed. The reaction mixture was concentrated in vacuo to afford the crude product. Then EtOH (80 mL) was added and the mixture was stirred at room temperature 1 h. The precipitate was filtered to afford the title compound as white solid (4.36 g, 92.2% yield). $^1$H NMR (500 MHz, DMSO-d6) δ: 8.95 (d, J=57.3 Hz, 2H), 8.74 (d, J=4.3 Hz, 1H), 8.22 (d, J=7.8 Hz, 1H), 8.01 (td, J=7.7, 1.7 Hz, 1H), 7.55 (dd, J=6.6, 4.8 Hz, 1H), 2.54 (s, 3H); LC-MS (m/z): 308.1 [M+H]$^+$

Example 88

N5-[2-[4-(2-methyltetrazol-5-yl)phenyl]ethyl]-2-(1-oxidopyridin-1-ium-2-yl)-[1,2,4]triazolo[1,5-a][1,3,5]triazine-5,7-diamine

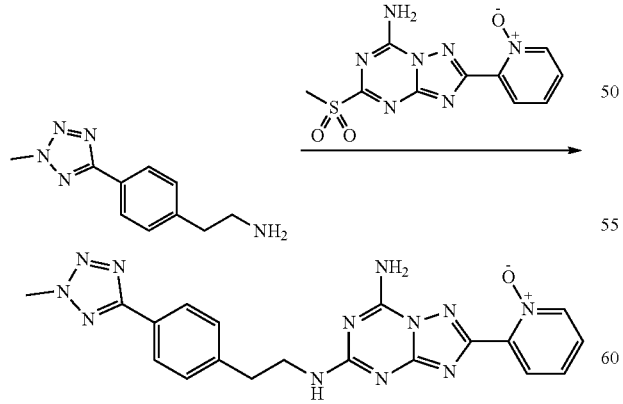

The reaction was carried out as in Example 5 to afford the title compound as white solid (120 mg, 27.9% yield). $^1$H NMR (500 MHz, DMSO-d6) δ: 8.59-8.12 (m, 3H), 7.99 (d, J=8.2 Hz, 2H), 7.90-7.81 (m, 1H), 7.62 (dd, J=28.5, 22.9 Hz, 1H), 7.56-7.51 (m, 1H), 7.45 (q, J=9.3 Hz, 3H), 4.42 (s, 3H), 3.60-3.53 (m, 2H), 2.96 (t, J=7.3 Hz, 2H); LC-MS (m/z): 431.2[M+H]+

Example 89 tert-Butyl 4-(pyrimidin-2-yl)phenethylcarbamate

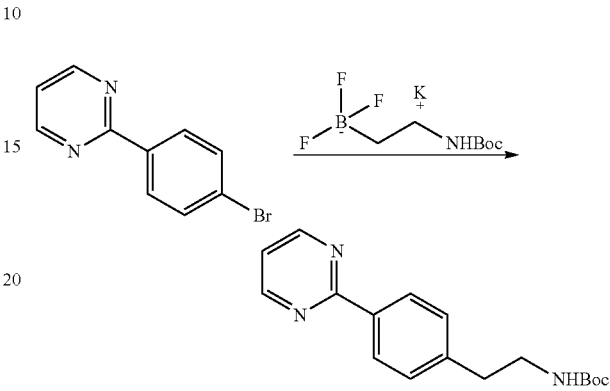

A mixture of 2-(4-bromophenyl)pyrimidine (470 mg, 2.00 mol), cesium carbonate (1300 mg, 4.00 mmol), Pd(dppf)Cl$_2$ (146 mg, 0.20 mmol) and potassium tert-butyl n-[2-(trifluoroboranuidyl)ethyl]carbamate (552 mg, 2.20 mmol) in toluene (7.5 ml) and water (2.5 mL) was stirred at 80° C. for 15 hours. The reaction mixture was diluted with ethyl acetate (100 mL) and washed with water and brine. The organic layer was dried with anhydrous sodium sulfate, concentrated and purified by column chromatography to afford the title compound as white solid (550 mg, 92.0% yield). $^1$HNMR (500 MHz, DMSO-d6) δ: 8.88 (d, 2H), 8.31 (d, 2H), 7.41 (t, 1H), 7.35 (d, 2H), 6.91 (t, 1H), 3.19 (q, 2H), 2.77 (t, 2H), 1.37 (s, 9H).

Example 90

2-(4-(Pyrimidin-2-yl)phenyl)ethanamine

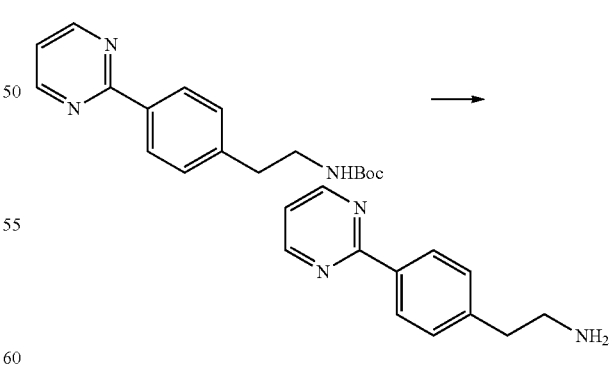

To a stirred solution of tert-butyl 4-(pyrimidin-2-yl)phenethylcarbamate (550 mg, 1.84 mol) in 1,4-dioxane (3 ml) was added 4M HCl in 1,4-dioxane (2 mL). After stirring at 35° C. for 3 hours, the reaction mixture was concentrated in vacuo to afford the title compound as white solid, which was used for the next step directly.

Example 91

2-(Furan-2-yl)-N5-(4-(pyrimidin-2-yl)phenethyl)-[1,2,4]triazolo[1,5-a][1,3,5]triazine-5,7-diamine

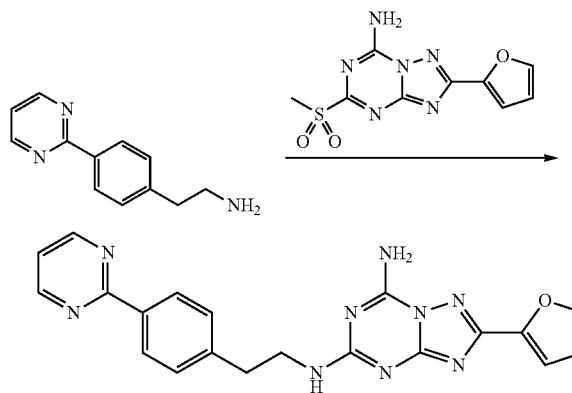

To a stirred solution of 2-(4-(pyrimidin-2-yl)phenyl)ethanamine (366 mg, 1.84 mmol) and 2-(furan-2-yl)-5-(methylsulfonyl)-[1,2,4]triazolo[1,5-a][1,3,5]triazin-7-amine (412 mg, 0.1.47 mmol) in MeCN (5 mL) was added TEA to adjust pH to 8. After stirring at room temperature for 15 h, the precipitated solid was collected and dried to afford the title compound as yellow solid (390 mg, 66.5% yield). $^1$H NMR (500 MHz, DMSO-d6) δ: 8.88 (d, 2H), 8.05-8.49 (d, 2H), 8.33 (d, 2H), 7.87 (s, 1H), 7.53 (d, 1H), 7.42 (q, 3H), 7.06 (d, 1H), 6.67 (d, 1H), 3.06 (t, 2H), 2.95 (t, 2H); LCMS m/z [M+H]$^+$: 400.2

Example 92

5-(Methylsulfonyl)-2-phenyl-[1,2,4]triazolo[1,5-a][1,3,5]triazin-7-amine

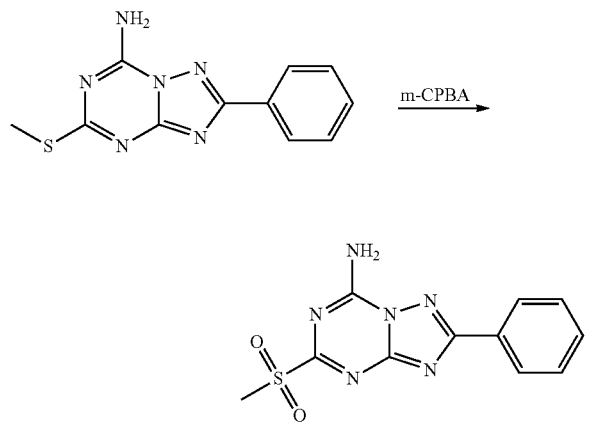

The title compound was prepared in a similar way as the title compound in Example 4. $^1$H NMR (500 MHz, DMSO-d6) δ: 9.83 (s, 1H), 9.39 (s, 1H), 8.32-8.16 (m, 2H), 7.66-7.54 (m, 3H), 3.38 (s, 3H).

Example 93

N5-(4-(2-Methyl-2H-tetrazol-5-yl)phenethyl)-2-phenyl-[1,2,4]triazolo[1,5-a][1,3,5]triazine-5,7-diamine

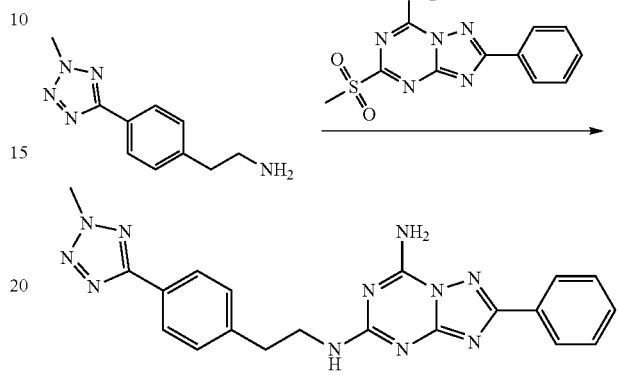

The reaction was carried out as in Example 5 to afford the title compound as white solid (0.132 g, 43.7% yield). LC-MS m/z [M+H]$^+$: 414; $^1$H NMR (500 MHz, DMSO-d6) δ: 8.42-8.12 (d, J=6.4 Hz, 3H), 8.00 (d, J=8.1 Hz, 3H), 7.59-7.42 (m, 6H), 4.42 (s, 3H), 3.57 (d, J=6.4 Hz, 2H), 2.96 (t, J=7.2 Hz, 2H).

Example 94 tert-Butyl 4-(pyridin-2-yl)phenethylcarbamate

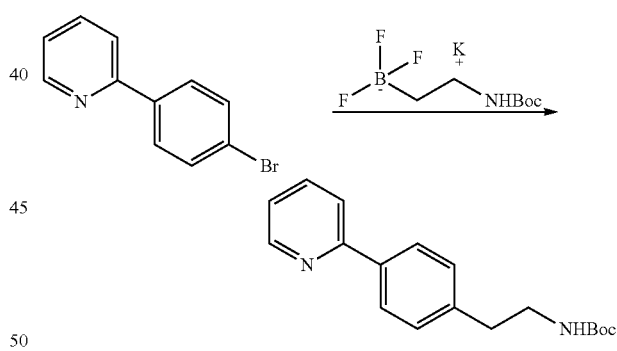

A solution of 2-(4-bromophenyl)pyridine (0.6 g, 2.56 mmol), potassium tert-butyl N-[2-(trifluoroboranuidyl)ethyl]carbamate (0.708 g, 2.82 mmol), cesium carbonate (2.5 g, 7.68 mmol), Pd(dppf)Cl$_2$ (0.095 g, 0.13 mmol) in PhMe (12 mL) and water (4 mL) was stirred at 80° C. overnight under N$_2$. The reaction mixture was filtered through Celite, the filtrate was concentrated in vacuo, diluted with water (30 mL) and extracted with ethyl acetate (30 mL×2), the combined organic layers washed with water (20 mL) and brine (20 mL). After drying with Na$_2$SO$_4$ and removal of solvent, the residue purified by column chromatography to afford the title compound as white solid (0.65 g, 85.1% yield). $^1$H NMR (500 MHz, DMSO-d6) δ: 8.71-8.59 (m, 1H), 8.01 (d, J=8.2 Hz, 2H), 7.95-7.82 (m, 2H), 7.32 (ddd, J=8.3, 4.8, 2.4 Hz, 3H), 6.91 (t, J=5.4 Hz, 1H), 3.25-3.12 (m, 2H), 2.76 (t, J=7.4 Hz, 2H), 1.38 (s, 9H).

Example 95

2-(4-(Pyridin-2-yl)phenyl)ethanamine

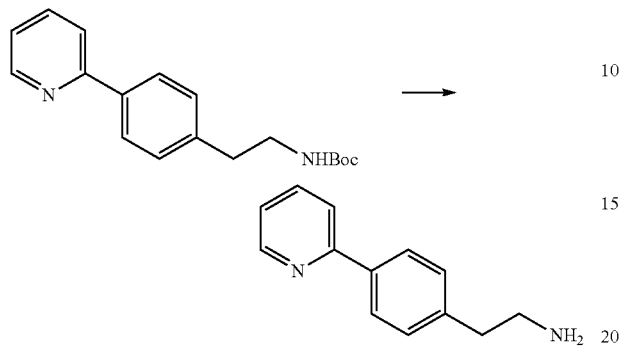

HCl (4 mL, 4N solution in 1,4-dioxane) was added to a stirred solution of tert-butyl 4-(pyridin-2-yl)phenethylcarbamate (0.31 g, 1.04 mmol) in MeOH (1 mL) at room temperature for 2 h, then the excess solvent was removed under reduced pressure to afford the crude product was used for next step reaction without further purification.

Example 96

2-(Furan-2-yl)-N5-(4-(pyridin-2-yl)phenethyl)-[1,2,4]triazolo[1,5-a][1,3,5]triazine-5,7-diamine

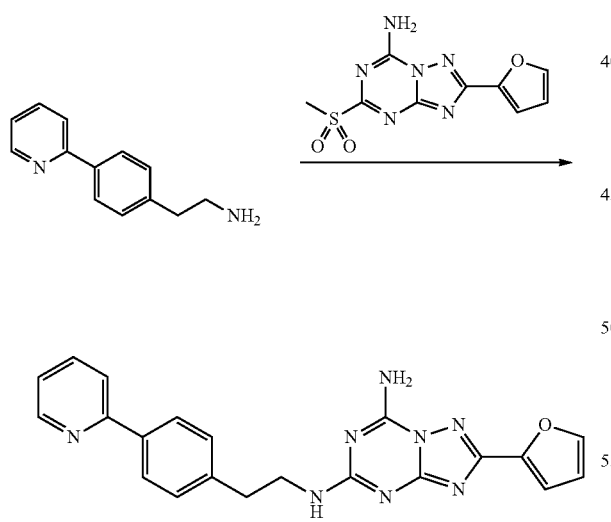

The reaction was carried out as in Example 5 to afford the title compound as white solid (0.1471 g, 44.4% yield). $^1$H NMR (500 MHz, DMSO-d6) δ: 8.65 (dd, J=4.7, 0.7 Hz, 1H), 8.33 (br, 2H), 8.03 (d, J=8.1 Hz, 2H), 7.94 (d, J=8.0 Hz, 1H), 7.91-7.81 (m, 2H), 7.55 (dd, J=26.4, 20.8 Hz, 1H), 7.39 (t, J=6.9 Hz, 2H), 7.33 (ddd, J=7.3, 4.8, 0.9 Hz, 1H), 7.07 (d, J=3.2 Hz, 1H), 6.74-6.62 (m, 1H), 3.54 (dd, J=13.4, 6.8 Hz, 2H), 2.93 (t, J=7.3 Hz, 2H).

Example 97 tert-Butyl 4-(pyridin-3-yl)phenethylcarbamate

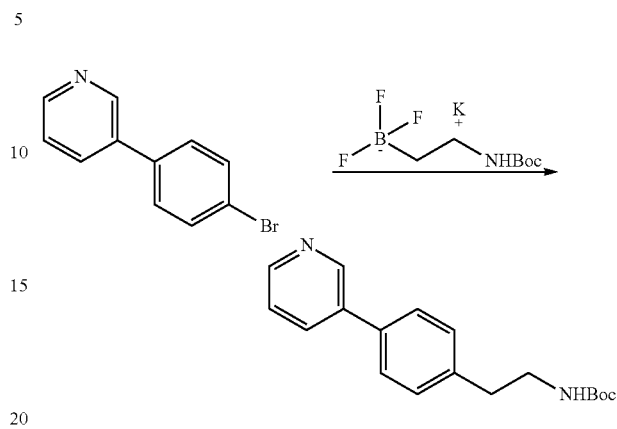

A solution of 3-(4-bromophenyl)pyridine (0.6 g, 2.56 mmol), potassium tert-butyl N-[2-(trifluoroboranuidyl)ethyl]carbamate (0.708 g, 2.82 mmol), cesium carbonate (2.5 g, 7.68 mmol), Pd(dppf)Cl$_2$ (0.095 g, 0.13 mmol) in PhMe (12 mL) and water (4 mL) was stirred at 80° C. overnight under N$_2$. The reaction mixture was filtered through Celite, the filtrate was concentrated in vacuo, diluted with water (30 mL) and extracted with ethyl acetate (30 mL×2), the combined organic layers washed with water (20 mL) and brine (20 mL). After drying with Na$_2$SO$_4$ and removal of solvent, the residue purified by column chromatography to afford the title compound as light-yellow oil (0.201 g, 26.3% yield). $^1$H NMR (500 MHz, DMSO-d6) 8.88 (d, J=1.9 Hz, 1H), 8.56 (dd, J=4.7, 1.6 Hz, 1H), 8.09-8.01 (m, 1H), 7.66 (d, J=8.2 Hz, 2H), 7.48 (ddd, J=8.0, 4.8, 0.6 Hz, 1H), 7.33 (d, J=8.1 Hz, 2H), 6.91 (t, J=5.4 Hz, 1H), 3.18 (d, J=5.2 Hz, 2H), 2.75 (t, J=7.4 Hz, 2H), 1.38 (s, 9H).

Example 98

2-(4-(Pyridin-3-yl)phenyl)ethanamine

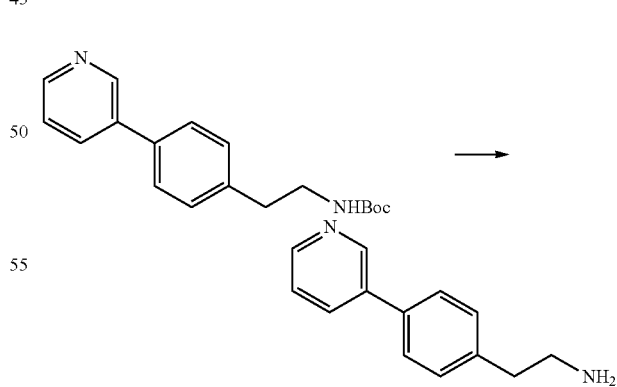

HCl (4 mL, 4N solution in 1,4-dioxane) was added to a stirred solution of tert-Butyl 4-(pyridin-3-yl)phenethylcarbamate (0.201 g, 0.673 mmol) in MeOH (2 mL) at room temperature for 2 h, then the excess solvent was removed under reduced pressure to afford the crude product was used for next step reaction without further purification.

Example 99

2-(Furan-2-yl)-N5-(4-(pyridin-3-yl)phenethyl)-[1,2,4]triazolo[1,5-a][1,3,5]triazine-5,7-diamine

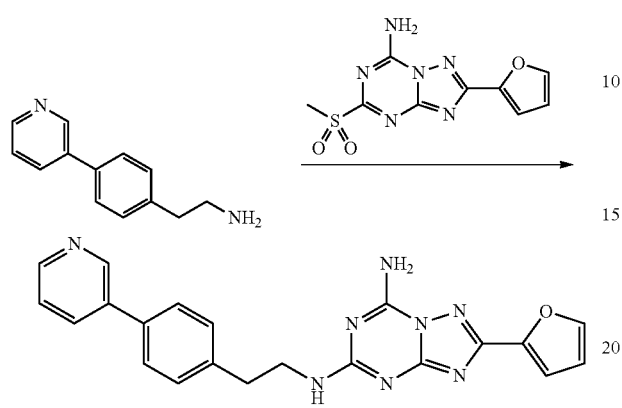

The reaction was carried out as in Example 5 to afford the title compound as white solid (0.0342 g, 14.2% yield). LC-MS m/z [M+H]$^+$: 399; $^1$H NMR (500 MHz, DMSO-d6) δ: 8.96-8.83 (m, 1H), 8.55 (dd, J=4.7, 1.5 Hz, 1H), 8.34 (br, 2H), 8.08-8.03 (m, 1H), 7.87 (s, 1H), 7.68 (d, J=8.0 Hz, 2H), 7.54 (dd, J=26.5, 20.9 Hz, 1H), 7.47 (dd, J=7.9, 4.8 Hz, 1H), 7.40 (t, J=7.1 Hz, 2H), 7.07 (dd, J=3.3, 0.6 Hz, 1H), 6.68 (dd, J=3.2, 1.7 Hz, 1H), 3.54 (dd, J=13.1, 6.5 Hz, 2H), 2.93 (t, J=7.3 Hz, 2H).

Example 100 tert-Butyl 4-(pyridin-4-yl)phenethylcarbamate

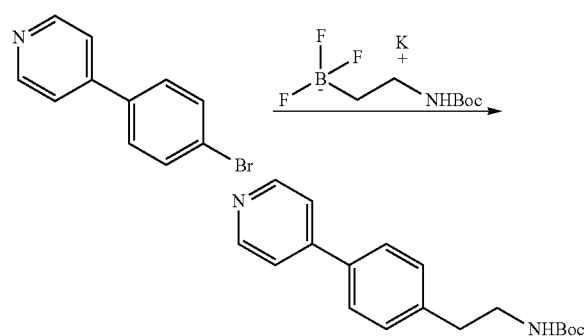

A solution of 4-(4-bromophenyl)pyridine (0.6 g, 2.56 mmol), potassium tert-butyl N-[2-(trifluoroboranuidyl)ethyl]carbamate (0.708 g, 2.82 mmol), cesium carbonate (2.5 g, 7.68 mmol), Pd(dppf)Cl$_2$ (0.095 g, 0.13 mmol) in PhMe (12 mL) and water (4 mL) was stirred at 80° C. overnight under N$_2$. The reaction mixture was filtered through Celite, the filtrate was concentrated in vacuo, diluted with water (30 mL) and extracted with ethyl acetate (30 mL×2), the combined organic layers washed with water (20 mL) and brine (20 mL). After drying with Na$_2$SO$_4$ and removal of solvent, the residue purified by column chromatography to afford the title compound as light-yellow solid (0.19 g, 24.9% yield). $^1$H NMR (500 MHz, DMSO-d6) 8.62 (dd, J=4.5, 1.6 Hz, 2H), 7.79-7.62 (m, 4H), 7.35 (d, J=8.1 Hz, 2H), 6.92 (t, J=5.3 Hz, 1H), 3.19 (dd, J=13.6, 6.6 Hz, 2H), 2.76 (t, J=7.3 Hz, 2H), 1.37 (s, 9H).

Example 101

2-(4-(pyridin-4-yl)phenyl)ethanamine

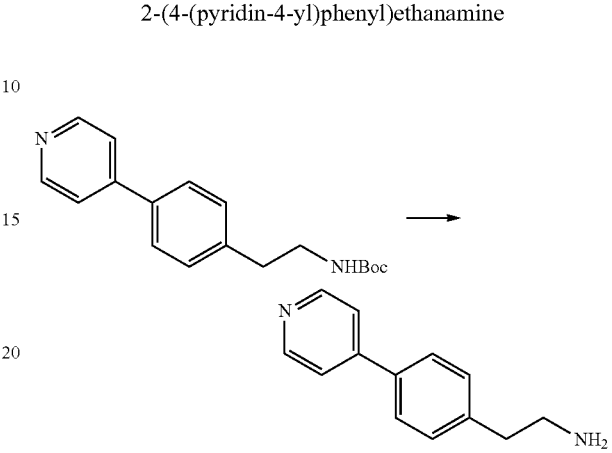

HCl (4 mL, 4N solution in 1,4-dioxane) was added to a stirred solution of tert-Butyl 4-(pyridin-4-yl)phenethylcarbamate (0.19 g, 0.637 mmol) in MeOH (2 mL) at room temperature for 2 h, then the excess solvent was removed under reduced pressure to afford the crude product was used for next step reaction without further purification.

Example 102

2-(Furan-2-yl)-N5-(4-(pyridin-4-yl)phenethyl)-[1,2,4]triazolo[1,5-a][1,3,5]triazine-5,7-diamine

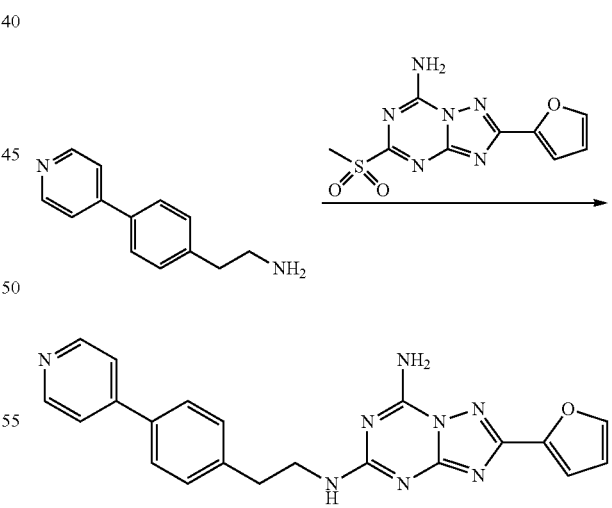

The reaction was carried out as in Example 5 to afford the title compound as white solid (0.0727 g, 30.2% yield). $^1$H NMR (500 MHz, DMSO-d6) δ: 8.62 (d, J=5.9 Hz, 2H), 8.32 (br, 2H), 7.87 (s, 1H), 7.75 (d, J=8.0 Hz, 2H), 7.70 (dd, J=4.6, 1.6 Hz, 2H), 7.54 (dd, J=26.4, 20.8 Hz, 1H), 7.41 (d, J=7.9 Hz, 2H), 7.07 (d, J=3.3 Hz, 1H), 6.72-6.63 (m, 1H), 3.65-3.48 (m, 2H), 2.94 (t, J=7.3 Hz, 2H).

Example 103

2-Benzyl-5-(4-bromophenyl)-2H-tetrazole

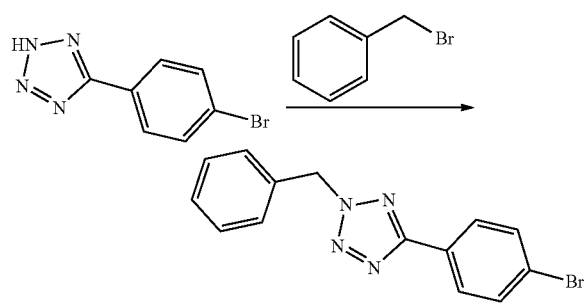

To a solution of 5-(4-bromophenyl)-2H-tetrazole (1.0 g, 4.44 mmol) in MeCN (30 mL) was added $Cs_2CO_3$ (2.9 g, 8.88 mmol) and 1-(bromomethyl)benzene (1.14 g, 6.66 mmol). The reaction mixture was stirred at 70° C. for 3 h. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:6) to afford the title compound as white solid (1.4 g, 100%). $^1$H NMR (500 MHz, DMSO-d6): 7.98 (d, 2H), 7.76 (d, 2H), 7.38-7.42 (m, 5H), 6.00 (s, 2H).

Example 104 tert-Butyl 4-(2-benzyl-2H-tetrazol-5-yl)phenethylcarbamate

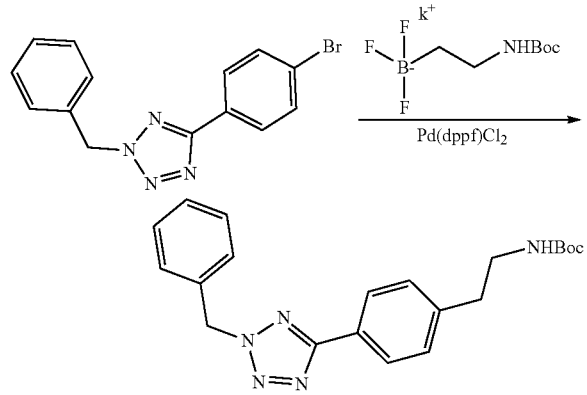

To a solution of 2-benzyl-5-(4-bromophenyl)-2H-tetrazole 1 (700 mg, 2.22 mmol) in toluene (20 mL) and water (7 mL) was added $Cs_2CO_3$ (1.4 g, 4.44 mmol), Pd(dppf)Cl$_2$ (163 mg, 0.22 mmol) and potassium tert-butyl N-[2-(trifluoroboranuidyl)ethyl]carbamate (613 mg, 2.44 mmol). The reaction mixture was stirred at 80° C. overnight under $N_2$. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:4) to afford the title compound as white solid (515 mg, 61%). $^1$H NMR (500 MHz, DMSO-d6): 7.96 (d, 2H), 7.31-7.41 (m, 7H), 7.53-7.62 (m, 1H), 6.90 (t, 1H), 5.99 (s, 2H), 3.16-3.20 (m, 2H), 2.76 (t, 2H), 1.36 (s, 9H).

Example 105

2-(4-(2-Benzyl-2H-tetrazol-5-yl)phenyl)ethanamine

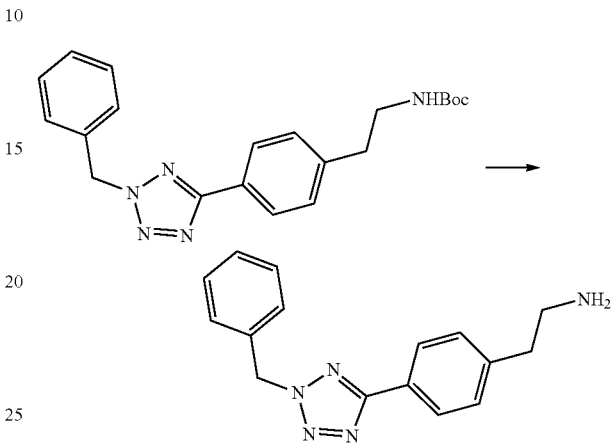

To a solution of tert-butyl 4-(2-benzyl-2H-tetrazol-5-yl) phenethylcarbamate (381 mg, 1.00 mmol) in 1,4-dioxane (5 mL) was added 4N HCl/dioxane (3 mL). The reaction mixture was stirred at room temperature 1 h. TLC showed the reaction completed. The excess HCl and dioxane were removed. The crude product was use for the next step directly.

Example 106

N5-(4-(2-Benzyl-2H-tetrazol-5-yl)phenethyl)-2-(furan-2-yl)-[1,2,4]triazolo[1,5-a][1,3,5]triazine-5,7-diamine

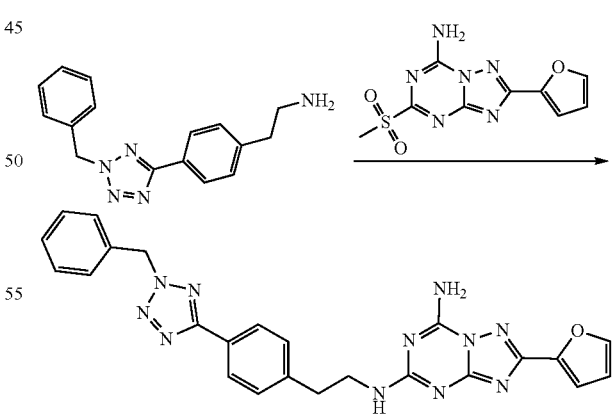

The reaction was carried out as in Example 5 to afford the title compound as white solid (102.1 mg, 24%). $^1$H NMR (500 MHz, DMSO-d6): 8.16-8.46 (m, 2H), 7.98 (d, 2H), 7.87 (s, 1H), 7.51-7.60 (m, 1H), 7.37-7.50 (m, 7H), 7.05 (d, 1H), 6.68 (dr, 1H), 5.99 (s, 2H), 3.53-3.55 (m, 2H), 2.94 (t, 2H).

Example 107

4-((5-(4-Bromophenyl)-2H-tetrazol-2-yl)methyl)pyridine

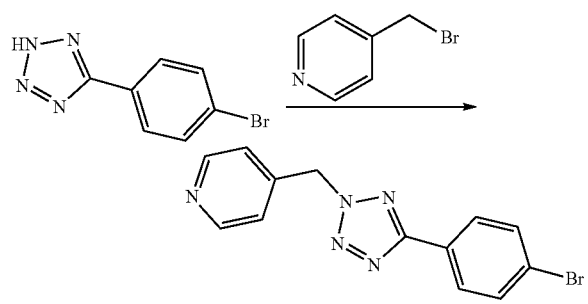

To a solution of 5-(4-bromophenyl)-2H-tetrazole (1.0 g, 4.44 mmol) in MeCN (35 mL) was added $Cs_2CO_3$ (5.9 g, 18.1 mmol) and 4-(bromomethyl)pyridine hydrochloride (1.0 g, 6.1 mmol). The reaction mixture was stirred at 70° C. for 3 h. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc) to afford the title compound as white solid (800 mg, 57%). $^1$H NMR (500 MHz, DMSO-d6): 8.60 (dd, 2H), 8.00 (d, 2H), 7.77 (d, 2H), 7.33 (d, 2H), 6.12 (s, 2H).

Example 108 tert-Butyl 4-(2-(pyridin-4-ylmethyl)-2H-tetrazol-5-yl)phenethylcarbamate

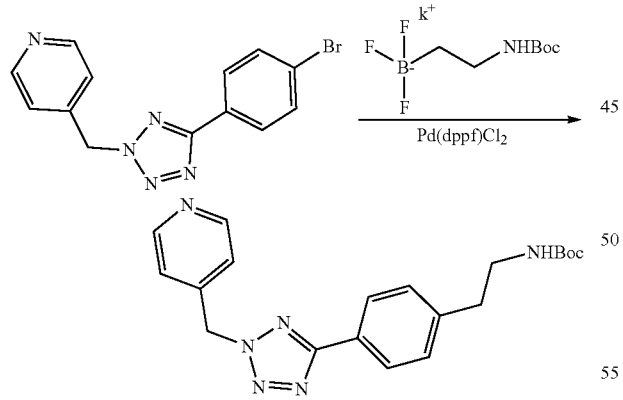

To a solution of 4-((5-(4-bromophenyl)-2H-tetrazol-2-yl)methyl)pyridine (800 mg, 2.53 mmol) in toluene (20 mL) and water (7 mL) was added $Cs_2CO_3$ (1.65 g, 5.07 mmol), Pd(dppf)Cl$_2$ (186 mg, 0.25 mmol) and potassium tert-butyl N-[2-(trifluoroboranuidyl)ethyl]-carbamate (700 mg, 2.79 mmol). The reaction mixture was stirred at 80° C. overnight under N$_2$. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:4) to afford the title compound as white solid (637 mg, 66%). $^1$H NMR (500 MHz, DMSO-d6): 8.60 (dd, 2H), 7.98 (d, 2H), 7.38 (d, 2H), 7.32 (d, 2H), 6.91 (t, 1H), 6.10 (s, 2H), 3.16-3.20 (m, 2H), 2.76 (t, 2H), 1.36 (s, 9H).

Example 109

2-(4-(2-(Pyridin-4-ylmethyl)-2H-tetrazol-5-yl)phenyl)ethanamine

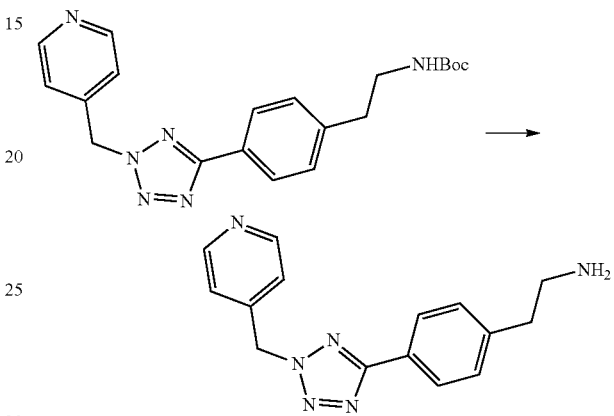

To a solution of tert-butyl 4-(2-(pyridin-4-ylmethyl)-2H-tetrazol-5-yl)phenethyl-carbamate (300 mg, 0.80 mmol) in 1,4-dioxane (5 mL) was added 4N HCl/dioxane (3 mL). The reaction mixture was stirred at room temperature 1.5 h. TLC showed the reaction completed. The excess HCl and dioxane were removed. The crude product was use for the next step directly.

Example 110

N5-(4-(2-(Pyridin-4-ylmethyl)-2H-tetrazol-5-yl)phenethyl)-2-(furan-2-yl)-[1,2,4]triazolo[1,5-a][1,3,5]triazine-5,7-diamine

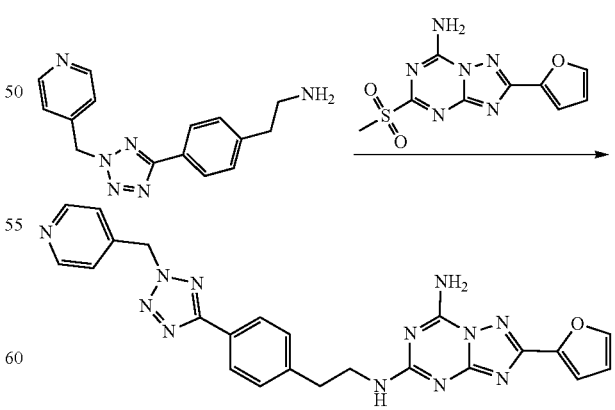

The reaction was carried out as in Example 5 to afford the title compound as white solid (205.6 mg, 59.7%). $^1$H NMR (500 MHz, DMSO-d6): 8.59 (d, 2H), 8.11-8.45 (m, 2H), 8.00 (d, 2H), 7.87 (s, 1H), 7.52-7.60 (m, 1H), 7.44-7.47 (m, 2H), 7.32 (d, 2H), 7.05 (d, 1H), 6.68 (dr, 1H), 6.10 (s, 2H), 3.53-3.55 (m, 2H), 2.94 (t, 2H).

Example 111

3-((5-(4-Bromophenyl)-2H-tetrazol-2-yl)methyl)pyridine

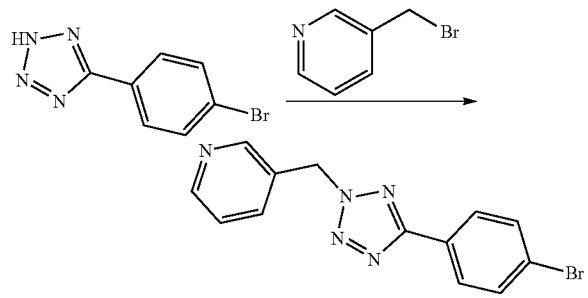

To a solution of 5-(4-bromophenyl)-2H-tetrazole (1.0 g, 4.44 mmol) in MeCN (30 mL) was added Cs$_2$CO$_3$ (4.3 g, 13.2 mmol) and 3-(bromomethyl)pyridine hydrochloride (1.46 g, 5.7 mmol). The reaction mixture was stirred at 70° C. for 2 h. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:3) to afford the title compound as white solid (393 mg, 24%). $^1$H NMR (500 MHz, DMSO-d6): 8.72 (d, 1H), 8.60 (dd, 1H), 7.98 (d, 2H), 7.85-7.86 (m, 1H), 7.76 (d, 2H), 7.44-7.46 (m, 1H), 6.09 (s, 1H).

Example 112 tert-Butyl 4-(2-(pyridin-3-ylmethyl)-2H-tetrazol-5-yl)phenethylcarbamate

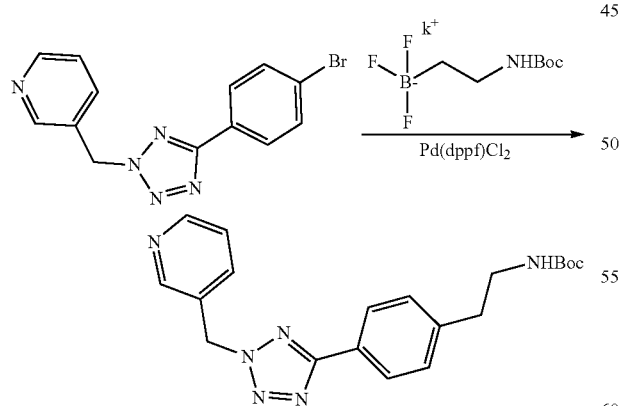

To a solution of 3-((5-(4-bromophenyl)-2H-tetrazol-2-yl)methyl)pyridine (393 mg, 1.24 mmol) in toluene (15 mL) and water (5 mL) was added Cs$_2$CO$_3$ (808 g, 2.48 mmol), Pd(dppf)Cl$_2$ (91 mg, 0.12 mmol) and potassium tert-butyl N-[2-(trifluoroboranuidyl)ethyl]carbamate (345 mg, 1.37 mmol). The reaction mixture was stirred at 80° C. overnight under N$_2$. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:4) to afford the title compound as yellow oil (280 mg, 59%). $^1$H NMR (500 MHz, DMSO-d6): 8.71 (d, 1H), 8.60 (dd, 1H), 7.96 (d, 2H), 7.84 (dt, 1H), 7.43-7.46 (m, 1H), 7.37 (m, 2H), 6.90 (t, 1H), 6.07 (s, 2H), 3.16-3.20 (m, 2H), 2.76 (t, 2H), 1.36 (s, 9H).

Example 113

2-(4-(2-(Pyridin-3-ylmethyl)-2H-tetrazol-5-yl)phenyl)ethanamine

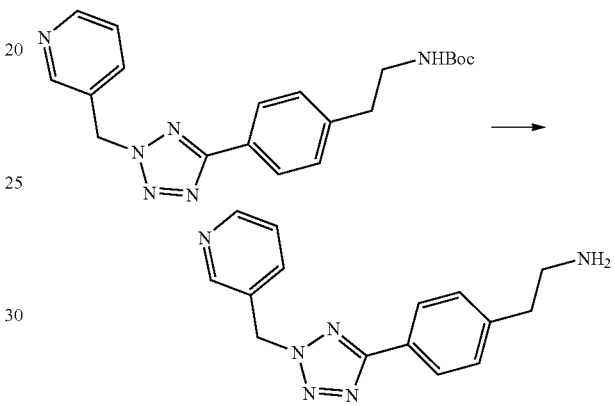

To a solution of tert-butyl 4-(2-(pyridin-3-ylmethyl)-2H-tetrazol-5-yl)phenethyl-carbamate (280 mg, 0.73 mmol) in 1,4-dioxane (5 mL) was added 4N HCl/dioxane (3 mL). The reaction mixture was stirred at room temperature 1.5 h. TLC showed the reaction completed. The excess HCl and dioxane were removed. The crude product was use for the next step directly.

Example 114

N5-(4-(2-(pyridin-3-ylmethyl)-2H-tetrazol-5-yl)phenethyl)-2-(furan-2-yl)-[1,2,4]triazolo[1,5-a][1,3,5]triazine-5,7-diamine

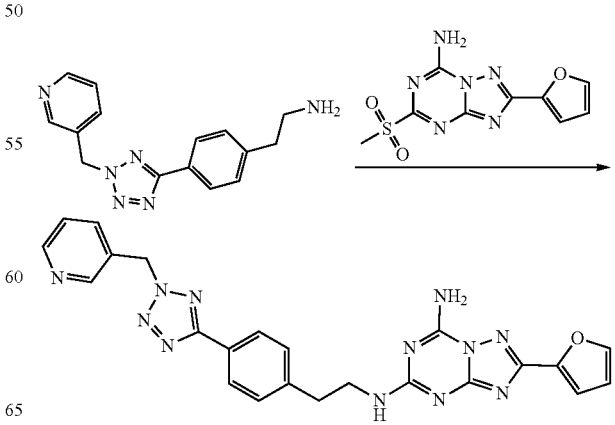

The reaction was carried out as in Example 5 to afford the title compound as white solid (111.6 mg, 36%). ¹H NMR (500 MHz, DMSO-d6): 8.71 (d, 1H), 8.59 (dd, 1H), 8.11-8.45 (m, 2H), 7.98 (d, 2H), 7.83-7.87 (m, 3H), 7.52-7.60 (m, 1H), 7.43-7.46 (m, 3H), 7.32 (d, 2H), 7.05 (d, 1H), 6.68 (dr, 1H), 6.07 (s, 2H), 3.53-3.55 (m, 2H), 2.94 (t, 2H).

Example 115

2-(5-(4-Bromophenyl)-2H-tetrazol-2-yl)acetonitrile

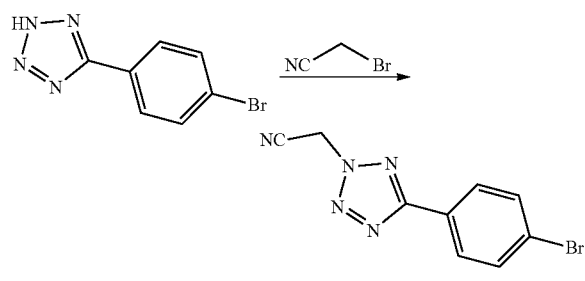

To a solution of 5-(4-bromophenyl)-2H-tetrazole (1.0 g, 4.44 mmol) in MeCN (30 mL) was added Cs₂CO₃ (2.9 g, 8.92 mmol) and 2-bromoacetonitrile (700 mg, 5.83 mmol). The reaction mixture was stirred at 60° C. for 3 h. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:5) to afford the title compound as white solid (600 mg, 51.2%). ¹H NMR (500 MHz, DMSO-d6): 8.08 (d, 2H), 7.86 (d, 2H), 6.35 (s, 2H).

Example 116 tert-Butyl 4-(2-(cyanomethyl)-2H-tetrazol-5-yl)phenethylcarbamate

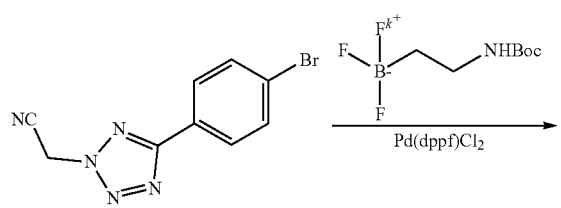

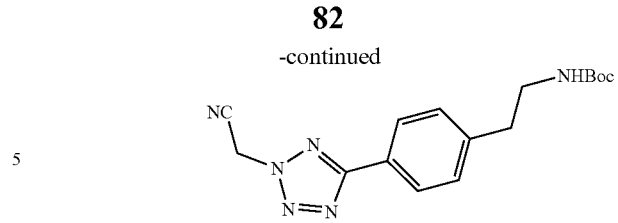

To a solution of 2-(5-(4-bromophenyl)-2H-tetrazol-2-yl)acetonitrile (600 mg, 2.27 mmol) in toluene (20 mL) and water (6 mL) was added Cs₂CO₃ (1.5 g, 4.5 mmol), Pd(dppf)Cl₂ (166 mg, 0.22 mmol) and potassium tert-butyl N-[2-(trifluoroboranuidyl)ethyl]carbamate (627 mg, 2.50 mmol). The reaction mixture was stirred at 80° C. overnight under N₂. TLC showed the reaction completed, the reaction mixture was quenched with water and extracted with EtOAc. The combined organic layers were washed with water and brine, dried over sodium sulfate and concentrated in vacuo. The crude product was purified by column chromatography (EtOAc:Hexane=1:4) to afford the title compound as white solid (220 mg, 29%). ¹H NMR (500 MHz, DMSO-d6): 8.00 (d, 2H), 7.41 (d, 2H), 6.93 (t, 1H), 6.29 (s, 2H), 3.18-3.20 (m, 2H), 2.78 (t, 2H), 1.36 (s, 9H).

Example 117

2-(5-(4-(2-Aminoethyl)phenyl)-2H-tetrazol-2-yl)acetonitrile

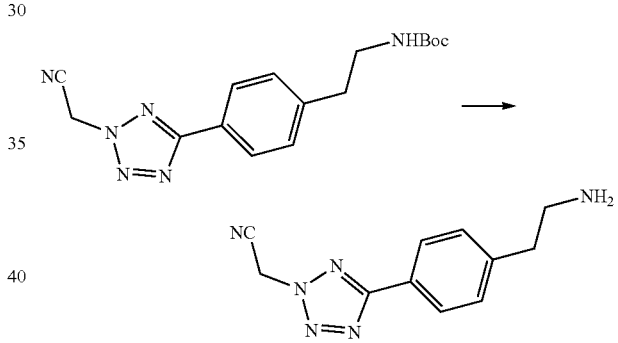

To a solution of tert-butyl 4-(2-(cyanomethyl)-2H-tetrazol-5-yl)phenethylcarbamate (220 mg, 0.67 mmol) in 1,4-dioxane (5 mL) was added 4N HCl/dioxane (3 mL). The reaction mixture was stirred at room temperature 1.5 h. TLC showed the reaction completed. The excess HCl and dioxane were removed. The crude product was use for the next step directly.

Example 118

2-(5-(4-(2-(7-Amino-2-(furan-2-yl)-[1,2,4]triazolo[1,5-a][1,3,5]triazin-5-ylamino)ethyl)-phenyl)-2H-tetrazol-2-yl)acetonitrile

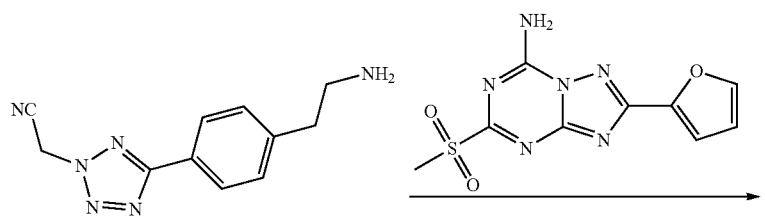

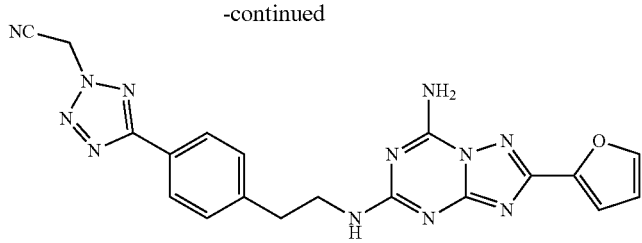

The reaction was carried out as in Example 5 to afford the title compound as white solid (15.5 mg, 10%). LCMS [M+1]⁺: 429.2 ¹H NMR (500 MHz, DMSO-d6): 8.17-8.24 (m, 2H), 8.01 (d, 2H), 7.87 (s, 1H), 7.47-7.62 (m, 3H), 7.44-7.47 (m, 3H), 7.06 (d, 1H), 6.68 (dr, 1H), 6.29 (s, 2H), 3.54-3.57 (m, 2H), 2.96 (t, 2H).

Example 119

4-(2-Aminoethyl)benzonitrile

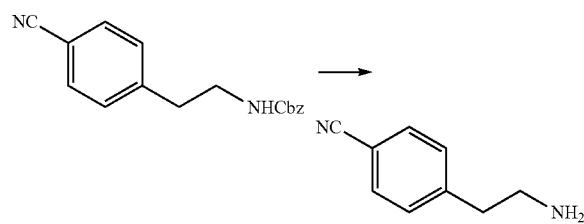

To a solution of benzyl 4-cyanophenethylcarbamate (550 mg, 1.96 mmol) in MeOH (20 mL) was added Pd/C (10%, 50 mg). The reaction mixture was stirred at 40° C. overnight under H₂. TLC showed the reaction completed, the reaction mixture was filtered by diatomite. The filtrate was concentrated to afford the title compound as yellow oil.

Example 120

4-(2-(7-Amino-2-(furan-2-yl)-[1,2,4]triazolo[1,5-a][1,3,5]triazin-5-ylamino)ethyl)-benzonitrile

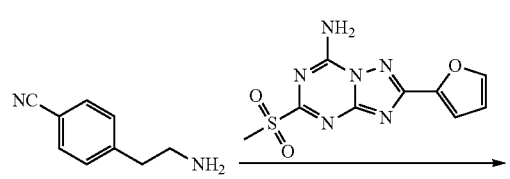

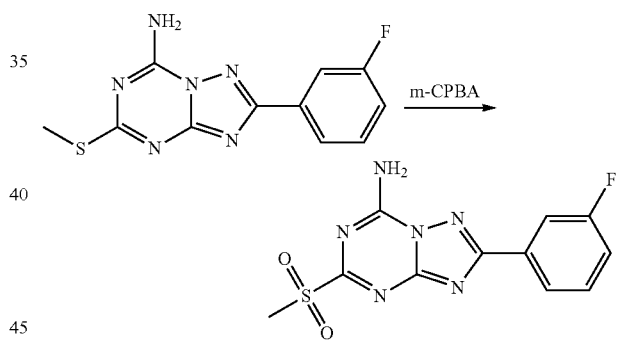

The reaction was carried out as in Example 5 to afford the title compound as white solid (54 mg, 12.2%). ¹H NMR (500 MHz, DMSO-d6): 8.04-8.45 (m, 2H), 7.87 (s, 1H), 7.76 (d, 2H), 7.45-7.59 (m, 3H), 7.06 (d, 1H), 6.68 (dr, 1H), 3.50-3.54 (m, 2H), 2.96 (t, 2H).

Example 121

2-(3-Fluorophenyl)-5-(methylsulfonyl)-[1,2,4]triazolo[1,5-a][1,3,5]triazin-7-amine The title compound was prepared in a similar way as the title compound in Example 4. ¹H NMR (500 MHz, DMSO-d6) δ: 9.87 (s, 1H), 9.41 (s, 1H), 8.04 (d, 1H), 7.91 (d, 1H), 7.65 (q, 1H), 7.43 (dt, 1H), 3.38 (s, 3H).

Example 122

2-(3-Fluorophenyl)-N5-(4-(2-methyl-2H-tetrazol-5-yl)phenethyl)-[1,2,4]triazolo[1,5-a][1,3,5]triazine-5,7-diamine

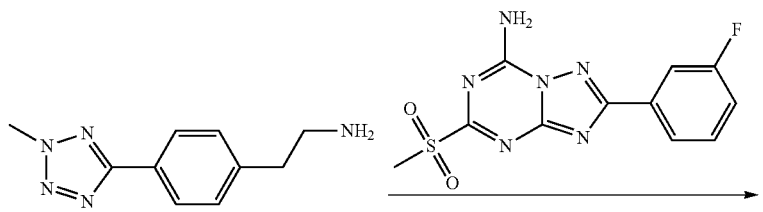

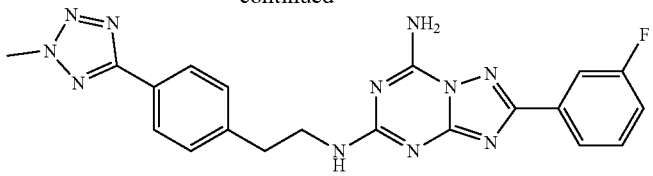

To a stirred solution of 2-(4-(2-methyl-2H-tetrazol-5-yl)phenyl)ethanamine (203 mg, 1.00 mmol) and 2-(3-fluorophenyl)-5-(methylsulfonyl)-[1,2,4]triazolo[1,5-a][1,3,5]triazin-7-amine (308 mg, 1.00 mmol) in MeCN (5 mL) was added TEA to adjust PH to 8. The reaction mixture was stirred at room temperature for 15 h. The precipitated solid was collected by filtration, washed with methanol and dried to afford the title compound as white solid (226 mg, 52.4% yield). $^1$H NMR (500 MHz, DMSO-d6) δ: 8.05-8.49 (m, 2H), 7.99 (d, 2H), 7.95 (d, 1H), 7.81 (d, 1H), 7.57 (m, 2H), 7.46 (t, 2H), 7.35 (dt, 1H), 4.41 (s, 3H), 3.57 (q, 2H), 2.96 (t, 2H).

Example 123

2-(3-Fluorophenyl)-N5-(4-(2-methyl-2H-tetrazol-5-yl)phenethyl)-[1,2,4]triazolo[1,5-a][1,3,5]triazine-5,7-diamine

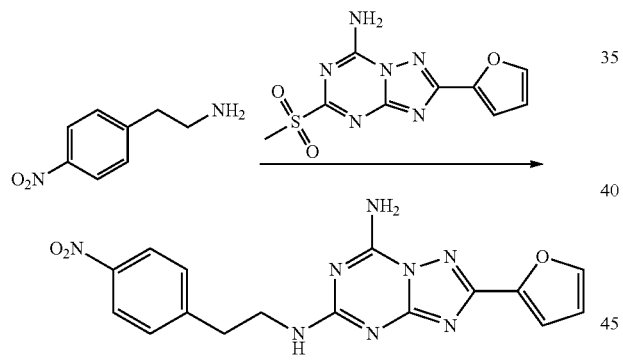

The reaction was carried out as in Example 5 to afford the title compound as white solid. $^1$H NMR (500 MHz, DMSO-d6) δ: 8.05-8.51 (m, 4H), 7.87 (s, 1H), 7.72 (q, 1H), 7.54 (m, 3H), 7.05 (d, 1H), 6.68 (t, 1H), 3.56 (q, 2H), 3.02 (t, 2H).

Example 124

2-(4-(2H-Tetrazol-5-yl)phenyl)ethanamine

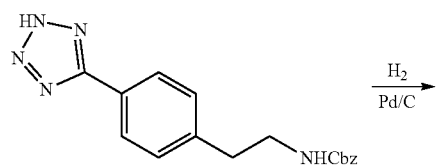

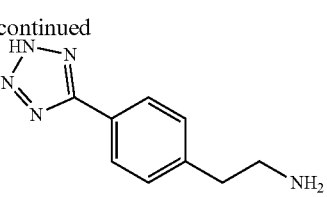

To a solution of benzyl 4-(2H-tetrazol-5-yl)phenethylcarbamate (100 mg, 0.30 mmol) in MeOH (20 mL) was added Pd/C (10%, 20 mg). The reaction mixture was stirred under H$_2$ at 50° C. for 3 h. TLC showed the reaction completed. The reaction mixture was filtered through diatomite. The filtrate was concentrated to afford the title compound as white solid (60 mg, 100%). $^1$H NMR (500 MHz, DMSO-d6) δ: 7.92 (d, 2H), 7.74 (dr, 2H), 7.26 (d, 2H), 3.07 (t, 2H), 2.86 (t, 2H).

Example 125

N5-(4-(2H-Tetrazol-5-yl)phenethyl)-2-(furan-2-yl)-[1,2,4]triazolo[1,5-a][1,3,5]triazine-5,7-diamine

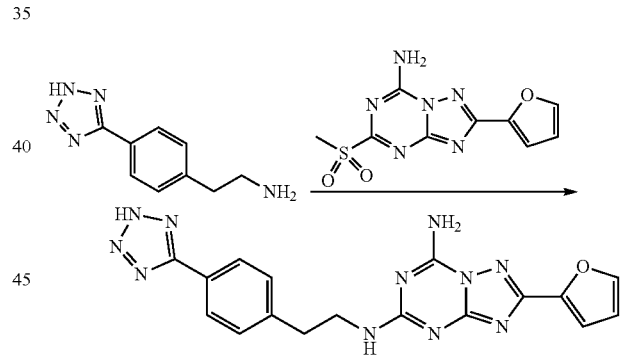

The reaction was carried out as in Example 5 to afford the title compound as white solid (18.7 mg, 12%). LCMS [M+1]$^+$: 390.2 $^1$H NMR (500 MHz, DMSO-d6): 7.95 (d, 2H), 7.68 (s, 1H), 7.35 (d, 2H), 7.11 (d, 1H), 6.60 (dr, 1H), 3.64-3.67 (m, 2H), 2.94-2.99 (m, 2H).

Example 126

2-(Furan-2-yl)-N5-(2-(pyridin-3-yl)ethyl)-[1,2,4]triazolo[1,5-a][1,3,5]triazine-5,7-diamine

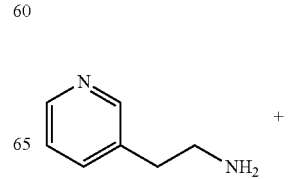

-continued

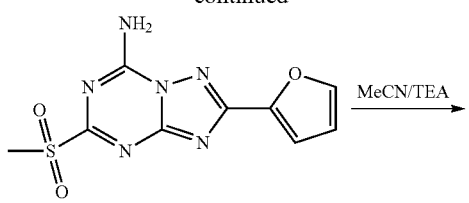

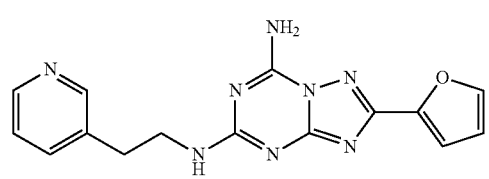

The reaction was carried out as in Example 5 to afford the title compound as white solid (64.8 mg, 20.12% yield). $^1$H NMR (500 MHz, CDCl$_3$) 8.47 (d, J=9.3 Hz, 1H), 8.41 (dd, J=4.7, 1.3 Hz, 1H), 8.19 (s, 2H), 7.86 (s, 1H), 7.67 (t, J=8.7 Hz, 1H), 7.53 (dd, J=29.5, 24.0 Hz, 1H), 7.31 (dd, J=7.7, 4.8 Hz, 1H), 7.05 (d, J=3.3 Hz, 1H), 6.67 (d, J=1.5 Hz, 1H), 3.51 (dd, J=13.3, 6.7 Hz, 2H), 2.88 (t, J=7.1 Hz, 2H).

Example 127

2-(Furan-2-yl)-N5-(2-(6-methoxypyridin-3-yl)ethyl)-[1,2,4]triazolo[1,5-a][1,3,5]triazine-5,7-diamine

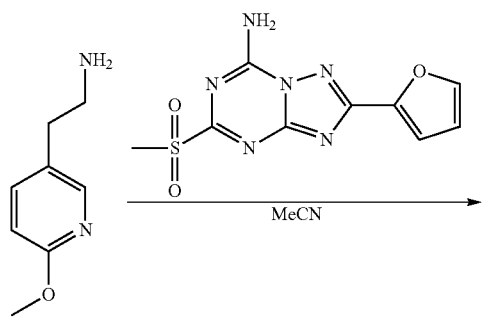

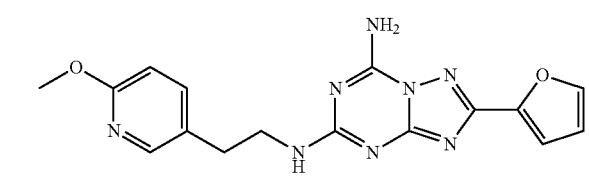

The reaction was carried out as in Example 5 to afford the title compound as white solid (135 mg, 38.4% yield). $^1$H NMR (500 MHz, DMSO-d6) δ: 8.50-8.05 (d, 2H), 8.02 (d, 1H), 7.87 (s, 1H), 7.63-7.46 (m, 2H), 7.06 (d, 1H), 6.75 (d, 1H), 6.67 (d, 1H), 3.81 (s, 3H), 3.46 (q, 2H), 2.81 (t, 2H).

Example 128

2-(Furan-2-yl)-N5-(2-(pyrimidin-4-yl)ethyl)-[1,2,4]triazolo[1,5-a][1,3,5]triazine-5,7-diamine

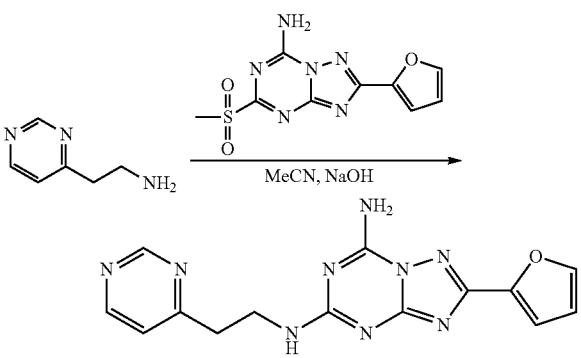

The reaction was carried out as in Example 42. The precipitated solid was filtered, washed with MeCN and water, and dried to afford the title compound as yellow solid (135 mg, 41.8% yield). $^1$H NMR (500 MHz, DMSO-d6) δ: 9.09 (s, 1H), 8.68 (d, 1H), 8.50-8.05 (d, 2H), 7.87 (s, 1H), 7.50-7.43 (m, 2H), 7.06 (d, 1H), 6.67 (s, 1H), 3.66 (m, 2H), 3.03 (t, 2H).

Example 129

2-(Furan-2-yl)-N5-(2-(pyridin-2-yl)ethyl)-[1,2,4]triazolo[1,5-a][1,3,5]triazine-5,7-diamine

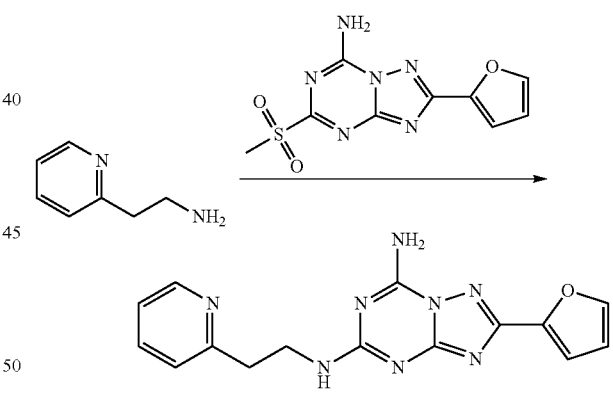

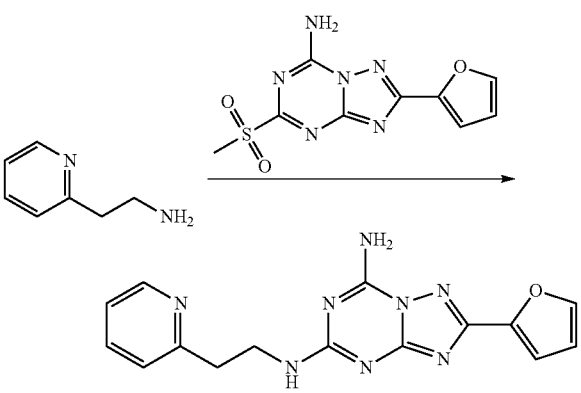

The reaction was carried out as in Example 5 to afford the title compound (361 mg, 74.4% yield). $^1$H NMR (500 MHz, DMSO-d6) δ: 8.51 (s, 1H), 8.04-8.40 (d, 2H), 7.87 (s, 1H), 7.72 (q, 1H), 7.47-7.54 (d, 1H), 7.29 (d, 1H), 7.21 (t, 1H), 7.06 (s, 1H), 6.67 (s, 1H), 3.63 (t, 2H), 3.02 (t, 2H).

The above exemplary embodiments are used as illustrations of the invention. These embodiments are not intended to limit the scope of the invention. In fact, the invention is intended to cover all alternatives, modifications, and equivalents of these embodiments. It should not be understood that the present invention is only limited to the illustrated examples.

Biological Activities of the A2A Receptor Antagonists

The antagonistic activities of the triazolotriazine derivatives of the present invention were measured in a functional cAMP production assay. The assay consists of NECA stimulation of cAMP production and its inhibition by A2AR antagonists in A2AR-expressing HEK293 cells (hADORA2A-HEK293). All cells were cultured in complete medium at 37° C. in 5% $CO_2$. The cells were detached with pancreatin and collected at 200 g for 5 min. After resuspending the cells in fresh complete medium, the cell viability is counted using the trypan blue exclusion method. The cAMP production assay was conducted only when cell viability was greater than 95%. After the cells were diluted with Hank's buffered saline solution containing HEPES (5 mM), BSA stabilizer (0.1%) and 20 Rolipram (10 μM), cells were loaded into white opaque 384-well plates (~500 cells/well, 10 μl/well) and incubated with test compound at a suitable concentration range (11 concentrations) for 20 min at room temperature. Then the A2A receptor agonist NECA (final concentration=$EC_{80}$, which was determined in the same experiment slightly earlier) was added to the sample and the mixture was incubated again for 30 min at 37° C. The amount of cAMP production was determined using Eu-cAMP tracer and Ulight-anti-cAMP by measuring the ratio of the TR-FRET emission at 665 nm and fluorescent emission at 615 nm. The inhibition rate (%) was calculated according to the following formula. The $IC_{50}$ values were calculated from concentration–inhibition (%) curves after log transformation.

$$\% \text{ Inhibition} = \left(1 - \frac{\text{Ratio}_{565nm/615nm\,high} - \text{Ratio}_{565nm/615nm\,cm\,pd}}{\text{Ratio}_{665nm/615nm\,high} - \text{Ratio}_{665nm/615nm\,low}}\right) \times 100\%$$

Table (2) shows representative antagonistic activities of the triazolotriazine derivatives of the present invention.

TABLE 2

The Potency of A2AR antagonists

| Compounds | A2AR Potency (nM) |
| --- | --- |
| Example 11 | 43.42 |
| Example 12 | 27.10 |
| Example 13 | 33.02 |
| Example 16 | 23.99 |
| Example 17 | 7.54 |
| Example 27 | 9.08 |
| Example 34 | 8.71 |
| Example 35 | 13.78 |
| Example 36 | 13.32 |
| Example 37 | 6.00 |
| Example 42 | 19.35 |
| Example 43 | 17.14 |
| Example 45 | 27.38 |
| Example 51 | 9.66 |
| Example 59 | 7.87 |
| Example 62 | 9.08 |
| Example 65 | 13.88 |
| Example 125 | 14.48 |
| Example 128 | 63.81 |
| Example 129 | 12.67 |
| ZM241385 | 9.00 |

The invention claimed is:
1. A compound of formula (1):

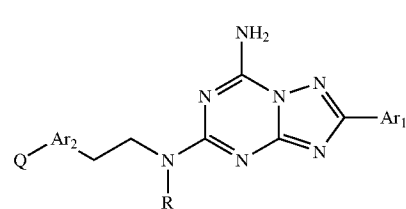

Formula 1 wherein:
R is hydrogen;
$Ar_1$ is 2-furanyl;
$Ar_2$ is phenyl or pyridyl; and
Q is a 5-6 membered aromatic ring that is optionally substituted with X; X is optionally substituted $C_{1-3}$ alkyl; any of said optionally substituted alkyl groups is substituted by halogen, cyano, methoxy, aryl, or heteroaryl,
or a pharmaceutically acceptable solvate or salt thereof.

2. The compound according to claim 1, wherein:
R is hydrogen;
$Ar_1$ is 2-furanyl;
$Ar_2$ is phenyl; and
Q is a tetrazole ring that is optionally substituted with X; X is optionally substituted $C_{1-3}$ alkyl; any of said optionally substituted alkyl groups is substituted by halogen, cyano, or methoxy,
or a pharmaceutically acceptable solvate or salt thereof.

3. A compound selected from:
N5-(4-(1-Methyl-1H-tetrazol-5-yl)phenethyl)-2-(furan-2-yl)-[1,2,4]triazolo[1,5-a][1,3,5]triazine-5,7-diamine;
N5-(4-(2-Methyl-2H-tetrazol-5-yl)phenethyl)-2-(furan-2-yl)-[1,2,4]triazolo[1,5-a][1,3,5]triazine-5,7-diamine;
N5-(4-(2-Ethyl-2H-tetrazol-5-yl)phenethyl)-2-(furan-2-yl)-[1,2,4]triazolo[1,5-a][1,3,5]triazine-5,7-diamine;
N5-(4-(2-Isopropyl-2H-tetrazol-5-yl)phenethyl)-2-(furan-2-yl)-[1,2,4]triazolo[1,5-a][1,3,5]triazine-5,7-diamine;
N5-(4-(2-Propyl-2H-tetrazol-5-yl)phenethyl)-2-(furan-2-yl)-[1,2,4]triazolo[1,5-a][1,3,5]triazine-5,7-diamine;
2-(5-(4-(2-(7-Amino-2-(furan-2-yl)-[1,2,4]triazolo[1,5-a][1,3,5]triazin-5-ylamino)ethyl)-phenyl)-2H-tetrazol-2-yl)acetonitrile;
N5-(4-(2-(2,2,2-Trifluoroethyl)-2H-tetrazol-5-yl)phenethyl)-2-(furan-2-yl)-[1,2,4]triazolo[1,5-a][1,3,5]triazine-5,7-diamine;
N5-(4-(2-(2-Methoxyethyl)-2H-tetrazol-5-yl)phenethyl)-2-(furan-2-yl)-[1,2,4]triazolo[1,5-a][1,3,5]triazine-5,7-diamine;
2-(Furan-2-yl)-N5-(4-(pyridin-2-yl)phenethyl)-[1,2,4]triazolo[1,5-a][1,3,5]triazine-5,7-diamine;
2-(Furan-2-yl)-N5-(4-(pyridin-3-yl)phenethyl)-[1,2,4]triazolo[1,5-a][1,3,5]triazine-5,7-diamine;
2-(Furan-2-yl)-N5-(4-(pyridin-4-yl)phenethyl)-[1,2,4]triazolo[1,5-a][1,3,5]triazine-5,7-diamine;
2-(Furan-2-yl)-N5-(4-(pyrimidin-2-yl)phenethyl)-[1,2,4]triazolo[1,5-a][1,3,5]triazine-5,7-diamine;
2-(Furan-2-yl)-N5-(4-(1-methyl-1H-1,2,4-triazol-3-yl)phenethyl)-[1,2,4]triazolo[1,5-a][1,3,5]triazine-5,7-diamine;

N5-(4-(2H-Tetrazol-5-yl)phenethyl)-2-(furan-2-yl)-[1,2,4]triazolo[1,5-a][1,3,5]triazine-5,7-diamine;

2-(3-Fluorophenyl)-N5-(4-(2-methyl-2H-tetrazol-5-yl)phenethyl)-[1,2,4]triazolo[1,5-a][1,3,5]triazine-5,7-diamine;

2-(3-Fluorophenyl)-N5-(4-(2-methyl-2H-tetrazol-5-yl)phenethyl)-[1,2,4]triazolo[1,5-a][1,3,5]triazine-5,7-diamine;

N5-(4-(2-Methyl-2H-tetrazol-5-yl)phenethyl)-2-phenyl-[1,2,4]triazolo[1,5-a][1,3,5]triazine-5,7-diamine; and 2-(Furan-2-yl)-N5-(2-(6-(2-methyl-2H-tetrazol-5-yl)pyridin-3-yl)ethyl)-[1,2,4]triazolo[1,5-a][1,3,5]triazine-5,7-diamine, or a pharmaceutically acceptable solvate or salt thereof.

* * * * *